(12) United States Patent
Shoshan-Barmatz

(10) Patent No.: US 11,174,484 B2
(45) Date of Patent: Nov. 16, 2021

(54) MEANS AND METHODS FOR REDUCING TUMORIGENICITY OF CANCER STEM CELLS

(71) Applicants: B. G. NEGEV TECHNOLOGIES AND APPLICATIONS LTD., AT BEN-GURION UNIVERSITY, Beer Sheva (IL); THE NATIONAL INSTITUTE FOR BIOTECHNOLOGY IN THE NEGEV LTD., Beer Sheva (IL)

(72) Inventor: Varda Shoshan-Barmatz, Omer (IL)

(73) Assignees: B. G. NEGEV TECHNOLOGIES AND APPLICATIONS LTD., AT BEN- GURION UNIVERSITY, Beer Sheva (IL); THE NATIONAL INSTITUTE FOR BIOTECHNOLOGY IN THE NEGEV LTD., Beer Sheva (IL)

( * ) Notice: Subject to any disclaimer, the term of this patent is extended or adjusted under 35 U.S.C. 154(b) by 0 days.

(21) Appl. No.: 15/774,795

(22) PCT Filed: Nov. 10, 2016

(86) PCT No.: PCT/IL2016/051215
§ 371 (c)(1),
(2) Date: May 9, 2018

(87) PCT Pub. No.: WO2017/081686
PCT Pub. Date: May 18, 2017

(65) Prior Publication Data
US 2018/0327753 A1    Nov. 15, 2018

Related U.S. Application Data

(60) Provisional application No. 62/253,142, filed on Nov. 10, 2015.

(51) Int. Cl.
| | | |
|---|---|---|
| C12N 15/11 | (2006.01) | |
| C12N 15/113 | (2010.01) | |
| C12Q 1/68 | (2018.01) | |
| C12Q 1/6886 | (2018.01) | |
| A61K 31/713 | (2006.01) | |
| A61P 35/00 | (2006.01) | |

(52) U.S. Cl.
CPC ........ *C12N 15/1138* (2013.01); *A61K 31/713* (2013.01); *A61P 35/00* (2018.01); *C12Q 1/68* (2013.01); *C12Q 1/6886* (2013.01); *C12N 2310/14* (2013.01); *C12Q 2600/118* (2013.01); *C12Q 2600/158* (2013.01)

(58) Field of Classification Search
CPC ........ A61P 35/00; A61P 35/04; C12N 15/111; C12N 15/113
See application file for complete search history.

(56) References Cited

U.S. PATENT DOCUMENTS

| | | |
|---|---|---|
| 3,687,808 A | 8/1972 | Merigan, Jr. |
| 4,469,863 A | 9/1984 | Ts o |
| 4,476,301 A | 10/1984 | Imbach |
| 4,873,316 A | 10/1989 | Meade |
| 5,023,243 A | 6/1991 | Tullis |
| 5,034,506 A | 7/1991 | Summerton |
| 5,166,315 A | 11/1992 | Summerton |
| 5,177,196 A | 1/1993 | Meyer, Jr. |
| 5,185,444 A | 2/1993 | Summerton |
| 5,188,897 A | 2/1993 | Suhadolnik |
| 5,214,134 A | 5/1993 | Weis |
| 5,216,141 A | 6/1993 | Benner |
| 5,235,033 A | 8/1993 | Summerton |
| 5,264,423 A | 11/1993 | Cohen |
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,321,131 A | 6/1994 | Agrawal |
| 5,399,676 A | 3/1995 | Froehler |
| 5,405,938 A | 4/1995 | Summerton |
| 5,405,939 A | 4/1995 | Suhadolnik |
| 5,434,257 A | 7/1995 | Matteucci |
| 5,453,496 A | 9/1995 | Caruthers |
| 5,455,233 A | 10/1995 | Spielvogel |
| 5,464,764 A | 11/1995 | Capecchi |
| 5,466,677 A | 11/1995 | Baxter |
| 5,470,967 A | 11/1995 | Huie |
| 5,476,925 A | 12/1995 | Letsinger |
| 5,487,992 A | 1/1996 | Capecchi |
| 5,489,677 A | 2/1996 | Sanghvi |
| 5,519,126 A | 5/1996 | Hecht |
| 5,536,821 A | 7/1996 | Agrawal |
| 5,539,082 A | 7/1996 | Nielsen |
| 5,541,306 A | 7/1996 | Agrawal |
| 5,541,307 A | 7/1996 | Cook |
| 5,550,111 A | 8/1996 | Suhadolnik |
| 5,561,225 A | 10/1996 | Maddry |
| 5,563,253 A | 10/1996 | Agrawal |
| 5,571,799 A | 11/1996 | Tkachuk |
| 5,587,361 A | 12/1996 | Cook |

(Continued)

FOREIGN PATENT DOCUMENTS

| | | |
|---|---|---|
| EP | 0 264 166 A1 | 4/1988 |
| EP | 0 375 408 A1 | 6/1990 |

(Continued)

OTHER PUBLICATIONS

Sung et al., Characterization of a stem cell population in lung cancer A549 cells, BBRC, vol. 371, pp. 163-167. (Year: 2008).*

(Continued)

*Primary Examiner* — Dana H Shin
(74) *Attorney, Agent, or Firm* — J.A. Lindeman & Co., PLLC

(57) ABSTRACT

Provided are RNA inhibitory molecules, particularly siRNA molecules silencing the expression of Voltage-Dependent Ion Chanel-1 (VDAC1) for the induction of cancer stem cell differentiation and reduction of TAMs abundance and tumor angiogenesis, thereby preventing tumor invention and recurrence.

3 Claims, 22 Drawing Sheets

Specification includes a Sequence Listing.

(56) References Cited

U.S. PATENT DOCUMENTS

| | | | |
|---|---|---|---|
| 5,596,086 | A | 1/1997 | Matteucci |
| 5,602,240 | A | 2/1997 | Mesmaeker |
| 5,608,046 | A | 3/1997 | Cook |
| 5,610,289 | A | 3/1997 | Cook |
| 5,618,704 | A | 4/1997 | Sanghvi |
| 5,623,070 | A | 4/1997 | Cook |
| 5,625,050 | A | 4/1997 | Beaton |
| 5,633,360 | A | 5/1997 | Bischofberger |
| 5,656,611 | A | 8/1997 | Kabanov |
| 5,663,312 | A | 9/1997 | Chaturvedula |
| 5,677,437 | A | 10/1997 | Teng |
| 5,677,439 | A | 10/1997 | Weis |
| 5,714,331 | A | 2/1998 | Buchardt |
| 5,719,262 | A | 2/1998 | Buchardt |
| 5,721,138 | A | 2/1998 | Lawn |
| 5,753,613 | A | 5/1998 | Ansell |
| 5,780,235 | A | 7/1998 | Bandman |
| 5,785,992 | A | 7/1998 | Ansell |
| 6,120,798 | A | 9/2000 | Allen |
| 6,221,959 | B1 | 4/2001 | Kabanov |
| 6,303,374 | B1 | 10/2001 | Zhang |
| 6,326,174 | B1 | 12/2001 | Joyce |
| 6,346,613 | B1 | 2/2002 | O'Mahony |
| 6,353,055 | B1 | 3/2002 | Kabanov |
| 7,608,259 | B2 | 10/2009 | Bergstein |
| 7,615,554 | B2 | 11/2009 | Selliah |
| 7,691,997 | B2 | 4/2010 | Khvorova |
| 8,093,369 | B2 | 1/2012 | Shoshan-Barmatz |
| 8,129,184 | B2 | 3/2012 | Yu |
| 8,846,633 | B2 | 9/2014 | Chiou |
| 9,078,857 | B2 | 7/2015 | Vescovi |
| 2002/0123476 | A1 | 9/2002 | Emanuele |
| 2002/0128218 | A1 | 9/2002 | Emanuele |
| 2003/0096980 | A1 | 5/2003 | Froehler |
| 2003/0170680 | A1 | 9/2003 | Froehler |
| 2004/0161777 | A1 | 8/2004 | Baker |
| 2004/0171003 | A1 | 9/2004 | Yoshikawa |
| 2006/0204982 | A1 | 9/2006 | Morris |
| 2006/0211683 | A1 | 9/2006 | Selliah |
| 2007/0135372 | A1 | 6/2007 | MacLachlan |
| 2008/0274962 | A1 | 11/2008 | Shoshan-Barmatz |
| 2011/0177032 | A1* | 7/2011 | Martuza ............... C12N 7/00 424/93.2 |
| 2011/0251082 | A1 | 10/2011 | Chan |
| 2011/0275083 | A1 | 11/2011 | Kiefer |
| 2012/0164730 | A1* | 6/2012 | Shoshan-Barmatz ....... C12N 15/1138 435/375 |
| 2013/0209413 | A1 | 8/2013 | Rommelaere |
| 2014/0377263 | A1 | 12/2014 | Lieberman |
| 2015/0315589 | A1 | 11/2015 | Smith Resar |

FOREIGN PATENT DOCUMENTS

| | | |
|---|---|---|
| WO | 03/031650 A2 | 4/2003 |
| WO | 2004/045543 A2 | 6/2004 |
| WO | 2006/095347 A2 | 9/2006 |
| WO | 2007043049 A1 | 4/2007 |
| WO | 2013/012806 A2 | 1/2013 |
| WO | 2013036867 A2 | 3/2013 |

OTHER PUBLICATIONS

Yao et al., Glioblastoma stem cells produce vascular endothelial growth factor by activation of a G-protein coupled formylpeptide receptor FPR, Journal of Pathology, vol. 215, pp. 369-376. (Year: 2008).*

Andey et al., Cationic lipid guided short-hairpin RNA interference of annexin A2 attenuates tumor growth and metastasis in a mouse lung cancer stem cell model, Journal of Controlled Release, vol. 184, pp. 67-78. (Year: 2014).*

Low et al., Knockdown of ubiquitin ligases in glioblastoma cancer stem cells leads to cell death and differentiation, Journal of Biomolecular Screening, vol. 17, pp. 152-162. (Year: 2012).*

Vlashi et al., Metabolic state of glioma stem cells and nontumorigenic cells, PNAS, vol. 108, p. 16062-16067. (Year: 2011).*

Zaid et al., (2005) The voltage-dependent anion channel-1 modulates apoptotic cell death. Cell Death Differ 12(7): 751-760.

Ambion TechNotes 9(5): "More siRNA Vectors for RNA interference", Oct. 2002, accessed http://www.ambion.com/techlib/tn/95/952.html on Apr. 22, 2008, 4 print-out pages.

GSE73243; Expression data from U87 xenograft tissues. Retrieved from: https://www.ncbi.nlm.nih.gov/geo/query/acc.cgi?acc=GSE73243, on Nov. 11, 2018; 2 pages.

NP_003365; voltage-dependent anion-selective channel protein 1 [Homo sapiens]. Retrieved from: https://www.ncbi.nlm.nih.gov/protein/NP_003365, on Nov. 11, 2018; 5 pages.

"PSUPER.retro.puro:Manual", A vector system for expression of short interfering RNA, 2004, OligoEngine, Inc.

Abu-Hamad et al., (2006) The expression level of the voltage-dependent anion channel controls life and death of the cell. Proc Natl Acad Sci USA 103(15): 5787-5792.

Agiostratidou et al., (2007) Differential cadherin expression: potential markers for epithelial to mesenchymal transformation during tumor progression. J Mammary Gland Biol Neoplasia 12(2-3): 127-133.

Agnihotri et al., (2016) Metabolic reprogramming in glioblastoma: the influence of cancer metabolism on epigenetics and unanswered questions. Neuro Oncol 18(2): 160-172.

Arif et al., (2014) Silencing VDAC1 Expression by siRNA Inhibits Cancer Cell Proliferation and Tumor Growth in Vivo. Mol Ther Nucleic Acids 3: e159; 14 pages.

Arif et al., (2016) Reducing VDAC1 expression induces a non-apoptotic role for pro-apoptotic proteins in cancer cell differentiation. Biochim Biophys Acta 1857(8): 1228-1242.

Arif et al., (2017) VDAC1 is a molecular target in glioblastoma, with its depletion leading to reprogrammed metabolism and reversed oncogenic properties. Neuro Oncol 19(7): 951-964.

Ashburner et al., (2000) Gene ontology: tool for the unification of biology. The Gene Ontology Consortium. Nat Genet 25(1): 25-29.

Auffinger et al., (2014) Conversion of differentiated cancer cells into cancer stem-like cells in a glioblastoma model after primary chemotherapy. Cell Death 21(7): 1119-1131.

Bai et al., (2011) Molecular targeting of glioblastoma: Drug discovery and therapies. Trends Mol Med 17(6): 301-312.

Banerji et al., (1983) A lymphocyte-specific cellular enhancer is located downstream of the joining region in immunoglobulin heavy chain genes. Cell 33(3): 729-740.

Bao et al., (2006) Glioma stem cells promote radioresistance by preferential activation of the DNA damage response. Nature 444(7120): 756-760.

Barriere et al., (2014) Circulating tumor cells and epithelial, mesenchymal and sternness markers: characterization of cell subpopulations. Ann Transl Med 2(11): 109; 8 pages.

Beal et al., (1991) Second structural motif for recognition of DNA by oligonucleotide-directed triple-helix formation. Science 251(4999): 1360-1363.

Besch et al., (2002) Specific inhibition of ICAM-1 expression mediated by gene targeting with Triplex-forming oligonucleotides. J Biol Chem 277(36): 32473-32479.

Binello et al., (2012) Stem cells as therapeutic vehicles for the treatment of high-grade gliomas. Neuro Oncol 14(3): 256-265.

Blachly-Dyson et al., (1993) Cloning and functional expression in yeast of two human isoforms of the outer mitochondrial membrane channel, the voltage-dependent anion channel. J Biol Chem 268(3): 1835-1841.

Blachly-Dyson et al., (1994) Human genes encoding the voltage-dependent anion channel (VDAC) of the outer mitochondrial membrane: mapping and identification of two new isoforms. Genomics 20(1): 62-67.

Breaker et al., (1995) A DNA enzyme with Mg(2+)-dependent RNA phosphoesterase activity. Chem Biol 2(10): 655-660.

Britto et al., (2007) Shift in AP-2alpha localization characterizes astrocytoma progression. Cancer Biol Ther 6(3): 413-418.

(56) References Cited

OTHER PUBLICATIONS

Byrne et al., (1989) Multiplex gene regulation: a two-tiered approach to transgene regulation in transgenic mice. Proc Natl Acad Sci U S A 86(14): 5473-5477.
Calame et al., (1988) Transcriptional controlling elements in the immunoglobulin and T cell receptor loci. Adv Immunol 43: 235-275.
Camporeale et al., (2014) STAT3 Activities and Energy Metabolism: Dangerous Liaisons. Cancers (Basel) 6(3): 1579-1596.
Carbone et al., (2003) Selective inhibition of transcription of the Ets2 gene in prostate cancer cells by a triplex-forming oligonucleotide. Nucleic Acids Res 31(3): 833-843.
Chattopadhyay et al., (2009) Molecular profiling to identify molecular mechanism in esophageal cancer with familial clustering. Oncol Rep 21(5): 1135-1146.
Chen et al., (2012) A restricted cell population propagates glioblastoma growth after chemotherapy. Nature 488(7412): 522-526.
Cogoi et al., (2010) The KRAS promoter responds to Myc-associated zinc finger and poly(ADP-ribose) polymerase 1 proteins, which recognize a critical quadruplex-forming GA-element. J Biol Chem 285(29): 22003-22016.
Cooney et al., (1988) Site-specific oligonucleotide binding represses transcription of the human c-myc gene in vitro. Science 241(4864): 456-459.
Czauderna et al., (2003) Structural variations and stabilising modifications of synthetic siRNAs in mammalian cells. Nucleic Acids Res 31(11): 2705-2716.
Das et al., (2014) Assessment of drug delivery and anticancer potentials of nanoparticles-loaded siRNA targeting STAT3 in lung cancer, in vitro and in vivo. Toxicol Lett 225(3): 454-466.
de la Iglesia et al., (2008) Identification of a PTEN-regulated STAT3 brain tumor suppressor pathway. Genes Dev 22(4): 449-462.
Dirks (2010) Brain tumor stem cells: the cancer stem cell hypothesis writ large. Mol Oncol 4(5): 420-430.
Edlund et al., (1985) Cell-specific expression of the rat insulin gene: evidence for role of two distinct 5' flanking elements. Science 230(4728): 912-916.
Elbashir et al., (2002) Analysis of gene function in somatic mammalian cells using small interfering RNAs. Methods 26(2): 199-213.
Englisch et al., (1991) Chemically Modified Oligonucleotides as Probes and Inhibitors. Angew Chem Int Ed Engl 30: 613-629.
Feichtinger et al., (2014) Alterations of oxidative phosphorylation complexes in astrocytomas. Glia 62(4): 514-525.
Fessi et al., (1989) Nanocapsule formation by interfacial polymer deposition following solvent displacement. International Journal of Pharmaceutics 55(1): R1-R4.
Gilboa et al., (1986) Transfer and expression of cloned genes using retroviral vectors. BioTechniques 4(6): 504-512.
Glass et al., (2014) CNS macrophages and peripheral myeloid cells in brain tumours. Acta Neuropathol 128(3): 347-362.
Gomez et al., (2014) Suppression of microRNA-9 by mutant EGFR signaling upregulates FOXP1 to enhance glioblastoma tumorigenicity. Cancer Res 74(5): 1429-1439.
Gonzalez-Gronow et al., (2003) The voltage-dependent anion channel is a receptor for plasminogen kringle 5 on human endothelial cells. J Biol Chem 278(29): 27312-27318.
Hamada et al., (2002) Effects on RNA interference in gene expression (RNAi) in cultured mammalian cells of mismatches and the introduction of chemical modifications at the 3'-ends of siRNAs. Antisense Nucleic Acid Drug Dev 12(5): 301-309.
Hanahan et al., (2011) Hallmarks of cancer: the next generation. Cell 144(5): 646-674.
Hattermann et al., (2016) Stem cell markers in glioma progression and recurrence. Int J Oncol 49(5): 1899-1910.
Huang et al., (2009) Bioinformatics enrichment tools: paths toward the comprehensive functional analysis of large gene lists. Nucleic Acids Res 37(1): 1-13.
Itoh et al., (2002) Inhibition of Urokinase Receptor (uPAR) Expression by RNA-Cleaving Catalytic DNA (DNAzyme) Containing Antisense uPAR. Mol Ther 5(5 Pt 2): S134; abstract No. 409.

Iwatsuki et al., (2010) Epithelial-mesenchymal transition in cancer development and its clinical significance. Cancer Sci 101(2): 293-299.
Katoh et al., (2013) Cancer genetics and genomics of human FOX family genes. Cancer Lett 328(2): 198-206.
Khachigian (2002) DNAzymes: cutting a path to a new class of therapeutics. Curr Opin Mol Ther 4(2): 119-121.
Koppenol et al., (2011) Otto Warburg's contributions to current concepts of cancer metabolism. Nat Rev Cancer 11(5): 325-337.
Koren et al., (2010) Downregulation of voltage-dependent anion channel-1 expression by RNA interference prevents cancer cell growth in vivo. Cancer Biol Ther 9(12): 1046-1052.
Lawen et al., (2005) Voltage-dependent anion-selective channel 1 (VDAC1)—a mitochondrial protein, rediscovered as a novel enzyme in the plasma membrane. Int J Biochem Cell Biol 37(2): 277-282.
Li et al., (2006) A proteomic investigation into a human gastric cancer cell line BGC823 treated with diallyl trisulfide. Carcinogenesis 27(6): 1222-1231.
Li et al., (2014) Plasminogen kringle 5 induces endothelial cell apoptosis by triggering a voltage-dependent anion channel 1 (VDAC1) positive feedback loop. J Biol Chem 289(47): 32628-32638.
Liang et al., (2004) High efficiency gene transfer into mammalian kidney cells using baculovirus vectors. Arch Virol 149(1): 51-60.
Liu et al., (2006) Increased susceptibility to apoptosis in CD45(+) myeloma cells accompanied by the increased expression of VDAC1. Oncogene 25(3): 419-429.
Lunyak et al., (2005) No rest for REST: REST/NRSF regulation of neurogenesis. Cell 121(4): 499-501.
Maher et al., (1989) Inhibition of DNA binding proteins by oligonucleotide-directed triple helix formation. Science 245(4919): 725-730.
Maldonado et al., (2012) Warburg revisited: regulation of mitochondrial metabolism by voltage-dependent anion channels in cancer cells. J Pharmacol Exp Ther 342(3): 637-641.
Mani et al., (2008) The epithelial-mesenchymal transition generates cells with properties of stem cells. Cell 133(4): 704-715.
Mello et al., (2004) Revealing the world of RNA interference. Nature 431(7006): 338-342.
Moser et al., (1987) Sequence-specific cleavage of double helical DNA by triple helix formation. Science 238(4827): 645-650.
Nathanson et al., (2014) Targeted therapy resistance mediated by dynamic regulation of extrachromosomal mutant EGFR DNA. Science 343(6166): 72-76.
Noy et al., (2014) Tumor-associated macrophages: from mechanisms to therapy. Immunity 41(1): 49-61.
Orso et al., (2007) The AP-2alpha transcription factor regulates tumor cell migration and apoptosis. Adv Exp Med Biol 604: 87-95.
Peng (2008) Stable RNA interference of hexokinase II gene inhibits human colon cancer LoVo cell growth in vitro and in vivo. Cancer Biol Ther 7(7): 1128-1135.
Pinkert et al., (1987) An albumin enhancer located 10 kb upstream functions along with its promoter to direct efficient, liver-specific expression in transgenic mice. Genes Dev 1(3): 268-276.
Pollard et al., (2009) Glioma stem cell lines expanded in adherent culture have tumor-specific phenotypes and are suitable for chemical and genetic screens. Cell Stem Cell 4(6): 568-580.
Puri et al., (2001) Targeted gene knockout by 2'-O-aminoethyl modified triplex forming oligonucleotides. J Biol Chem 276(31): 28991-28998.
Rahmathulla et al., (2013) Bevacizumab in high-grade gliomas: a review of its uses, toxicity assessment, and future treatment challenges. Onco Targets Ther 6: 371-389.
Reither et al., (2002) Specificity of DNA triple helix formation analyzed by a FRET assay. BMC Biochem 3: 27; 9 pages.
Ricci et al., (2003) Mitochondrial functions during cell death, a complex (I-V) dilemma. Cell Death Differ 10(5): 488-492.
Rostovtseva et al., (1998) ATP transport through a single mitochondrial channel, VDAC, studied by current fluctuation analysis. Bopphys J 74(5): 2365-2373.
Rota et al., (2012) Determining mammosphere-forming potential: application of the limiting dilution analysis. J Mammary Gland Biol Neoplasia 17(2): 119-123.

(56) References Cited

OTHER PUBLICATIONS

Safa et al., (2015) Glioblastoma stem cells (GSCs) epigenetic plasticity and interconversion between differentiated non-GSCs and GSCs. Genes Dis 2(2): 152-163.
Santoro et al., (1997) A general purpose RNA-cleaving DNA enzyme. Proc Natl Acad Sci U S A 94(9): 4262-4266.
Seidman et al., (2003) The potential for gene repair via triple helix formation. J Clin Invest 112(4): 487-494.
Shinohara et al., (2000) Characterization of porin isoforms expressed in tumor cells. Eur J Biochem 267(19): 6067-6073.
Shiras et al., (2003) A unique model system for tumor progression in GBM comprising two developed human neuro-epithelial cell lines with differential transforming potential and coexpressing neuronal and glial markers. Neoplasia 5(6): 520-532.
Shoshan-Barmatz et al., (2010) VDAC, a multi-functional mitochondrial protein regulating cell life and death. Mol Aspects Med 31(3): 227-285.
Shoshan-Barmatz et al., (2015) The mitochondrial voltage-dependent anion channel 1 in tumor cells. Biochim Biophys Acta 1848(10 Pt B): 2547-2575.
Shoshan-Barmatz, (2016) Targeting VDAC1: From concepts to cancer therapy. Biochimica et Biophysica Acta (BBA)—Bioenergetics 1857 (Supplement): e18.
Singh et al., (2004) Identification of human brain tumour initiating cells. Nature 432(7015): 396-401.
Soreq et al., (1974) In vitro translation of polyadenylic acid-free rabbit globin messenger RNA. J Mol Biol 88(1): 233-245.
Sottoriva et al., (2013) Intratumor heterogeneity in human glioblastoma reflects cancer evolutionary dynamics. Proc Natl Acad Sci U S A 110(10): 4009-4014.
Sun et al., (2006) Mechanisms controlling embryonic stem cell self-renewal and differentiation. Crit Rev Eukaryot Gene Expr 16(3): 211-232.
Tejeddine et al., (2008) Hierarchical involvement of Bak, VDAC1 and Bax in cisplatin-induced cell death. Oncogene 27(30): 4221-4232.
Tempel-Brami et al., (2015) Practical Applications of in Vivo and ex Vivo MRI in Toxicologic Pathology Using a Novel High-performance Compact MRI System. Toxicol Pathol 43(5): 633-650.
Tonkinson et al., (1996) Antisense oligodeoxynucleotides as clinical therapeutic agents. Cancer Invest 14(1): 54-65.
Ulitsky et al., (2010) Expander: from expression microarrays to networks and functions. Nat Protoc 5(2): 303-322.
Vasquez et al., (1999) Chromosomal mutations induced by triplex-forming oligonucleotides in mammalian cells. Nucleic Acids Res 27(4): 1176-1181.
Vuyisich et al., (2000) Regulation of the RNA-dependent protein kinase by triple helix formation. Nucleic Acids Res 28(12): 2369-2374.
Wang et al., (2013) Regulation of neural stem cell differentiation by transcription factors HNF4-1 and MAZ-1. Mol Neurobiol 47(1): 228-240.
Watt et aL, (2003) HNF4: a central regulator of hepatocyte differentiation and function. Hepatology 37(6): 1249-1253.
Welch et al., (1998) Ribozyme gene therapy for hepatitis C virus infection. Clin Diagn Virol 10(2-3): 163-171.
Welch et al., (1998) Expression of ribozymes in gene transfer systems to modulate target RNA levels. Curr Opin Biotechnol 9(5): 486-496.
Wiese et al., (2012) Astrocytes as a source for extracellular matrix molecules and cytokines. Front Pharmacol 3: 120; 13 pages.
Winoto et al., (1989) A novel, inducible and T cell-specific enhancer located at the 3' end of the T cell receptor alpha locus. EMBO J 8(3): 729-733.
Yan et al., (2011) A CD133-related gene expression signature identifies an aggressive glioblastoma subtype with excessive mutations. Proc Natl Acad Sci U S A 108(4): 1591-1596.
Yeung et al., (2008) Roles of p53, MYC and HIF-1 in regulating glycolysis—the seventh hallmark of cancer. Cell Mol Life Sci 65(24): 3981-3999.
Zabala et al., (2004) Optimization of the Tet-on system to regulate interleukin 12 expression in the liver for the treatment of hepatic tumors. Cancer Res 64(8): 2799-2804.
Peiris-Pagés et al., (2016) Cancer stem cell metabolism. Breast Cancer Res 18(1): 55; 10 pages.
Arif et al., "Mitochondrial VDAC1 Silencing Leads to Metabolic Rewiring and the Reprogramming of Tumor Cells into Advanced Differentiated States", Cancer, 2018, 10, 499, pp. 1-26.
Arif et al., "Metaolic Reprogramming via Silencing of Mitochondrial VDAC1 Expression Encourages Differentiation of Cancer Cells", Molecular Therapy: Nucleic Acids vol. 17, 2019, pp. 24-37.

\* cited by examiner

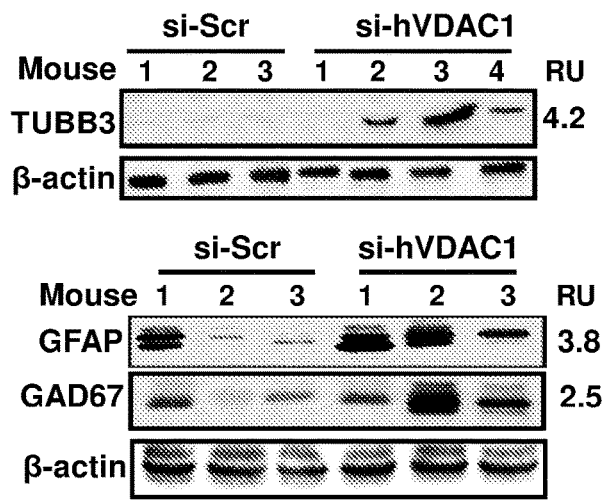
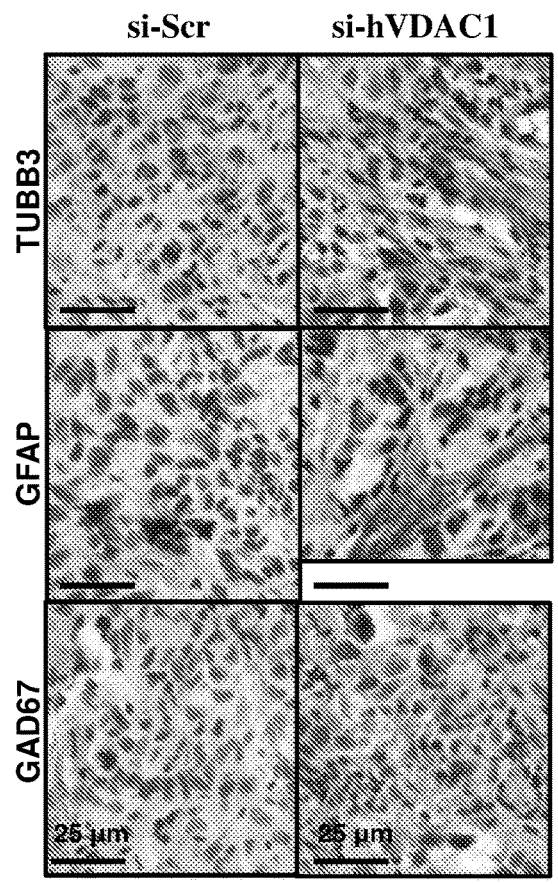
Fig. 2A
Fig. 2B
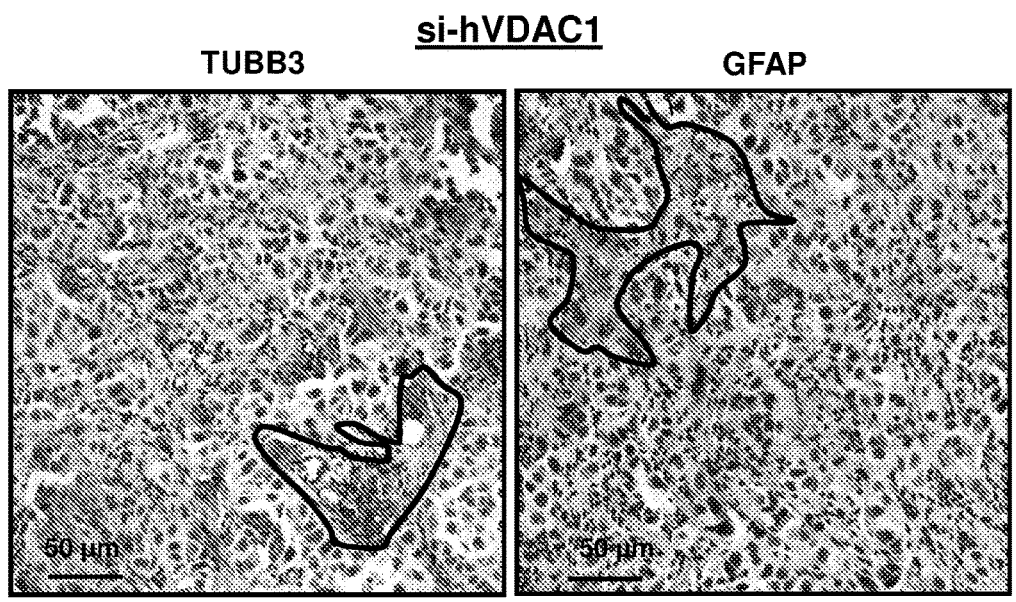
Fig. 2C

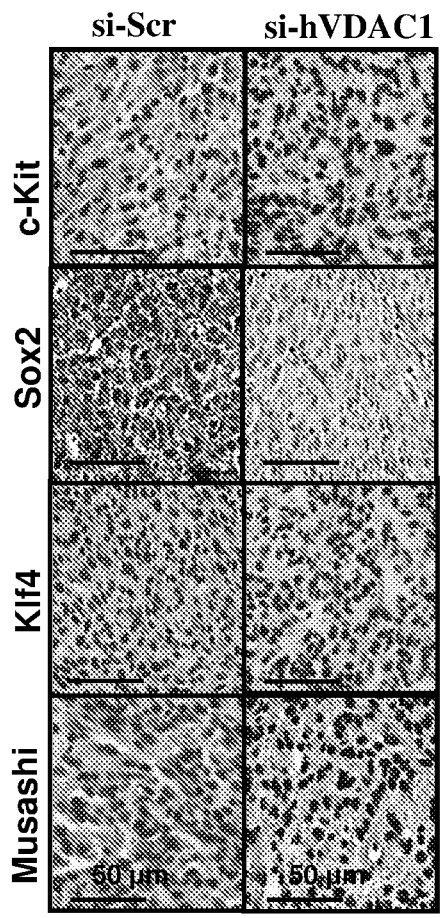
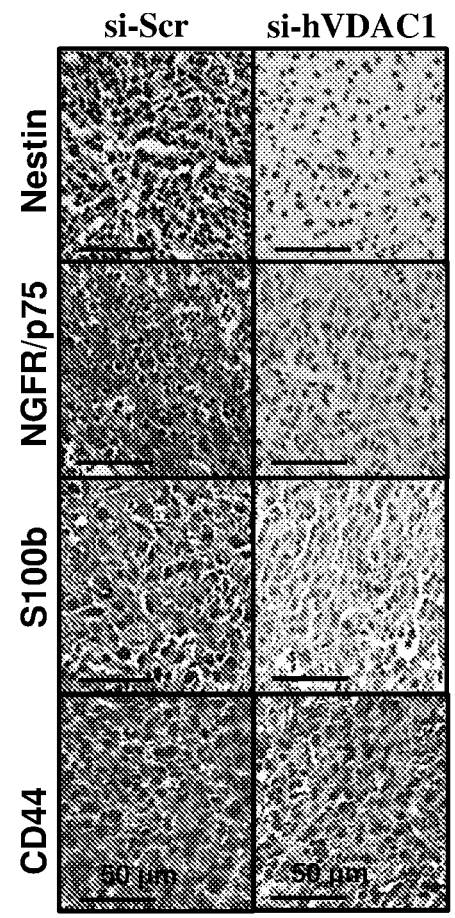
Fig. 3E
Fig. 3F

Fig. 7J si-Scr-treated U-87MG cells
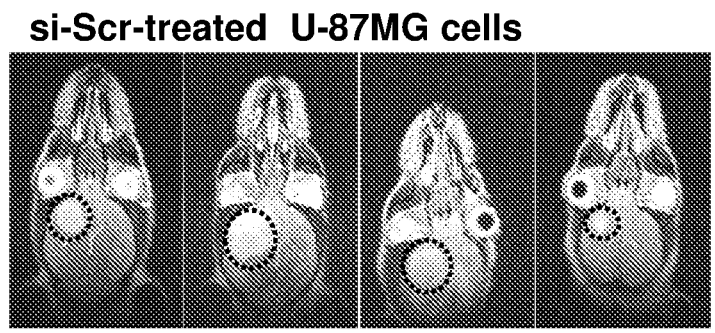
si-hVDAC1-treated U-87MG cells
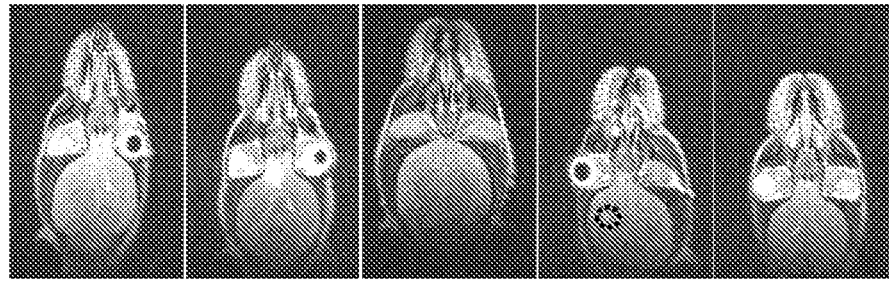
Fig. 7K
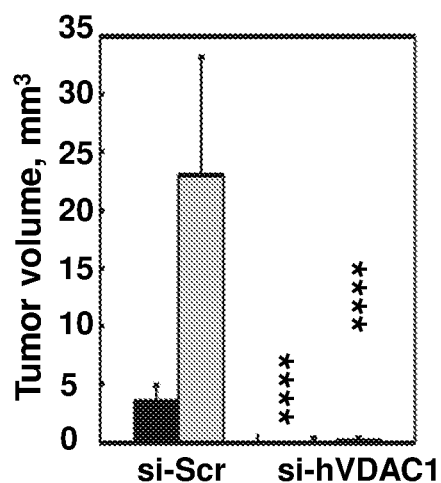
Fig. 7L
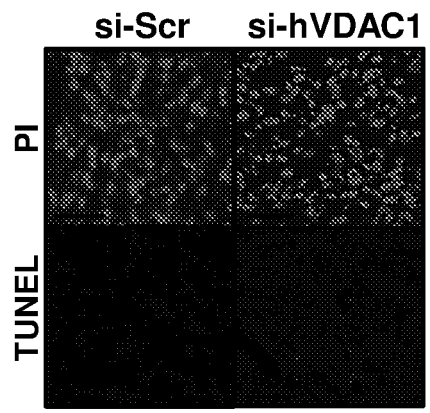

MEANS AND METHODS FOR REDUCING TUMORIGENICITY OF CANCER STEM CELLS

SEQUENCE LISTING

The Sequence Listing submitted in text format (.txt) filed on May 9, 2018, named "SequenceListing.txt", created on May 8, 2018 (21.4 KB), is incorporated herein by reference.

FIELD OF THE INVENTION

The present invention relates to means and methods for inhibiting the tumorigenicity of cancer and cancer stem cells. Particularly, the present invention discloses the use of RNA inhibitory molecules, particularly siRNAs silencing the expression of Voltage-Dependent Ion Chanel-1 (VDAC1) for the induction of cancer stem cell differentiation, reduction of tumor epithelial mesenchymal transition (EMT), tumor associated angiogenesis and tumor associated macrophages (TAMs) associated with tumor microenvironment, thereby preventing tumor progression, invasion and recurrence.

BACKGROUND OF THE INVENTION

Accumulating evidence suggests that many cancers are maintained in a hierarchical organization of rare, slowly dividing tumor-initiating cells, also termed cancer stem cells; rapidly dividing amplifying cells (precursor cells); and differentiated tumor cells. Cancer stem cells (CSCs) are found within tumors or hematological cancers and possess characteristics normally associated with normal stem cells such as self-renewal and the ability to differentiate into multiple cell types. CSCs persist in tumors as a distinct population and give rise to the quasi (not finally) differentiated and differentiated cells that form the bulk of the tumor mass and phenotypically characterize the disease. These cells have been demonstrated to be highly tumorigenic and to be fundamentally responsible for cancer metastasis and cancer recurrence. There is mounting evidence that such cells exist in almost all tumor types, but their number is significantly lower compared to the number of the bulk cancer cells. CSCs are also often called tumor initiating cells, cancer stem-like cells, stem-like cancer cells, highly tumorigenic cells, or super malignant cells.

The cancer stem cells are generally slow-growing and transiently quiescent thus are not responsive to traditional anti-cancer therapies targeted to fast-growing cells. Therefore, traditional cancer therapies are likely to inhibit the bulk tumor population but not cancer stem cells, leaving the cancer stem cells intact and able to give rise to tumor re-growth. Consequently, cancer may recur as the result of cancer stem cell-driven expansion.

The existence of cancer stem cells has several implications in terms of cancer treatment and therapy. These include disease identification, selective drug targets, prevention of cancer metastasis and recurrence, treatment of cancer refractory to chemotherapy and/or radiotherapy, treatment of cancers inherently resistant to chemotherapy or radiotherapy and development of new strategies in fighting cancer.

Gliomas are the most common brain tumors, and, in particular, grade IV glioma, also named glioblastoma multiforme (GBM), represents the most severe type. This highly aggressive tumor is associated with high rates of morbidity, relapse and mortality (Bai R Y et al., 2011. Trends in molecular medicine 17, 301-312). GBM is a heterogeneous cancer, with tumors containing niches enriched for transiently quiescent and self-renewing cells that are essentially GBM cancer stem cells (GSCs) (Chen J et at, 2012. Nature 488, 522-526). Such intra-tumoral heterogeneity underlies the inability of conventional and targeted therapies to achieve long-term remission (Nathanson D A et al., 2014. Science 343, 72-76; Sottoriva A et al., 2013. PNAS USA 110, 4009-4014).

Cancer cells acquire a common set of properties, including high proliferation, resistance to apoptosis and metabolic reprogramming, such as enhanced anaerobic glycolysis (Warburg effect; Hanahan, D, and Weinberg, R A 2011. Cell 144, 646-674; Koppenol W H et al. 2011. Nature reviews Cancer 11, 325-337). As such, cancer cells up-regulate the transcription of genes related to glycolysis. Mitochondria play a role in reprogramming cellular metabolism, with metabolic flexibility serving to balance tumor cell energy needs with requirements for metabolites and precursors. Metabolic reprogramming in GBM and its influence on epigenetics were recently reviewed (Agnihotri, S and Zadeh G 2016. Neuro Oncol 18, 160-172).

Discovery of CSCs in glioblastoma as well as in other cancer types has opened a new target for treatment. For example, U.S. Pat. No. 7,608,259 discloses improved methods for treatment of cancer which involve the targeting of slow-growing, relatively mutationally-spared cancer stem line U.S. Pat. No. 8,129,184 discloses methods and compositions for cancer vaccines that target cancer stem cells. Particularly the invention discloses stimulating the immune response by administering to a patient a composition including dendritic cells that present cancer stem cell antigens. The method is used for treating cancer, glioblastoma being a specific embodiment.

U.S. Pat. No. 8,846,633 discloses a method for inhibiting cancer stem cell like properties and chemo-radio-resistant properties of cancer or tumor cells comprising delivering miR145 to the cancer or tumor cells, particularly brain tumor and head and neck cancer cells. The invention further provides a pharmaceutical composition comprising miR145 and a method for treating brain tumor and/or head and neck cancer comprising administration of miR145 to a subject in need thereof.

U.S. Pat. No. 9,078,857 discloses compositions comprising inhibitors of Ephrin (EPH) receptor expression in tumor stem cells and methods of use thereof for treating cancer.

U.S. Patent Application Publication No. 2013/0209413 discloses use of a parvovirus, preferably H-1PV, for the therapeutic elimination of cancer stem cells (CSCs), preferably neuroblastoma stem cells and glioblastoma stem cells.

U.S. Patent Application Publication No. 2014/0377263 discloses a method of treating and/or preventing cancer comprising targeting cancer stem cells by administering miRNAs which have reduced expression or are lacking in the cancer stem cells. In some embodiments, the miRNAs that are reduced or lacking in cancer stem cells are let-7 miRNAs. In alternative embodiments, the invention discloses a method of treating and/or preventing cancer comprising targeting cancer stem cells by administering miRNAs which have increased expression levels in the cancer stem cells.

Voltage-dependent anion channel 1 (VDAC1) is a mitochondrial protein controlling cell energy and metabolic homeostasis (Shoshan-Barmatz V et al., 2015; Biochim. Biophys. Acta 1848, 2547-2575; Shoshan-Barmatz V et al., 2010. Molecular aspects of medicine 31, 227-285). VDAC1 is the sole channel located at the outer mitochondrial membrane (OMM) mediating metabolic cross-talk between mitochondria and the cytosol, transporting metabolites, ions, nucleotides, $Ca^{2+}$ and more, thus regulating mitochondrial activity. VDAC1 also plays a key role in apoptosis, participating in the release of apoptotic factors from mitochondria and interacting with anti-apoptotic regulators (Shoshan-Barmatz et al., 2015, ibid; Shoshan-Barmatz et al., 2010, ibid). VDAC1 is also highly expressed in different tumors (Shoshan-Barmatz et at, 2015 ibid), including astrocytic tumors (Feichtinger R G et al., 2014. Glia 62, 514-525), pointing to its significance in high energy-demanding cancer cells.

An inventor of the present invention and co-worker have demonstrated that abrogation of VDAC1 expression by 2'-O-Me-modified siRNA specific to human (h)VDAC1 reduced cellular ATP levels and cell growth and inhibited solid tumor development and growth in cervical and lung cancers (U.S. Pat. No. 8,093,369; Koren I et al., 2010. Cancer biology & therapy 9, 1046-1052; Arif T et al., 2014. Molecular therapy Nucleic acids 3, e159). As a key regulator of metabolic and energy reprogramming, disrupting cancer energy and metabolism homeostasis by targeting VDAC1 offers a potential anti-cancer therapy strategy (Maldonado E N and Lemasters J J. 2012. J Pharmacol Exp Ther 342, 637-641).

A paper of the present inventor and co-workers published after the priority date of the present invention descries that VDAC1 deletion led to up-regulation of pro-apoptotic proteins including caspases, p53 and Cytochrome c, yet without apoptosis induction. Rather, this up-regulation was associated with cell differentiation and down regulation of SMAC/Diablo, AIF and translocator protein (TSPO), all connected to cell growth support. (Arif T et al. 2016. Biochim Biophys Acta 1857(8), 1228-42). The results show that the activity of apoptotic proteins extends beyond the realm of cell death induction, revealing roles at the intersection between oncogene-induced changes in metabolism and the expression of pro-apoptotic proteins, to the benefit of the cancer cell.

Current approaches for tumor treatment many times do not prevent recurrence, particularly in certain cancer types including, for example, glioblastoma. Tumor recurrence is a major cause of mortality; thus, there is a great need for and it would be highly advantageous to have means to reduce tumorigenicity and cancer recurrence.

SUMMARY OF THE INVENTION

The present invention relates to the reduction of tumorigenicity of tumors comprising cancer stem cells, particularly to the prevention of the tumor recurrence, tumor cancer stem cell (CSC) invasion, tumor angiogenesis and tumor-favorable microenvironment, and to induction of tumor cancer stem cells differentiation leading to reduction in CSC.

The present invention is based in part on the unexpected discovery that silencing the expression of VDAC1 in human glioblastoma tumor cells had led to reprogramming of the glioblastoma stem cells towards differentiation into non-replicating end-stage mature-like neurons and astrocytes. Several markers associated with cancer stem cells were disappeared while markers of differentiated astrocytes and neuron-like cells appeared. The present invention now discloses hitherto unknown effects of silencing the expression of VDAC1 on several cancer-associated biological processes, including induction of cancer stem cells differentiation, reversing the epithelial to mesenchymal transition (EMT), reversing the reprogrammed cancer cell metabolism towards metabolism of healthy cells, reduced TAMs abundance and NF-kB expression as a pro-inflammatory marker and inhibition of angiogenesis.

Thus, the invention now provides means and methods for treating cancers that are characterized by the presence of cancer stem cells, particularly for preventing the recurrence of such cancers, for reducing tumor invasiveness and for reducing angiogenesis utilizing VDAC1-silencing oligonucleotides or recombinant constructs encoding same.

According to one aspect, the present invention provides a method of reducing the tumorigenicity of a tumor, the method comprises administering to, or expressing in cells of a subject affected with a tumor comprising cancer stem cells (CSCs) an effective amount of at least one voltage dependent anion channel 1 (VDAC1)-silencing oligonucleotide, thereby reducing the number and/or frequency of the CSCs in said tumor.

According to certain embodiments, the tumor is a solid tumor. According to some embodiments, the solid tumor is selected from the group consisting of brain, breast, prostate, cervical, ovary, pancreas, head and neck, sarcoma, lymphoma, melanoma and colon cancer. Each possibility represents a separate embodiment of the present invention. According to certain embodiments, the brain tumor is glioma. According to certain embodiments, the glioma is selected from the group consisting of astrocytoma, oligodendroglioma, and glioblastoma. According to certain exemplary embodiments, the glioma is glioblastoma multiforme (GBM; glioma stage IV).

According to certain embodiments, the tumor is a non-solid tumor. According to some embodiments, the non-solid tumor is blood cancer.

According to certain embodiments, the VDAC1-silencing oligonucleotide comprises at least 15 contiguous nucleic acids identical to the gene or mRNA encoding human VDAC1 protein or to a complementary polynucleotide thereof, wherein the human VDAC1 protein comprises the amino acid sequence set forth in SEQ ID NO:1.

According to certain embodiments the hVDAC1 protein is encoded by the nucleic acid sequence set forth in SEQ ID NO:2.

Any silencing oligonucleotide molecule as is known in the art can be used according to the teachings of the present invention as long as the oligonucleotide comprises at least 15 contiguous nucleic acids identical to SEQ ID NO:2, to an mRNA molecule encoded by same or to a sequence complementary thereto.

According to certain embodiments, the silencing oligonucleotide comprises a nucleic acid sequence selected from the group consisting of SEQ ID NO:3 (ACAC-UAGGCACCGAGAUUA); SEQ ID NO:4 (GGGCUAUG-GAUUUGGCUUA); SEQ ID NO:5 (GCUUGGUC-UAGGACUGGAA); SEQ ID NO:6 (AAGCUGACCUUCGAUUCAU); SEQ ID NO:7 (GAAUGACGGGACAGAGUUU); SEQ ID NO:8 (UCG-GAAUAGCAGCCAAGUA); SEQ ID NO:9 (CUC-UUCUGGAUGGCAAGAA); SEQ ID NO:10 (GAAUAGCAGCCAAGUAUCAG) and a complementary sequence thereto.

According to certain embodiments, the VDAC1-silencing oligonucleotide is selected from the group consisting of RNA interference (RNAi) molecule and antisense molecule. According to some embodiments, the RNAi molecule is an unmodified and/or modified double stranded (ds) RNA molecules including, but not limited to, short-temporal RNA (stRNA), small interfering RNA (siRNA), short-hairpin RNA (shRNA), and microRNA (miRNA).

According to certain exemplary embodiments, the RNAi is siRNA.

According to some exemplary embodiments, the siRNA comprises a first oligonucleotide sequence identical to at least 15 nucleotides of SEQ ID NO:2 or to a mRNA encoded by same and a second oligonucleotide sequence substantially complementary to the first oligonucleotide; wherein said first and second oligonucleotide sequences are annealed to each other to form the siRNA molecule.

According to some embodiments, the siRNA is a single-stranded short hairpin RNA (shRNA) wherein the first oligonucleotide sequence is separated from the second oligonucleotide sequence by a linker which forms a loop structure upon annealing of the first and second oligonucleotide sequences. In some embodiments the linker is about 3 to about 60 nucleotides.

According to some exemplary embodiments, the siRNA comprises a first oligonucleotide having the nucleic acid sequence set forth in SEQ ID NO:3 (ACACUAGGCACCGAGAUUA) and a second oligonucleotide having the nucleic acid sequence set forth in SEQ ID NO:94 (UAAUCUCGGUGCCUAGUGU).

According to some exemplary embodiments, the siRNA comprises a first oligonucleotide having the nucleic acid sequence set forth in SEQ ID NO:4 (GGGCUAUGGAUUUGGCUUA) and a second oligonucleotide having the nucleic acid sequence set forth in SEQ ID NO:11 (UAAGCCAAAUCCAUAGCCC).

According to some exemplary embodiments, the siRNA comprises a first oligonucleotide having the nucleic acid sequence set forth in SEQ ID NO:5 (GCUUGGUCUAGGACUGGAA) and a second oligonucleotide having the nucleic acid sequence set forth in SEQ ID NO:12 (UUCCAGUCCUAGACCAAGC).

According to some exemplary embodiments, the siRNA comprises a first oligonucleotide having the nucleic acid sequence set forth in SEQ ID NO:10 (GAAUAGCAGCCAAGUAUCAG) and a second oligonucleotide having the nucleic acid sequence set forth in SEQ ID NO:13 (UGAUACUUGGCUGCUAUUC).

According to additional embodiments, at least one of the siRNA nucleic acids is chemically modified. Typically, the modification is 2'-O-methyl modification of a guanine or uracil. According to certain embodiments, the first and the second polynucleotide of the RNAi comprise several chemically modified guanine and/or uracil nucleotides. According to certain exemplary embodiments, the modified siRNA molecule comprises a first oligonucleotide having the nucleic acid sequence set forth in SEQ ID NO:14 (ACACUAGGCACCGAGAUUA), wherein the Uracil and Guanine nucleotides marked in bold and underline comprise 2'-O-methyl modification and a second oligonucleotide having the nucleic acid sequence set forth in SEQ ID NO:15 (UAAUCUCGGUGCCUAGUGU, wherein the Uracil and Guanine nucleotides marked in bold and underline comprise 2'-O-methyl modification.

According to certain embodiments, the method comprises administering to the subject an isolated oligonucleotide silencing the expression of VDAC1. According to some embodiments, the method comprises administering to the subject an isolated oligonucleotide comprising a nucleic acid sequence selected from the group consisting of SEQ ID NOs:3-10. Each possibility represents a separate embodiment of the present invention. According to some embodiment, the method comprises administering to the subject an isolated siRNA molecule comprising the nucleic acid sequence set forth in any one of SEQ ID NOs:11-15 and 94.

According to certain exemplary embodiments, the method comprises administrating to the subject an isolated siRNA oligonucleotide comprises a first oligonucleotide having the nucleic acid sequence set forth in SEQ ID NO:3 and a second oligonucleotide having the nucleic acid sequence set forth in SEQ ID NO:94.

According to certain exemplary embodiments, the method comprises administrating to the subject an isolated siRNA oligonucleotide comprises a first oligonucleotide having the nucleic acid sequence set forth in SEQ ID NO:14 and a second oligonucleotide having the nucleic acid sequence set forth in SEQ ID NO:15.

According to certain embodiments, the method comprises administering to the subject a construct capable of expressing in cells of said subject a therapeutically effective amount of at least one VDAC1-silencing oligonucleotide. According to some embodiments, the method comprises administering to the subject a construct capable of expressing at least one oligonucleotide comprising a nucleic acid sequence selected from the group consisting of SEQ ID Nos:3-10. According to some embodiment, the method comprises administering to the subject a construct capable of expressing siRNA molecule comprising the nucleic acid sequence set forth in any one of SEQ ID Nos:11-15 and 94. According to certain exemplary embodiments, the method comprises administrating to the subject a construct capable of expressing siRNA oligonucleotide comprises a first oligonucleotide having the nucleic acid sequence set forth in SEQ ID NO:3 and a second oligonucleotide having the nucleic acid sequence set forth in SEQ ID NO:94. According to certain exemplary embodiments, the method comprises administrating to the subject a construct capable of expressing siRNA oligonucleotide comprises a first oligonucleotide having the nucleic acid sequence set forth in SEQ ID NO:14 and a second oligonucleotide having the nucleic acid sequence set forth in SEQ ID NO:15.

According to certain embodiments, reducing the tumorigenicity of the tumor comprises attenuating the invasive potential of said tumor, particularly of the tumor cancer stem cells. Without wishing to be bound by any specific theory or mechanism of action, reduction in the invasive potential of the tumor cells and/or the tumor cancer stem cells is attributed, inter alia, to the reversal of the epithelial to mesenchymal transition (EMT) process.

According to certain embodiments, reducing the tumorigenicity of the tumor comprises reducing the recurrence of said tumor.

According to additional aspect, the present invention provides a method for inducing the transition of a cancer stem cell to a differentiated cell, the method comprises administrating to or expressing in the cancer stem cell an effective amount of at least one voltage dependent anion channel 1 (VDAC1)-silencing oligonucleotide.

According to certain embodiments, the cancer stem cells are isolated cells present in a cell culture. According to other embodiments, the cancer stem cells are present within a tumor in a subject.

The VDAC1-silencing oligonucleotide and constructs comprising same are as described hereinabove.

As described in details in the examples section hereinbelow, the present invention discloses for the first time that silencing the expression of hVDAC1 by siRNA molecules had a significant impact on the expression of glioblastoma stem cells markers.

Thus, according to another aspect, the present invention provides a method for monitoring potential recurrence of glioblastoma in a subject, the method comprises determining the level of at least one marker selected from the group consisting of CD133, c-kit, Sox2, Klf4, Oct4, Nanog, Musashi, Nestin, NGFR, S100b, CD44 and any combination thereof in a sample comprising glioblastoma cancer cells obtained from the subject, wherein a level above a predetermined reference level correlates with a high potential of glioblastoma recurrence in said subject.

According to certain embodiments, the predetermined reference level is determined in a sample comprising corresponding glioblastoma cancer cells treated with an effective amount of VDAC1-silencing oligonucleotide molecule.

According to certain embodiments, the reference level is determined in a sample comprising glioblastoma cancer cells obtained from a tumor treated with the VDAC1-silencing molecule. According to other embodiments, the reference level is determined in a sample comprising cultured glioblastoma cancer cells treated with the VDAC1-silencing molecule. According to yet additional embodiments, the reference level is an average level of the at least one marker determined in samples obtained from healthy subjects.

The VDAC1 silencing oligonucleotide molecule is as described hereinabove.

According to yet additional aspect, the present invention provides a method for reducing angiogenesis in a tumor tissue, the method comprises administering to, or expressing in the tissue an effective amount of voltage dependent anion channel 1 (VDAC1)-silencing oligonucleotide molecule. The VDAC1 silencing oligonucleotide molecule and constructs comprising same are as described hereinabove.

According to yet additional aspect, the present invention provides a method for reducing tumor associated macrophages (TAMS) abundance in a tumor tissue, the method comprises administering to, or expressing in the tissue an effective amount of voltage dependent anion channel 1 (VDAC1)-silencing oligonucleotide molecule. The VDAC1 silencing oligonucleotide molecule or constructs comprising same are as described hereinabove.

According to yet additional aspect, the present invention discloses voltage dependent anion channel 1 (VDAC1)-silencing oligonucleotide or a construct comprising same for use in reducing the tumorigenicity of a tumor, wherein the tumor comprises cancer stem cells.

Any method as is known in the art for the administration of VDAC1 silencing oligonucleotide molecule, particularly VDAC1-directed siRNA or a construct comprising same can be used according to the teachings of the present invention.

According to certain embodiments, the VDAC1 silencing oligonucleotide molecule or a construct comprising same is administered within a pharmaceutical composition. According to certain exemplary embodiments, the pharmaceutical composition further comprises pharmaceutically acceptable excipients, diluents or carriers. According to additional exemplary embodiments, the VDAC1 silencing oligonucleotide molecule is encapsulated within a nanoparticle or a liposome. According to some embodiments, the VDAC1 silencing oligonucleotide molecule is encapsulated within Polyethylenimine (PEI)-Poly(D,L-lactide-co-glycolide) (PLGA) nanoparticle.

According to some embodiments, the VDAC1 silencing oligonucleotide molecule, construct comprising same or a composition comprising same is administered via intravenous, intradermal, intramuscular, intraarterial, intralesional, percutaneous, subcutaneous, intranasal or inhalation or by aerosol administration, or combinations thereof. In some embodiments, administration is prophylactic administration, and in alternative embodiments, administration is therapeutic administration.

According to certain embodiments, the subject is a mammal, particularly human According to some embodiments, the subject has previously undergone at least one or more cancer therapies including, but not limited to, surgery, chemotherapy, radiotherapy, thermotherapy, immunotherapy, hormone therapy and laser therapy.

Other objects, features and advantages of the present invention will become clear from the following description and drawings.

BRIEF DESCRIPTION OF THE FIGURES

FIG. 2 shows increased expression of differentiation markers in si-hVDAC1-TTs. FIG. 2A: Proteins extracted from si-Scr- or si-hVDAC1-TTs derived from U-118MG cells were immunoblotted for TUBB3, GFAP and GAD-67. β-actin immunostaining serving as a loading control is presented. RU=relative unit. FIG. 2B: IHC staining of si-Scr- or si-hVDAC1-TT sections from a U-118MG-derived tumor using specific antibodies against TUBB3, GFAP and GAD-67. FIG. 2C: The area circled by black lines indicates cells populations organized in clusters that may point to group of GSCs that undergo differentiation process.

FIG. 3A shows the change in the expression of stem cells TFs as analyzed using specific kit. FIG. 3E-F: IHC staining of si-Scr- or si-hVDAC1-TTs sections for stem cell markers c-Kit, Klf4, Sox2, Musashi, Nestin, NGFR, S100b, CD44.

FIG. 4 shows inhibition of invasion in si-hVDAC1-TTs with altered expression of stem cell markers.

FIG. 6 demonstrates DNA microarray and bioinformatics analyses of si-hVDAC1- and si-Scr-TTs.

FIG. 7 E, F: IHC of si-Scr- and si-hVDAC1-TTs stained for Ki-67 (FIG. 7E); positive cells counted over several fields (FIG. 7F). FIG. 7 H, I: IHC and WB analyses of EGFR.

(FIG. 8A); GAPDH, LDH and VDAC1 (FIG. 8B); and CS, complex IVc and ATP synthase 5a (FIG. 8C).

DETAILED DESCRIPTION OF THE INVENTION

Figure 1A:
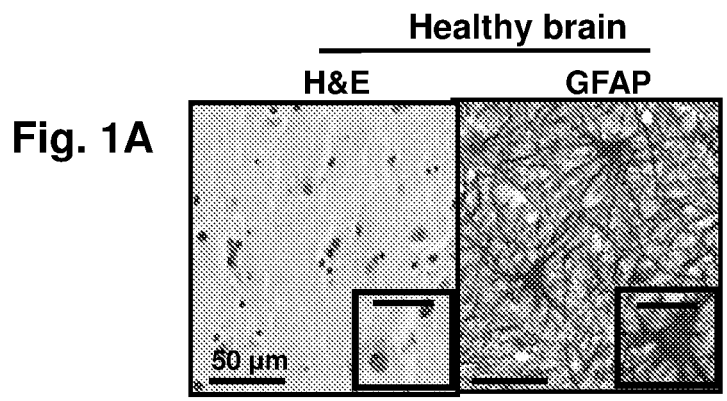
FIG. 1 shows morphological changes and expression of neuronal markers associated with cell differentiation in GBM. Human normal (FIG. 1A) or GBM brains (FIG. 1B) stained with H&E or anti-GFAP antibodies. Human VDAC1 silencing siRNA (si-hVDAC1) (FIG. 1C) or scrambled siRNA (si-Scr) (FIG. 1D) treated U-87MG xenograft tumors sections stained with H&E or anti-GFAP antibodies.
FIG. 1E: Typical sections from si-Scr- and si-hVDAC1-treated tumor (TT)s, immune-stained for Map2 and TUBB3.
FIG. 1F: WB of GFAP and TUBB3 in si-Scr- and si-hVDAC1-TTs. RU=relative units.
FIG. 1G: Schematic presentation of early precursor cell differentiation into mature astrocytes via several possible intermediate states: Late precursor cells, immature astrocytes, or neurons via immature neurons. mRNA levels of markers specific for each state in si-hVDAC1-TTs relative to those in si-Scr-TTs are presented. Results are the mean±SEM (n=3-5 tumors); p:*≤0.05; ≤0.001; *≤0.0001.
FIG. 1H: Immunofluorescent staining of si-Scr- and si-hVDAC1-TTs-derived sections for Nestin, GFAP, TUBB3 and GAD-67.
FIG. 1I: IHC staining of VDAC1 of human normal brain (n=13) or glioblastoma (GBM) (n=41) in tissue microarray slides (Biomax). Percentages of sections stained at the intensity indicated are shown.

The present invention discloses hitherto unknown outcomes resulting from reducing the expression of VDAC1 in cancer cell, particularly in cancer stem cells and quasi (not finally) differentiated cancer cells. Unexpectedly, the present invention shows that reduced expression of VDAC1, exemplified by siRNA silencing of its encoding gene, has led to the differentiation of glioblastoma cancer stem cells into non-replicating end-stage-like neurons and astrocytes. It was further shown that the silencing had reversed EMT and reduced TAMs abundance and angiogenesis in the treated tumor tissues. Taken together, these unexpected phenomena of VDAC1 reduced expression can be used to reduce the tumorigenicity of tumors comprising cancer stem cells and to prevent recurrence of cancer diseases characterized by cancer-stem cells containing tumors, including, but not limited to brain, breast, prostate, cervical, ovary, pancreas, head and neck, sarcoma, lymphoma, melanoma and colon cancer. In certain exemplary embodiments, the brain cancer is glioblastoma.

Definitions

The terms "VDAC1" and "hVDAC1" are used herein interchangeably and refer to the human voltage-depended anion channel isoform 1 (hVDAC1) of a highly conserved family of mitochondrial porin. Four VDAC isoforms, encoded by three genes, are known to date; as used herein, the terms "VDAC1" and "hVDAC1" refer to a 283 amino acid protein (NP_003365) having the amino acids sequence set forth in SEQ ID NO:1, encoded by a polynucleotide having the nucleic acid sequence set forth in SEQ ID NO:2.

As used herein, the term "cancer stem cells" refers to an undifferentiated cell which is capable of proliferation and giving rise to more progenitor cells having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "cancer stem cell" refers then, to a cell with the capacity or potential, under particular circumstances, to differentiate to a more specialized or differentiated phenotype, and which retains the capacity, under certain circumstances, to proliferate without substantially differentiating. In one embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell which itself is derived from a pluripotent cell, and so on. While each of these multipotent cells can be considered stem cells, the range of cell types each can give rise to can vary considerably. Some differentiated cells also have the capacity to give rise to cells of greater developmental potential. Such capacity can be natural or can be induced artificially upon treatment with various factors. In many biological instances, stem cells are also "multipotent" because they can produce progeny of more than one distinct cell type, but this is not required for "stemness." Self-renewal is the other classical part of the stem cell definition, and it is essential as used herein. Cancer stem cells have the ability for self-renewal, multipotent differentiation and vigorous proliferative capacity.

With reference to cells, the terms ""differentiated" or "differentiating" are relative terms; a "differentiated cell" is a cell that has progressed further down the developmental pathway with increased functional potential than the cell it is being compared with. Thus, stem cells can differentiate to lineage-restricted precursor cells (such as a mesodermal stem cell), which in turn can differentiate into other types of precursor cells further down the pathway, and then to an end-stage differentiated cell, which plays a characteristic role in a certain tissue type (for example neurons), and can or cannot retain the capacity to proliferate further.

As used herein "tumorigenic" refers to the functional features of a solid or non-solid tumor stem cell including the properties of self-renewal (giving rise to additional tumorigenic cancer stem cells) and proliferation to generate all other tumor cells (giving rise to differentiated and thus non-tumorigenic tumor cells) that allow cancer stem cells to form a tumor. The terms "reducing tumorigenicity" and "reduction of tumorigenicity" are used interchangeably herein and refer to the reduction in the number and/or frequency of cancer stem cells and cancer cells in a tumor leading to reduction in the tumor invasiveness and/or to the prevention of the tumor recurrence.

The term "stemness" as used herein refers to a cell with stem cell properties, for example a cell that has the capacity for self-renewal, for example a cell that is totipotent, pluripotent or multipotent. A cancer cell that is a "cancer stem cell" or a cancer cell with stemness properties is a cancer cell which can give rises to daughter cells which themselves can be induced to proliferate and produce progeny that subsequently differentiate into one or more mature cell types, while also retaining one or more cells with parental developmental potential.

The terms "oligonucleotide", "oligonucleotide sequence", "nucleic acid sequence", and "polynucleotide" are used interchangeably herein and refer to an oligomer or polymer of ribonucleic acid (ribo-oligonucleotide or ribo-oligonucleoside) or deoxyribonucleic acid comprising up to about 100-1,000 nucleic acid residues. These terms encompass nucleotide sequences strands composed of naturally-occurring nucleobases, sugars and covalent inter-sugar linkages as well as oligonucleotides having non-naturally-occurring portions which function similarly. Such modified or substituted oligonucleotides may be preferred over native forms because of the valuable characteristics including, for example, increased stability in the presence of plasma nucleases and enhanced cellular uptake. An oligonucleotide may be a polymer of RNA or DNA or hybrid thereof, that is single- or double-stranded, linear or branched, and that optionally contains synthetic, non-natural or altered nucleotide bases. The terms also encompass RNA/DNA hybrids. It is to be explicitly understood that the oligonucleotide sequences provided herein can be of DNA or RNA molecules.

The terms "construct", or "RNAi expression construct" are used herein interchangeably to describe an artificially assembled or isolated nucleic acid molecule which includes the polynucleotide of interest. In general a construct may include the polynucleotide or polynucleotides of interest, a marker gene which in some cases can also be a gene of interest and appropriate regulatory sequences. According to certain embodiments of the invention, the polynucleotide of interest encode siRNA molecule. It should be appreciated that the inclusion of regulatory sequences in a construct is optional, for example, such sequences may not be required in situations where the regulatory sequences of a host cell are to be used. The regulatory elements typically include a promoter sequence for directing transcription of the polynucleotide of interest in the cell in a constitutive or inducible manner. The term construct includes vectors but should not be seen as being limited thereto. According to certain embodiments, the term "vector," is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome (such as an adenoviral vector, a lentiviral vector, etc.). Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with, the host genome.

The terms "complementary" or "complement thereof" are used herein to refer to the sequences of polynucleotides which is capable of forming Watson & Crick base pairing with another specified polynucleotide throughout the entirety of the complementary region. This term is applied to pairs of polynucleotides based solely upon their sequences and not any particular set of conditions under which the two polynucleotides would actually bind. The terms "substantially complementary" and "sufficiently complementary" are used herein interchangeably. An oligomeric compound need not be 100% complementary to its target nucleic acid to be specifically hybridizable. Moreover, an oligomeric compound may hybridize over one or more segments such that intervening or adjacent segments are not involved in the hybridization (e.g., a bulge, a loop structure or a hairpin, structure). A "non-complementary nucleobase" means a nucleobase of an antisense oligonucleotide that is unable to undergo precise base pairing with a nucleobase at a corresponding position in a target nucleic acid. In some embodiments there are non-complementary positions, also known as "mismatches", between the oligomeric compound and the target nucleic acid, and such non-complementary positions may be tolerated between an oligomeric compound and the target nucleic acid provided that the oligomeric compound remains substantially complementary to the target nucleic acid.

The term "expression", as used herein, refers to the production of a functional end-product e.g., an mRNA or a protein.

According to one aspect, the present invention provides a method of reducing the tumorigenicity of a tumor, the method comprises administering to, or expressing in cells of a subject affected with a tumor comprising cancer stem cells (CSCs) an effective amount of at least one voltage dependent anion channel 1 (VDAC1)-silencing oligonucleotide, thereby reducing the number and/or frequency of the CSCs in said tumor.

According to another aspect, the present invention provides a method for inhibiting cancer stem cells within a tumor, the method comprises administering to, or expressing in a tumor comprising cancer stem cells (CSCs) an effective amount of at least one voltage dependent anion channel 1 (VDAC1)-silencing oligonucleotide.

Without wishing to be bound by any specific theory or mechanism of action, inhibition of the CSCs within a tumor is the outcome of inhibition and/or reduction in the number of CSCs by inducing CSC differentiation leading to reduced heterogenicity in the cancer cell population on phenotypical level.

According to certain embodiments, the tumor is a non-solid tumor. According to some embodiments, the non-solid tumor is blood cancer.

According to other embodiments, the tumor is a solid tumor. According to certain embodiments, the solid tumor is selected from the group consisting of brain, breast, prostate, cervical, ovary, pancreas, head and neck, lymphoma, melanoma and colon cancer. Each possibility represents a separate embodiment of the present invention. According to certain embodiments, the brain tumor is glioma. According to certain exemplary embodiments, the glioma is glioblastoma multiforme (GBM).

According to yet additional aspect, the present invention provides a method of treating a subject with metastatic cancer or at risk of developing metastatic cancer, the method comprises administrating to, or expressing in cells of the subject an effective amount of at least one voltage dependent anion channel 1 (VDAC1)-silencing oligonucleotide.

The central role of VDAC1 in cell energy and metabolism is reflected in its over-expression in many tumors, including glioma and in VDAC1 depletion impairing cancer cell energy and metabolic homeostasis (U.S. Pat. No. 8,093,369; Arif, T, 2014, ibid; Shoshan-Barmatz et at, 2015, ibid, FIG. 1I).

Figure 3:
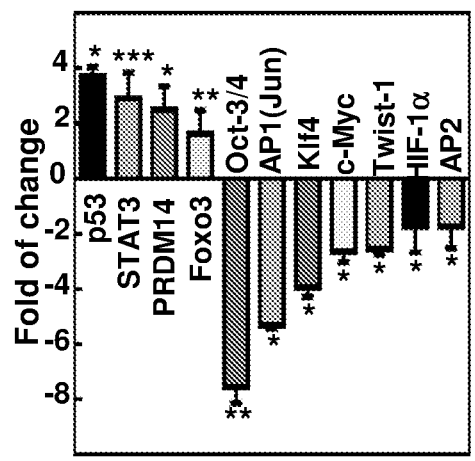
FIG. 3 shows alteration of transcription factors (TF) levels and stem cells and EMT markers expression in si-hVDAC1-TTs.
Figure 3B:
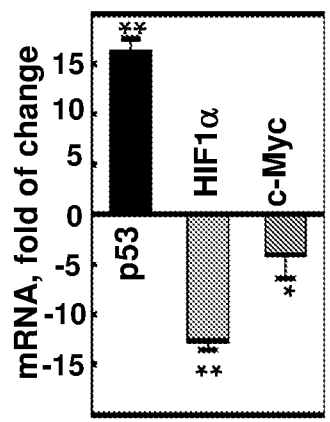
FIG. 3B: qRT-PCR analysis of p53, c-Myc and Hif-1α mRNA levels in U-87MG si-hVDAC1-TTs, relative to si-Scr-TTs. Results=mean±SEM (n=3-5 tumors); p: *≤0.05; **≤0.001.
Figure 3C:
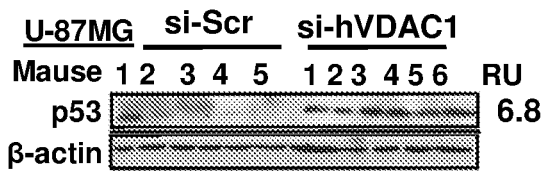
FIG. 3C-D: Western blotting (WB) of p53 in si-Scr- and si-hVDAC1-TTs derived from U-87MG (FIG. 3C) or U-118MG cells (FIG. 3D).
Figure 3D:
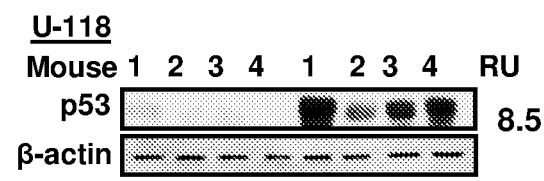
Figure 3G:
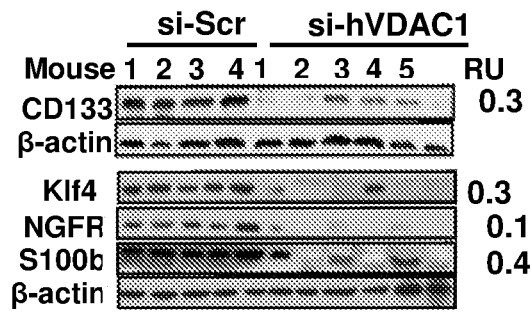
FIG. 3G: WB of CD133, Klf4, NGFR and S100b in si-Scr- and si-hVDAC1-TTs.

Recent studies have reinforced the hypothesis that human gliomas contain a neural stem cell lineage (Dirks P B., 2010. Molecular oncology 4, 420-430) capable of self-renewal and differentiation into multiple lineages (Chen J et al., 2012. Nature 488, 522-526). Unexpectedly, as exemplified herein (FIG. 3E-I), tumor treatment with siRNA targeted to hVDAC1 (si-hVDAC1) apparently eliminated GSCs, as reflected in the high decrease in expression of factors known to be involved in stemness and invasion (Shiras A et al., 2003. Neoplasia 5, 520-532). These included CD133, c-Kit, Sox2, Musashi, S100b, Klf4, Oct3/4, Nestin, CD44, Nanog and NGFR (FIG. 3E-G). Oct3/4 and Nanog are the earliest expressed set of genes known to control stemness and repress genes essential for development and/or differentiation (Sun Y et al., 2006. Critical reviews in eukaryotic gene expression 16, 211-231). CD133 is used as a pluripotent stem cell marker associated with an aggressive radio- and chemo-resistant sub-population of GBM cells (Yan X et al., 2011. PNAS USA 108, 1591-1596). The decrease in GSC levels upon si-hVDAC1 treatment would thus make GBM more sensitive to irradiation and chemotherapy and addresses any concern about the tumor-forming potential of pluripotent stem cells. The decrease in GSC levels could be due to proliferation inhibition and/or differentiation, as reflected in morphological changes and increased expression of the neuronal differentiation markers GFAP, MAP-2, TUBB3 and GAD67 (FIGS. 1, 2, 3).

VDAC1 depletion leading to cell differentiation is further supported by bioinformatics promoter analysis of genes differentially expressed in si-hVDAC1-treated tumors (TTs), pointing to enrichment for binding sites of TFs involved in cell differentiation (FIG. 3A-D). FOXP1 was over-expressed in a cohort of GBM patients, with its silencing leading to tumor growth inhibition (Gomez G G et al., 2014. Cancer Research 74, 1429-1439). NRSF was also found to be enriched in GBM, with its knockdown strongly reducing tumor-initiating capacity in vivo (Binello E and Germano, I M., 2012. Neuro-oncology 14, 256-265). Finally, HNF4 and MAZ were reported to co-regulate neural stem cell differentiation via Rho-GDIγ (Wang J et at, 2013. Molecular Neurobiology 47, 228-240). As exemplified hereinbelow, these TFs were down-regulated in si-hVDAC1-TTs, thus leading to cell differentiation.

Hence, based on cell morphological changes, increased expression of mature neuronal and astrocytic markers and the decreased expression of GSCs markers (Figure. 3), it is proposed that upon VDAC1 depletion, GSCs in U-87MG cell-derived tumors are capable of in vivo neuronal differentiation toward mature neurons and astrocytes. This finding of the present invention is of high significance, as end-stage neurons cannot replicate, thereby preventing tumor re-growth and relapse.

According to certain embodiments, the VDAC1-silencing oligonucleotide comprises at least 15 contiguous nucleic acids identical to the gene or mRNA encoding human VDAC1 protein or to a complementary polynucleotide thereof, wherein the human VDAC1 protein comprises the amino acid sequence set forth in SEQ ID NO:1.

According to certain embodiments the hVDCA1 protein is encoded by the nucleic acid sequence set forth in SEQ ID NO:2.

The terms "VDAC1-silencing oligonucleotide", "VDAC1-silencing oligonucleotide molecule", "VDAC1-silencing molecule" or "oligonucleic that inhibits or reduces VDAC1 expression" as used herein, denote an oligonucleic acid capable of specifically reducing the level or expression of the gene product, i.e. the level of VDAC1 RNA, below the level that is observed in the absence of the oligonucleic acid. In some embodiments gene expression is down-regulated by at least 25%, preferably at least 50%, at least 70%, 80% or at least 90%.

The siRNA designated si-hVDAC1 in the figures and specification of the present invention refers to siRNA comprising a first oligonucleotide having the nucleic acid sequence set forth in SEQ ID NO:14 (the "sense" oligonucleotide) and a second oligonucleotide having the nucleic acid sequence set forth in SEQ ID NO:15 (the "antisense" oligonucleotide).

It is to be explicitly understood that while silencing the expression of VDAC1 as described herein uses RNAi as silencing oligonucleotide molecules, other methods for silencing the expression of VDAC1 including inhibiting transcription from the VDAC1 gene to VDCA1 RNA; by inhibition of the maturation process from hnRNA to mRNA; by promotion of mRNA degradation in the cytoplasm by enzymes (by forming RNA duplexes or triplexes, and by catalytic cleavage of nucleic acid based enzymes (DNAzymes and RNAzymes).

According to certain exemplary embodiments, the VDAC1-silencing oligonucleotide is RNAi molecule. According to additional exemplary embodiments, the RNAi molecule is selected from the group consisting of siRNA and shRNA. Each possibility represents a separate embodiment of the present invention.

As used herein the term "siRNA" (small interfering RNA) refers to a nucleic acid that forms a double stranded RNA, wherein the double stranded RNA has the ability to reduce or inhibit expression of a particular gene or target gene when the siRNA is present or expressed in the same cell as the gene or target gene. The double stranded RNA siRNA can be formed by the complementary strands. The complementary portions of the siRNA that hybridize to form the double stranded molecule typically have substantial or complete identity. In one embodiment, a siRNA refers to a nucleic acid that has substantial or complete identity to sequence of a target gene and forms a double stranded RNA. The sequence of the siRNA can correspond to the full length target gene, or to a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 19-25 nucleotides in length, e.g., 19, 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotides, antisense strand, followed by a nucleotide loop of about 5 to about 9 nucleotides, and the analogous sense strand. Alternatively, the sense strand can precede the nucleotide loop structure and the antisense strand can follow.

As illustrated it Table 1 hereinbelow, certain exemplary silencing oligonucleotide have been designed, targeted to specific areas of the VDAC1 gene (hybridizable with specific areas of the VDAC1 transcript) and substantially comprise a nucleic acid sequence as set forth in any one of SEQ ID NOs:3-10.

TABLE 1

Exemplary VDAC1-silencing oligonucleotide (sense strand)

| Sense Sequence | SEQ ID NO: | Target VDAC1 Sequence | SEQ ID NO: | Location |
|---|---|---|---|---|
| ACACUAGGCACCGAGAUUA | 3 | ACACTAGGCACCGAGATTA | 16 | 238-256 |
| GGGCUAUGGAUUUGGCUUA | 4 | GGGCTATGGATTTGGCTTA | 17 | 159-177 |
| GCUUGGUCUAGGACUGGAA | 5 | GCTTGGTCTAGGACTGGAA | 18 | 921-939 |
| AAGCUGACCUUCGAUUCAU | 6 | AAGCTGACCTTCGATTCAT | 19 | 531-549 |
| GAAUGACGGGACAGAGUUU | 7 | GAATGACGGGACAGAGTTT | 20 | 797-815 |
| UCGGAAUAGCAGCCAAGUA | 8 | TCGGAATAGCAGCCAAGTA | 21 | 901-919 |
| CUCUUCUGGAUGGCAAGAA | 9 | CTCTTCTGGATGGCAAGAA | 22 | 1027-1045 |
| GAAUAGCAGCCAAGUAUCAG | 10 | GAATAGCAGCCAAGTATCAG | 23 | 487-505 |

According to additional embodiments, at least one of the siRNA nucleic acids is chemically modified. Typically, the modification is 2'-O-methyl modification of a guanine or uracil. According to certain embodiments, the first and the second polynucleotide of the RNAi comprise several chemically modified guanine and/or uracil nucleotides. According to certain exemplary embodiments, the modified siRNA molecule comprises a first oligonucleotide having the nucleic acid sequence set forth in SEQ ID NO:14 and a second oligonucleotide having the nucleic acid sequence set forth in SEQ ID NO:15.

According to certain embodiments, reducing the tumorigenicity of the tumor comprises attenuating the invasive potential of said tumor, particularly of the tumor cancer stem cells.

The epithelial-mesenchymal transition (EMT) plays a critical role in embryonic development. EMT is also involved in cancer progression and metastasis and it is probable that a common molecular mechanism is shared by these processes. Cancer cells undergoing EMT can acquire invasive properties and enter the surrounding stroma, resulting in the creation of a favorable microenvironment for cancer progression and metastasis. Furthermore, the acquisition of EMT features has been associated with chemoresistance which could give rise to recurrence and metastasis after standard chemotherapeutic treatment. Thus, EMT could be closely involved in carcinogenesis, invasion, metastasis, recurrence, and chemoresistance (Iwatsuki, M et al., 2010. Cancer science 101, 293-299).

Treating tumors with siRNA targeted to hVDAC1 changed the expression of proteins involved in EMT and of extracellular matrix (ECM) components (Table 3). Tumor treatment with si-hVDAC also decreased the levels of tumor-associated macrophage (TAM) markers (F4/80, CD68), suggesting the tumors possess less pro-tumorigenic activity (inflammation, ROS, cytokine, growth factors). Among cells of immune system, macrophages are particularly abundant and are present at all stages of tumor progression. Macrophages generally have a pro-tumoral role. In the primary tumor, macrophages take substantial task in angiogenesis stimulation and enhance tumor cell motility and invasion (Noy R and Pollard J W. 2014 Immunity 41(1), 49-61). Without wishing to be bound by any specific theory or mechanism of action, the reduction in the pro-tumorigenic activity also decreased the angiogenesis potential (Glass R and Synowitz, M., 2014. Glia 62, 514-525). Indeed, VDAC1 depletion resulted in a strong decrease in angiogenesis, both in microvessel density and VEGF levels (FIG. 4E-H). VEGF is highly over-expressed in GBM (Rahmathulla G et al., 2013. OncoTargets and therapy 6, 371-389). Anti-angiogenesis therapy, like VEGFR inhibitors/antibodies, has been a focal area in cancer drug discovery for over a decade, including as GBM therapy, albeit with limited success or organ-specific toxicity. The present invention now discloses that RNAi molecules targeted to silence VDAC1 expression can be used as efficient anti-angiogenesis drugs.

Changes in cancer cell metabolism contribute to the oncogenic process. The metabolic changes support the three basic needs of dividing cancer cells: rapid ATP generation to maintain energy status; increased biosynthesis of macromolecules; and tightened maintenance of appropriate cellular redox status. VDAC1 is a key protein in regulating cancer cell energy and has been shown to be over-expressed in cancer cells including glioblastoma. VDAC1 is essential to mitochondrial ATP production and is the main transporter of ATP and other metabolites and ions through the outer mitochondrial membrane. Moreover, VDAC1 mediates cholesterol transport, with cancer cells exhibiting much higher cholesterol levels than do healthy cells. It has been previously described that silencing the expression of VDAC1 disrupts energy production and cell growth. The present invention now shows that silencing VDAC1 expression resulted in down regulation of glucose transporter, glycolytic enzymes, and modified expression profile transcription factors regulating metabolism. In particular, the present invention shows that silencing VDAC1 resulted in dramatic decrease in the expression level of the glucose transported Glut-1, facilitating glucose uptake by the cells and of the glycolytic enzymes hexokinase (HK-1), glyceraldehyde dehydrogenase (GAPDH) and lactate dehydrogenase (LDH), all known to be up-regulated in cancer cells.

In summary, the present invention now shows that unexpectedly, VDAC1 depletion reversed the reprogrammed energy and metabolism characteristic to cancer cells, reinforced cell differentiation and reduced stemness, invasion, TAMs abundance and angiogenesis.

Silencing Molecules

The silencing oligonucleotide molecules designed according to the teachings of the present invention can be generated according to any nucleic acid synthesis method known in the art, including both enzymatic syntheses and solid-phase syntheses. Any other means for such synthesis may also be employed; the actual synthesis of the nucleic acid agents is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that nucleic acid agents of the present invention can be also generated using an expression vector as is further described hereinbelow.

According to certain embodiments, the silencing oligonucleotide molecules of the present invention are modified. Nucleic acid agents can be modified using various methods known in the art.

For example, the silencing oligonucleotide molecules of the present invention may comprise heterocylic nucleosides consisting of purines and the pyrimidines bases, bonded in a 3'-to-5' phosphodiester linkage.

Preferably used nucleic acid agents are those modified either in backbone, internucleoside linkages, or bases, as is broadly described hereinbelow.

Specific examples of silencing oligonucleotide molecules useful according to this aspect of the present invention include oligonucleotides or polynucleotides containing modified backbones or non-natural internucleoside linkages.

Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones;

amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other silencing oligonucleotide molecules which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Silencing oligonucleotide molecules of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 2'-O-methyl-modified nucleotides, particularly uracil and guanine; 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

The silencing oligonucleotide molecules of the present invention are of at least 10, at least 15, or at least 17 bases specifically hybridizable with VDCA1 RNA. According to certain exemplary embodiments, the siRNAs of the present invention are of 19 bases.

It should be appreciated that the present invention also envisages agents other than nucleic acid agents that are capable of down-regulating VDCA1 RNA such as knockout agents.

Synthesis of RNAi molecules suitable for use with the present invention can be effected as follows. First, the VDAC1 nucleic acid sequence target is scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Examples of siRNAs which are capable of down-regulating VDAC1 that may be used according to this aspect of the present invention are those set forth by SEQ ID NOs:3-10 and sequences essentially complementary thereto.

Another agent capable of downregulating the expression of a VDAC1 RNA is a DNAzyme molecule capable of specifically cleaving its encoding polynucleotide. DNAzymes are single-stranded nucleic acid agents which are capable of cleaving both single and double stranded target sequences (Breaker R R and Joyce, G. 1995. Chemistry and Biology 2, 655; Santoro, S. W. & Joyce, G. F. Proc. Natl, Acad. Sci. USA 1997; 94:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M (2002. Curr Opin Mol Ther 4, 119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-ab1 oncogenes were successful in inhibiting the oncogenes expression in leukemia cells, and lessening relapse rates in autologous bone marrow transplant in cases of Chronic Myelogenous Leukemia (CML) and Acute Lymphocytic Leukemia (ALL).

Another agent capable of downregulating VDAC1 RNA is a ribozyme molecule capable of specifically cleaving its encoding polynucleotide. Ribozymes are being increasingly used for the sequence-specific inhibition of gene expression by the cleavage of mRNAs encoding proteins of interest (Welch et al., 1998. Curr Opin Biotechnol. 9:486-96). The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders (Welch et al., 1998. Clin Diagn Virol. 10:163-71). Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—http://www.rpi.com/index.html).

An additional method of downregulating VDAC1 RNA is via triplex forming oligonuclotides (TFOs). In the last decade, studies have shown that TFOs can be designed which can recognize and bind to polypurine/polypirimidine regions in double-stranded helical DNA in a sequence-specific manner. Thus the DNA sequence encoding the VDCA1 RNA of the present invention can be targeted thereby down-regulating the RNA molecule.

The recognition rules governing TFOs are outlined by Maher III, L. J., et al., Science (1989) 245:725-730; Moser, H. E., et al., Science (1987)238:645-630; Beal, P. A., et al., Science (1991) 251:1360-1363; Cooney, M., et al., Science (1988) 241:456-459; and Hogan, M. E., et al., EP Publication 375408. Modification of the oligonuclotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer (2003) J Clin Invest; 112:487-94).

In general, the triplex-forming oligonucleotide has the sequence correspondence:

oligo 3'-A G G T
duplex 5'-A G C T
duplex 3'-T C G A

However, it has been shown that the A-AT and G-GC triplets have the greatest triple helical stability (Reither and Jeltsch (2002), BMC Biochem, September 12, Epub). The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and subsequent formation of the triple helical structure with the target DNA, induces steric and functional changes, blocking transcription initiation and elongation, allowing the introduction of desired sequence changes in the endogenous DNA and results in the specific downregulation of gene expression. Examples of such suppression of gene expression in cells treated with TFOs include knockout of episomal supFG1 and endogenous HPRT genes in mammalian cells (Vasquez et al., Nucl Acids Res. (1999) 27:1176-81, and Puri, et at, J Biol Chem, (2001) 276:28991-98), and the sequence- and target-specific downregulation of expression of the Ets2 transcription factor, important in prostate cancer etiology (Carbone, et al., Nucl Acid Res. (2003) 31:833-43), and the pro-inflammatory ICAM-1 gene (Besch et al., J Biol Chem, (2002) 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000. 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003. 112, 487-94). Detailed description of the design, synthesis and administration of effective TFOs can be found in U.S. Patent Application Nos. 2003 017068 and 2003 0096980 to Froehler et al., and 2002 0128218 and 2002 0123476 to Emanuele et al., and U.S. Pat. No. 5,721,138 to Lawn.

It will be appreciated that silencing oligonucleotide molecules capable of hybridizing VDCA1 mRNA may downregulate an activity thereof by preventing VDCA1 mRNA binding to another downstream agent.

Silencing Molecule Delivery and Expression

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells (see, e.g., U.S. Pat. Nos. 5,656,611, 5,753,613, 5,785,992, 6,120, 798, 6,221,959, 6,346,613, and 6,353,055).

According to certain exemplary embodiments, the silencing oligonucleotide molecules of the present invention, specifically siRNAs, are shielded and/or encapsulated in Poly(D,L-lactide-co-glycolide) (PLGA). Without wishing to be bound by any specific theory or mechanism of action, PGLA shielding or encapsulation enables the siRNA molecules to cross the blood brain barrier (BBB). As mentioned hereinabove, the nucleic acid agents of the present invention (e.g., an siRNA molecule such as those set forth by SEQ ID NO:3-15) can be expressed in cells.

It will be appreciated that the VDAC1 silencing oligonecleotides of the present invention may be expressed directly in the subject (i.e. in vivo gene therapy) or may be expressed ex vivo in a cell system (autologous or non-autologous) and then administered to the subject.

To express such an agent (i.e., to produce an RNA molecule) in mammalian cells, a nucleic acid sequence encoding the agents of the present invention is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific (Pinkert et al., 1987. Genes Dev. 1, 268-277 0, lymphoid specific promoters 9Calame et al., 1988. Adv. Immunol. 43, 235-275 0; in particular promoters of T-cell receptors 9Winoto et at, 1989. EMBO J. 8, 729-733 0 and immunoglobulins; (Banerji et al., 1983. Cell 33, 729-740), neuron-specific promoters such as the neurofilament promoter (Byrne et al., 1989. Proc. Natl. Acad. Sci. USA 86, 5473-5477), pancreas-specific promoters (Edlunch et al., 1985. Science 230, 912-916) or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability (Soreq et al., 1974. J. Mol Biol. 88: 233-45).

Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMT010/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of the VDCA1 silencing molecules of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. (Biotechniques 4 (6): 504-512, 1986) and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol (Tonkinson et al., 1996. Cancer Investigation, 14(1), 54-65). The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. Optionally, the construct may also include a signal that directs polyadenylation, as well as one or more restriction sites. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription of the inserted coding sequence, the expression construct of the present invention can also include sequences engineered to enhance stability, production, purification, yield or toxicity of the expressed RNA.

The agents of the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism. According to the present invention, "an active ingredient" refers to VDAC1-silencing oligo nucleotide molecule.

The terms "physiologically acceptable carrier" and "pharmaceutically acceptable carrier" which may be interchangeably used herein refer to a carrier or a diluent that does not cause significant irritation to an organism and does not abrogate the biological activity and properties of the administered compound. An adjuvant is included under these phrases.

The term "excipient" as is used herein refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include parenteral, transmucosal, especially transnasal, intestinal, rectal, or oral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into the tumor (i.e. in situ).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (naked silencing oliginucleotides, nucleic acid construct comprising same and/or encapsulated or shielded silencing oliginucleotides and constructs comprising same) effective in reducing VDAC1 expression and in preventing, alleviating or ameliorating tumor progression, invasion and recurrence, or prolonging the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays.

For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

The following examples are presented in order to more fully illustrate some embodiments of the invention. They should, in no way be construed, however, as limiting the broad scope of the invention. One skilled in the art can

EXAMPLES

Material and Methods

Materials

The cell transfection agents JetPRIME and JetPEI were from PolyPlus transfection (Illkirch, France), while non-modified and 2'-O-methyl-modified hVDAC1-siRNAs were obtained from Genepharma (Suzhou, China). Polyethylenimine (PEI), Poly(D,L-lactide-coglycolide) (PLGA), Polyvinyl alcohol (PVA), propidium iodide (PI), sulforhodamine B (SRB), Tween-20, hematoxylin and eosin were obtained from Sigma (St. Louis, Mo.). Paraformaldehyde was purchased from Emsdiasum (Hatfield, Pa.). Dulbecco's modified Eagle's medium (DMEM) and Roswell Park Memorial Institute (RPMI) 1640 growth media were obtained from Gibco (Gray island, NY). Normal goat serum (NGS) and the supplements fetal calf serum (FCS), L-glutamine and penicillin/streptomycin were obtained from Biological Industries (Beit Haemek, Israel). A cancer stem cell TF activation profiling plate array was obtained from Signosis (Santa Clara, Calif.). Primary antibodies, their source and the dilution used are detailed in Table 1. Horseradish peroxidase (HRP)-conjugated anti-mouse, anti-rabbit and anti-goat antibodies were from KPL (Gaithersburg, Md.). TUNEL stain was obtained from Promega (Madison, Wis.).

Cell Culture and Transfection

U-87MG, U-118, LN-18 (human glioblastoma), MZ-18 and MZ327 (human glioblastoma-patient derived cell line, and GL-261 (mouse glioblastoma) cells were maintained in DMEM culture medium supplemented with 10% FBS (5% for L18), 1 mM L-glutamine, 100 U/ml penicillin, and 100 µg/ml streptomycin. U-251 (human glioblastoma) cells cultured in RPMI-1640 medium supplemented with 10% FBS, 1 mM L-glutamine, 100 U/ml penicillin, and 100 µg/ml streptomycin at 37° C. and 5% $CO_2$. G7-glioma-derived stem cell line were grown using specific glioblastoma stem cell medium, as described (Pollard S M et al. 2009. Cell Stem Cell. 4(6), 568-580). Non-modified and 2'-O-methyl modified siRNAs targeted to hVDAC1 (si-hVDAC1) were synthesized by Dharmacon or were obtained from Genepharma.

The following sequences were used:

```
Human VDAC1 silencing siRNA (si-hVDAC1):
si-hVDAC1:
Sense:
                                       (SEQ ID NO: 3
5'ACACUAGGCACCGAGAUUA3', positions 238-256 of
VDAC1 coding sequence (SEQ ID NO: 2);
and Antisense:
                                      (SEQ ID NO: 94)
5'UAAUCUCGGUGCCUAGUGU3' si-hVDAC1 2/A:
Sense:
                                      (SEQ ID NO: 14)
5'ACACUAGGCACCGAGAUUA3'-with 2'-O-methyl-modified
nucleotides indicated in bold and underlined;
and Antisense:
                                      (SEQ ID NO: 15)
5'UAAUCUCGGUGCCUAGUGU3' with 2'-O-methyl-modified
nucleotides indicated in bold and underlined.
```

Scrambled siRNA (si-Scr) sequences:

```
Scrambled-
Sense:
                                      (SEQ ID NO: 24)
-5'GCAAACAUCCCAGAGGUAU3' with 2'-O-methylmodified nucleotides indicated in bold and underlined
and Antisense:
                                      (SEQ ID NO: 25)
-5'AUACCUCUGGGAUGUUUGC3' with 2'-O-methyl-modified
nucleotides indicated in bold and underlined.
```

Addition silencing siRNA specific to human as well as murine VDAC1 was also designed:

```
VDAC1M/H,
Sense:
                                      (SEQ ID NO: 10)
5'-GAAUAGCAGCCAAGUAUCAG-3', positions 487-505 of VDAC1 coding sequence (SEQ ID NO: 2), flanked by tt nucleotides;
and Antisense:
                                      (SEQ ID NO: 13)
5'-UGAUACUUGGCUGCUAUUC-3' flanked by tt
nucleotides.
```

Cells were seeded (150,000 cells/well) on 6-well culture dishes to 40-60% confluence and transfected with 10-100 nM si-Scr or si-hVDAC1 using the JetPRIME transfection reagent (Illkirch, France), according to the manufacturers' instructions.

Xenograft and Intracranial-Orthotopic Xenograft Mouse Model

U-87MG ($2\times10^6$) and U-118MG ($3\times10^6$) glioblastoma cells were inoculated s.c. into the hind leg flanks of athymic eight-week old male nude mice (Harlan). Eleven days post-inoculation, tumor volume was measured (50-80 $mm^3$) and mice were randomized into two groups (9 animals/group), treated with si-Scr or si-hVDAC1 mixed with in vivo JetPEI reagent and injected into the established s.c. tumors (50 nM final, 2 boluses) every three days. At the end of the experiments, the mice were sacrificed, tumors were excised, and half of each tumor was either fixed and processed for IHC or frozen in liquid nitrogen for later immunoblot and RNA isolation.

For the intracranial-orthotopic mouse model, U-87MG cells were treated with 50 nM si-Scr or si-hVDAC1 twice at a 4-day interval and engrafted into a nude mouse brain using a stereotactic device. The anesthetized mice were immobilized in a stereotactic-head frame (Stoelting, Wood Dale, Ill.) and a middle incision was made on the skull and a burr hole placed 0.5 mm anterior to the bregma and 2.5 mm lateral to the midline using a drill (Stoelting). A 31-gauge needle (Hamilton syringe) was used to deliver tumor cells. The needle tip was inserted into the brain 3 mm deep, relative to the skull surface, and maintained at this depth for 2 minutes before injection of tumor cells. Under sterile conditions, a 3 µL solution containing U-87MG ($8\times10^4$) in phosphate buffered saline (PBS) cells were injected into the brain parenchyma over a period of 3 minutes using and UltraMicroPump III (World Precision Instruments, Sarasota, Fla.). After infusion, the needle was left in place for 1 minute before slow withdrawal. The burr hole was sealed using sterile bone wax, and the wound was closed with 5.0 nylon surgical suture. All surgical procedures were performed under sterile conditions. Tumor development was monitored using MRI 22 and 33 days after cell engrafting. At the end of the experiment, mice were sacrificed, and their brains were excised and processed for IHC.

In vivo brain MRI was performed using the M7 1-Tesla compact ICON system (Aspect Imaging, M7, Israel), equipped with a set of application-specific radiofrequency (RF) 20-mm mouse head coils. For in vivo imaging, animals were maintained in an anesthetized state with 1.5% isoflorane in $O_2$ and placed on a specially designed heated bed where physiological signals, such as breath rate, were monitored throughout the experiment to ensure the animals' well-being. MRI acquisition parameters included fast spin echo with a repetition time of 2,500 ms and echo time of 74 ms. Fifteen axial slices of 0.4 mm with a gap of 0.1 and a matrix of 256×256, field of view of 40 mm and acquisition time of 14.3 were collected (Tempel-Brami C et al. 2015. Toxicol Pathol 43, 633-650). Data were analyzed by VivoQuant 2.10 software. The experimental protocols used were approved by the Institutional Animal Care and Use Committee.

Immunoblot

For immunostaining, membranes containing electrotransferred proteins following SDS-PAGE were blocked with 5% non-fat dry milk and 0.1% Tween-20 in TBS, incubated with the primary antibodies (sources and dilutions as detailed in Table 2) and then with HRP-conjugated anti-mouse or anti-rabbit (1:10,000) or anti-goat (1:20,000) IgG. Enhanced chemiluminiscent substrate (Pierce Chemical, Rockford, Ill.) was used for detection of HRP activity.

TABLE 2

Antibodies against the indicated protein, their catalogue number, source and the dilutions used in IHC, immunoblot (WB) and immunofluorescence (IF) experiments

| Antibody | Source and Cat. No. | IHC | WB | IF |
|---|---|---|---|---|
| Mouse monoclonal anti-actin | Millipore, Billerica, MA, MAB1501 | — | 1:10000 | — |
| Mouse monoclonal anti-ATP5a | Abcam, Cambridge, UK, ab14748 | 1:300 | 1:1000 | — |
| Mouse monoclonal anti-β III tubulin | Abcam, Cambridge, UK ab7751 | 1:100 | 1:1000 | 1:200 |
| Rabbit polyclonal anti-CD31 | Abcam, Cambridge, UK ab28364 | 1:50 | — | — |
| Rabbit polyclonal anti-CD44 | Abcam, Cambridge, UK ab157107 | 1:1000 | 1:3000 | — |
| Mouse monoclonal anti-CD133 | Miltenyi Biotec GmbH, AC133 | — | 1:1500 | — |
| Rabbit polyclonal anti-citrate synthase | Abcam, Cambridge, UK ab96600 | 1:200 | 1:4000 | — |
| Rabbit polyclonal anti c-Kit | Dako, CL, USA, A4502 | 1:400 | — | — |
| Mouse monoclonal anti-cytochrome c | BD Bioscience, San Jose, CA, 556432 | 1:400 | 1:2000 | — |
| Rabbit monoclonal cytochrome c oxidase subunit VIc | Abcam, Cambridge, UK, ab150422 | 1:200 | 1:2000 | — |
| Rabbit polyclonal anti EGFR | Abcam, Cambridge, UK, ab2430 | 1:300 | 1:2000 | — |
| Mouse monoclonal anti-E-cadherin | Invitrogen, Life Technologies, NY, 18-0223 | 1:100 | 1:1000 | — |
| Rat monoclonal anti-F4/80 | Santa Cruz Biotechnology, Inc. Dallas, TX, sc52664 | 1:150 | — | — |
| Rabbit polyclonal anti-FoxP1 | Abcam, Cambridge, UK, ab191184 | 1:300 | 1:1500 | — |
| Mouse monoclonal anti-GAPDH | Abcam, Cambridge, UK, ab9484 | 1:200 | 1:1000 | — |
| Mouse monoclonal anti-GAD67 | Abcam, Cambridge, UK, ab26116 | — | 1:2000 | 1:1500 |
| Mouse monoclonal anti-GFAP | Santa Cruz Biotechnology, Inc. Dallas, TX, sc-33673 | 1:200 | 1:1000 | 1:150 |
| Rabbit monoclonal anti-Glut1 | Abcam, Cambridge, UK ab40084 | 1:200 | 1:1500 | — |
| Mouse monoclonal anti-HK-I | Abcam, Cambridge, UK ab105213 | 1:500 | 1:2000 | — |
| Rabbit polyclonal anti-HK II | Abcam, Cambridge, UK ab3279 | 1:400 | 1:2000 | — |
| Rabbit polyclonal ant-HNF4 | Abcam, Cambridge, UK, ab92378 | 1:300 | 1:1000 | — |
| Rabbit monoclonal anti-Ki67 | Thermo Scientific, NY RM-9106-s1 | 1:100 | — | — |
| Rabbit polyclonal anti-KLF4 | IMGENX Littleton, USA, IMG-6081-A | 1:200 | 1:1000 | — |
| Rabbit monoclonal anti-LDH | Epitomics, Cambridge, UK, 1980-1 | 1:300 | 1:1000 | — |
| Goat polyclonal anti-LDH-A | Santa Cruz Biotechnology, Inc. Dallas, TX, sc-27230 | — | 1:1500 | — |
| Mouse monoclonal anti-Map2 | Sigma-Aldrich, St. Louis, MI, M 4403 | 1:400 | — | — |
| Rabbit polyclonal anti-Maz | Abcam, Cambridge, UK, ab114965 | 1:300 | — | — |
| Mouse monoclonal anti-Musashi-1 | Millipore, Billerica, MA, MABE268 | 1:200 | — | — |
| Mouse monoclonal anti-N-cadherin | Invitrogen (Life Technologies), NY 18-0224 | 1:200 | — | — |
| Rabbit polyclonal anti-Nestin | Millipore, Billerica, MA, MAB353 | 1:400 | 1:1000 | 1:1500 |
| Rabbit polyclonal anti-NGFR | Santa Cruz Biotechnology, Inc. Dallas, TX, sc-8317 | 1:200 | 1:1000 | — |

TABLE 2-continued

Antibodies against the indicated protein, their catalogue number, source and the dilutions used in IHC, immunoblot (WB) and immunofluorescence (IF) experiments

|  |  | Dilution | | |
|---|---|---|---|---|
| Antibody | Source and Cat. No. | IHC | WB | IF |
| Rabbit polyclonal anti NRSF/Rest | Abcam, Cambridge, UK, ab70300 | 1:200 | — | — |
| Mouse monoclonal anti-P53 | Santa Cruz Biotechnology, Inc., Dallas, TX, sc-126 | — | 1:5000 | — |
| Goat polyclonal anti-S100b | Millipore, Billerica, MA, ABN59 | 1:300 | 1:2000 | — |
| Goat polyclonal anti-Sox2 | Santa Cruz Biotechnology, Inc. Dallas, TX, sc-17320 | 1:200 | 1:1500 | — |
| Rabbit monoclonal anti-VDAC1 | Abcam, Cambridge, UK, ab154856 | 1:500 | 1:5000 | — |
| Mouse monoclonal anti-VEGF | Santa Cruz Biotechnology, Inc. Dallas, TX. sc-65617 | 1:50 | 1:1000 | — |
| Mouse monoclonal anti-Vimentin | Invitrogen, Life Technologies, NY 18-0052 | 1:300 | 1:1000 | — |

IHC and Immunofluorescence of Tumor Tissue Sections

Immunohistochemical (IHC) and immunofluorescence staining was performed on 5 μm-thick formalin-fixed and paraffin-embedded tumor tissue sections. The sections were deparaffinized by placing the slides at 60° C. for 1 h and using xylene. Thereafter, the tissue sections were rehydrated with a graded ethanol series (100%-50%). Antigen retrieval for some proteins (VDAC1, Glut1, citrate synthases, HK-II, GAPDH, LDH, Nestin, NGFR, KLF4, Sox2, S100b, Mushahi, Map2, b-III tubulin (TUBB3), GAD67, ATP5a, cytochrome c oxidase subunit Vic, c-Kit, N-cadherin, E-cadherin and vimintein) was performed in 0.01 M citrate buffer (pH 6.0). For HK-I and CD31, VEGF, Ki-67, GFAP, F4/80, HNF4, FOXP1, NRSF/Rest and MAZ, antigen retrieval was performed in 10 mM Tris-EDTA (pH 9) and 0.5 M Tris (pH 10), for 30 minutes each at 95-98° C. After washing sections in PBS containing 0.1% Triton-X100 (pH 7.4), non-specific antibody binding was reduced by incubating the sections in 10% NGS for 2 h. After decanting excess serum, sections were incubated overnight at 4° C. with primary antibodies (sources and dilutions used detailed in Table 1). Sections were washed with PBST. For IHC, endogenous peroxidase activity was blocked by incubating the sections in 3% $H_2O_2$ for 15 min. After washing thoroughly with PBST, the sections were incubated for 2 h with the appropriate secondary antibodies. For IHC, anti-mouse or anti rabbit (1:250) secondary antibodies conjugated to HRP were used, as appropriate. Sections were washed five times in PBST and the peroxidase reaction was subsequently visualized by incubating with 3,3-diaminobenzidine (DAB) (ImmPact-DAB, Burlingame, Calif.). After rinsing in water, the sections were counterstained with hematoxylin and mounted with mounting medium. Finally, the sections were observed under a microscope (Leica DM2500) and images were collected at 20× magnification with the same light intensity and exposure time. Non-specific control experiments were carried out using the same protocols but omitting incubation with the primary antibodies. Hematoxylin-eosin staining was performed as described previously (Kiernan J. 2008. Histological and Histochemical Methods: Theory and Practice, 4th edition). For immunofluorescence, Cy3-conjugated anti-rabbit (1:500) or Cy2-conjugated anti-mouse (1:200) secondary antibodies were used. The cells were then stained with DAPI (0.07 μg/ml) and viewed with an Olympus IX81 confocal microscope.

TUNEL Assay

Fixed tumor sections in paraffin were processed for the TUNEL assay using the DeadEnd Fluorometric TUNEL system (Promega, Madison, Wis.) according to the manufacturer's instructions. Sections were deparaffinized, equilibrated in PBS, permeabilized with proteinase K (20 μg/ml in PBS), post-fixed in 4% paraformaldehyde, and incubated in TdT reaction mix (Promega) for 1 h at 37° C. in the dark. Slides were then washed in 2× saline-sodium citrate (SSC) buffer and counterstained with propidium iodide (1 μg/ml), and cover slipped with Vectashield mounting medium (Vector Laboratories, Burlingame, Calif.). Fluorescent images of apoptotic cells (green) and cell nuclei (red) were captured using a confocal microscope (Olympus 1X81).

RNA Preparation and DNA Microarray Analysis Total RNA was isolated from si-Scr- and si-hVDAC1-treated tumors (2 mice each) using an RNeasy mini kit (Qiagen) according to the manufacturer's instructions. Total RNA quality was analyzed using the Agilent RNA 6000 nano kit. The RNA integrity values obtained for total RNA extracted from si-Scr- and si-hVDAC1-treated tumors were 8-10 and 7-8.5, respectively. The targets for Affymetrix whole transcript expression microarray analyses were prepared using the Affymetrix GeneChip WT PLUS reagent kit according to the manufacturer's instructions and hybridized to Human Gene 1.0 ST microarrays. Data were acquired using the Affymetrix GeneChip algorithm (version 3.2). CEL files were imported to Partek® Genomics Suite® and all probes except control probes were preprocessed by RMA background correction, log 2 transformation and probeset summarization using median polish. Probesets having signal <5 in all samples were filtered out. Subsequently, global scaling was carried out by shifting the mean of each sample to the grand mean (i.e. in each sample, the mean signal was subtracted from each of the signals, and then the grand mean from all samples was added, such that all arrays eventually had the same mean signal). Differentially expressed genes were defined as those having FDR-adjusted t-test p-value <0.05, and two clusters were defined: upregulated and downregulated genes (linear fold change >2 and ←2, respectively). Each cluster was tested separately for enrichment of functional groups based on the GO system (Ashburner M et al., 2000. Nature genetics 25, 25-29.). Promoter analysis was performed using the DAVID (Huang et al., 2009) and Expander (Ulitsky I et al., 2010. Nature protocols 5, 303-322) software tools.

Quantitative Real-Time PCR (qRT-PCR)

Total RNA was isolated as described above. Complementary DNA was synthesized from 1 µg total RNA using a Verso cDNA synthesis kit (Thermo Scientific). Real-time fluorescent RT-PCR was performed using specific primers (KiCqStart Primers; Sigma Aldrich) in triplicate, using Power SYBER green master mix (Applied Biosystems, Foster City, Calif.). The levels of the target genes were normalized relative to β-actin mRNA levels. Samples were amplified by a 7300 Real Time PCR System (Applied Biosystems) for 40 cycles using the following PCR parameters: 95° C. for 15 seconds, 60° C. for 1 minute, and 72° C. for 1 minute. The copy numbers for each sample were calculated by the CT-based calibrated standard curve method. The mean fold changes (±SEM) of the three replicates were calculated. Primers designed for gene expression examination are listed in Table 3.

TABLE 3

Real-Time PCR Primers Used in this Study, Related to Experimental Procedures

| Gene | Primer sequences | SEQ ID NO: |
|---|---|---|
| β-Actin | Forward 5'-ACTCTTCCAGCCTTCCTTCC-3' | 26 |
| | Reverse 5'-TGTTGGCGTACAGGTCTTTG-3' | 27 |
| ALDH1L1 | Forward 5'-CCAAAGTCCTGGAGGTTGAA-3' | 28 |
| | Reverse 5'-TAACTCCAGGCCATCACACA-3' | 29 |
| BLPB (FABP7) | Forward 5'-AGTTTCCAGCTGGGAGAAGAG-3' | 30 |
| | Reverse 5'-CTTTGCCATCCCATTTCTGTA-3' | 31 |
| CAST | Forward 5'-CCAGAACCTATGCTGGTGGA-3' | 32 |
| | Reverse 5'-GGCTTTTTGGCTTGGTTGACT-3' | 33 |
| CS | Forward 5'-AGGAACAGGTATCTTGGCTCT-3' | 34 |
| | Reverse 5'-GGGGTGTAGATTGGTGGGAA-3' | 35 |
| c-Myc | Forward 5'-GTAGTGGAAAACCAGCAGCC-3' | 36 |
| | Reverse 5'-CCTCCTCGTCGCAGTAGAAA-3' | 37 |
| DLST | Forward 5'-TGCAAGGATGACTTGGTTACAG-3' | 38 |
| | Reverse 5'-CTTCTGCAACTGTGTCTCCAAC-3' | 39 |
| GFAP | Forward 5'-AAGCTCCAGGATGAAACCAAC-3' | 40 |
| | Reverse 5'-AGCGACTCAATCTTCCTCTCC-3' | 41 |
| GAPDH | Forward 5'-TGGAAGGACTCATGACCACA-3' | 42 |
| | Reverse 5'-ATGATGTTCTGGAGAGCCCC-3' | 43 |
| GLUT1 | Forward 5'-GGCCATCTTTTCTGTTGGGG-3' | 44 |
| | Reverse 5'-TCAGCATTGAATTCCGCCG-3' | 45 |
| Hif-1 α | Forward 5'-CTGACCCTGCACTCAATCAA-3' | 46 |
| | Reverse 5'-TCCATCGGAAGGACTAGGTG-3' | 47 |
| HK-I | Forward 5'-GTCTCAGTCCAGCACGTTTG-3' | 48 |
| | Reverse 5'-GAAACGCCGGGAATACTGTG-3' | 49 |
| IDH3a | Forward 5'-CCACATGGGACTTTTTGACC-3' | 50 |
| | Reverse 5'-TTACTCGGCGACAGATTTCC-3' | 51 |
| Ki-67 | Forward 5'-CTTTGGGTGCGACTTGACG-3' | 52 |
| | Reverse 5'-GTCGACCCCGCTCCTTTT-3' | 53 |
| LDH-A | Forward 5'-GCAGGTGGTTGAGAGTGCTT-3' | 54 |
| | Reverse 5'-GCACCCGCCTAAGATTCTTC-3' | 55 |
| MAP2 | Forward 5'-TCCAAAATCGGATCAACAGAC-3' | 56 |
| | Reverse 5'-AGAGCCACATTTGGATGTCAC-3' | 57 |
| Nanog | Forward 5'-TGGGATTTACAGGCGTGAGCCAC-3' | 58 |
| | Reverse 5'-AAGCAAAGCCTCCCAATCCCAAC-3' | 59 |
| N-Cadherin | Forward 5'-AGGGATCAAAGCCTGGAACA-3' | 60 |
| | Reverse 5'-TTGGAGCCTGAGACACGATT-3' | 61 |
| Nestin | Forward 5'-GAAACAGCCATAGAGGGCAAA-3' | 62 |
| | Reverse 5'-TGGTTTTCCAGAGTCTTCAGTGA-3' | 63 |
| Oct-3/4 | Forward 5'-GGGCTCTCCCATGCATTCAAAC-3' | 64 |
| | Reverse 5'-CACCTTCCCTCCAACCAGTTGC-3' | 65 |
| PCNA | Forward 5'-GCCGAGATCTCAGCCATATT-3' | 66 |
| | Reverse 5'-ATGTACTTAGAGGTACAAAT-3' | 67 |

TABLE 3-continued

Real-Time PCR Primers Used in this Study, Related to Experimental Procedures

| Gene | Primer sequences | SEQ ID NO: |
|---|---|---|
| PTPN12 | Forward 5'-TGACAGAGGAACGGGGGTAT-3' | 68 |
| | Reverse 5'-CGGCTGTGATCAAATGGCAG-3' | 69 |
| Sani11 | Forward 5'-AGTGGTTCTTCTGCGCTACT-3' | 70 |
| | Reverse 5'-CTGCTGGAAGGTAAACTCTGG-3' | 71 |
| Snail2 | Forward 5'-ACATACAGTGATTATTTCCCCGT-3' | 72 |
| | Reverse 5'-CGCCCCAAAGATGAGGAGTA-3' | 73 |
| SOX10 | Forward 5'-AGGAGAGGTCCGAGGAGGTG-3' | 74 |
| | Reverse 5'-CTCAGCTCCACCTCCGATAG-3' | 75 |
| SOX2 | Forward 5'-CCATGCAGGTTGACACCGTTG-3' | 76 |
| | Reverse 5'-TCGGCAGACTGATTCAAATAA-3' | 77 |
| SSEA-1 | Forward 5'-TGAAATAGCTTAGCGGCAAGA-3' | 78 |
| | Reverse 5'-GTGAATCGGGAACAGTTGTGT-3' | 79 |
| SUCLG2 | Forward 5'-AAGAGGTGGCTGCTTCAAAC-3' | 80 |
| | Reverse 5'-AGCCTAGATTTTCGGCCATC-3' | 81 |
| Tnc | Forward 5'-ATGAATCAGTGGATGGCACA-3' | 82 |
| | Reverse 5'-CCATTGAGTGCCTGGATCTT-3' | 83 |
| TUBB3 | Forward 5'-CTCAGGGGCCTTTGGACATC-3' | 84 |
| | Reverse 5'-CAGGCAGTCGCAGTTTTCAC-3' | 85 |
| Twist | Forward 5'-TCTTACGAGGAGCTGCAGAC-3' | 86 |
| | Reverse 5'-TATCCAGCTCCAGAGTCTCT-3' | 87 |
| Zeb1 | Forward 5'-TTCCTGAGGCACCTGAAGAG-3' | 88 |
| | Reverse 5'-GGTGTTCCATTTTCATCATGACC-3' | 89 |
| Zeb2 | Forward 5'-TAGTGTGCCCAACCATGAGT-3' | 90 |
| | Reverse 5'-TTGCATTCTTCACTGGACCA-3' | 91 |
| p53 | Forward 5'-AGGTTGGCTCTGACTGTACC-3' | 92 |
| | Reverse 5'-AAAGCTGTTCCGTCCCAGTA-3 | 93 |

Transcription Factors (TF) Profiling Array

Nuclear extracts were prepared from si-Scr- or si-hVDAC1-treated tumors using a Nuclear/cytosol fractionation kit (Biovision, Milpitas, Calif.) following the manufacturer's instructions. TF DNA-binding activity was analyzed as per the manufacturer's instructions (Signosis, Sunnyvale, Calif.). Briefly, a nuclear extract (~13 of protein) was added to a mixture of DNA sequences encoding 23 different TF-binding sites (BS) and incubated at 16° C. for 30 min. The samples containing the formed TF-DNA complexes were then separated from free DNA probes using an isolation column, with an aliquot (100 μl) being applied to the column and TF-DNA complexes being eluted with elution buffer (200 μl). A sample (95 μl) was then added to each well of a 96-well plate contained an immobilized complementary sequence to one of the 23 TFs. The plate was sealed and incubated overnight at 42° C. for hybridization. The plate was then washed three times, and developed using streptavidin conjugated-HRP and luminescence obtained following substrate addition was recorded using an Infinite M1000 microplate reader.

PLGA Encapsulation of siRNA

VDAC1 siRNA-loaded PEI-PLGA complexes were prepared by the solvent displacement method with some modifications, as previously reported (Fessi H et al., 1989. Int. J. Pharm. 55, 1-4; Das J et al., 2014. Toxicol Lett, 225, 454-66). A pre-formed complex of PEI (20 mg) dissolved in 1% of polyvinyl alcohol (PVA) and siRNA 360 μl siRNA solution (50 μM) was incubated for 30 min at 37° C. PLGA (50 mg) was dissolved in 1 ml acetone. To this organic mixture, 10 ml of aqueous solution containing 1% PVA (w/v) stabilizer was added in a drop-wise manner (0.5 ml/min). Subsequently, the pre-formed complexes containing siRNAs were added in a drop-wise manner. The mixtures were stirred continuously at room temperature until complete evaporation of the organic solvent. The nanoparticles were centrifuged at 15000 g (4° C. for 30 min) and the pellet was re-suspended in DEPC-water, washed three times and the resulting nanoparticles containing the siRNA-loaded suspension was stored at −20° C. until further use.

Neurosphere Formation

Conditions for neurosphere formation were as described previously (Rota L M et al. 2012. J Mammary Gland Biol Neoplasia 17: 119-123. Briefly, U-87MG, G7, MZ-18 and MZ-327 cells were treated with si-Scr or si-hVDAC1 (50 nM) and 24 h post-transfection, the cells ($10^5$) were cultured in 12-well plates coated with a soft agar (5%) layer prepared in neuronal stem cell medium, as described previously (Pollard et al. 2009, ibid). Following 24 h incubation at 37° C. in a 5% $CO_2$ atmosphere, the cultures were photographed.

Statistics and Data Analysis

The data was shown as the mean±SEM. of at least three independent experiments unless specified differently. Significance of differences was calculated by the two-tailed Student's t-test using the T Test function provided by Microsoft Excel. Statistically significance is reported at p<0.05 (*), p<0.01 () or p<0.001 (*). For survival analysis, Kaplan-Meier plots were used.

Figure 1B:
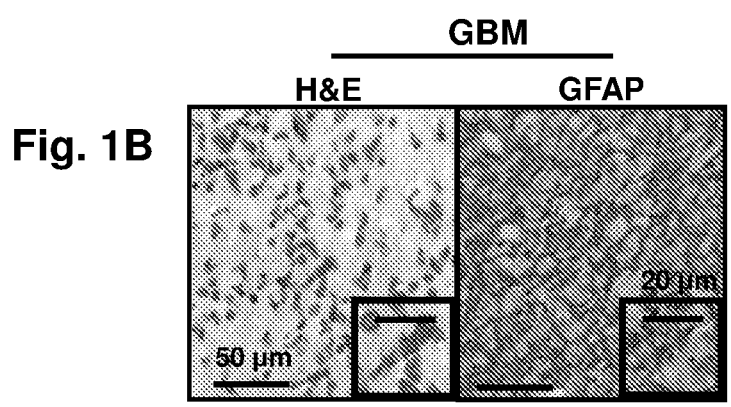
Figure 1C:
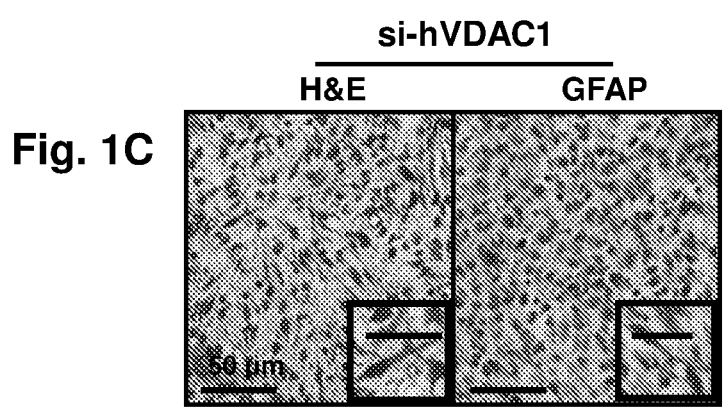
Figure 1D:
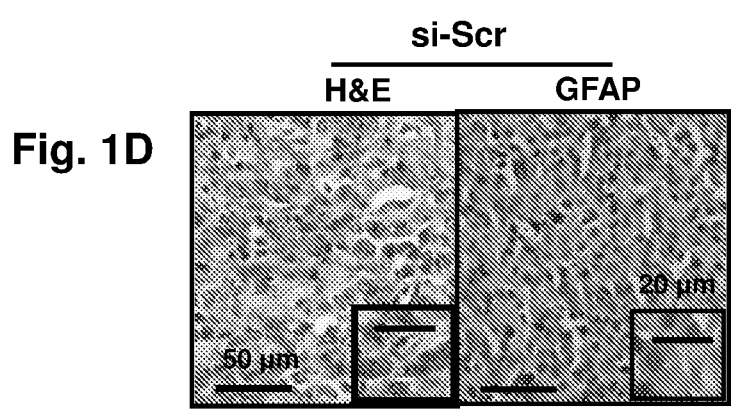
Figure 1E:
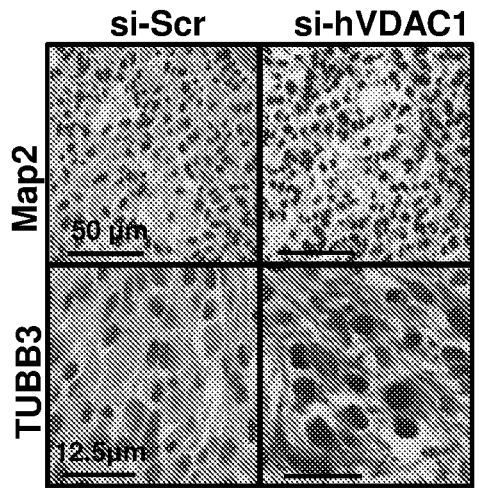

Example 1: VDAC1 Depletion Induces Changes in Cell Morphology and Expression of Differentiation Associated Proteins The levels of several differentiation markers in si-Scr and si-hVDAC1-treated tumors (TTs) were examined. As GBM is often considered a grade IV astrocytoma in which astrocytes lack normally recognizable features, human normal brain and GBM sections were hematoxylin and eosin (H&E) stained Normal brain showed astrocytes, a few small vessels and mainly fibrillary stroma (FIG. 1A). In contrast, GBM sections showed large irregular cells with atypical nuclei (FIG. 1B). Staining of normal brain for GFAP (glial fibrillary acidic protein), an intermediate filament protein expressed by central nervous system cells, including astrocytes, showed cells with long and marked processes (FIG. 1A). GFAP-staining of GBM sections showed cells with no processes, emphasizing the highly malignant nature of the cancer (FIG. 1B).

Figure 1F:
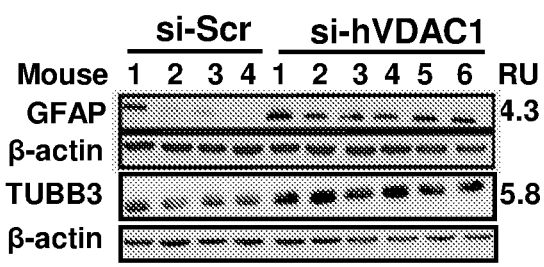
Figure 1G:
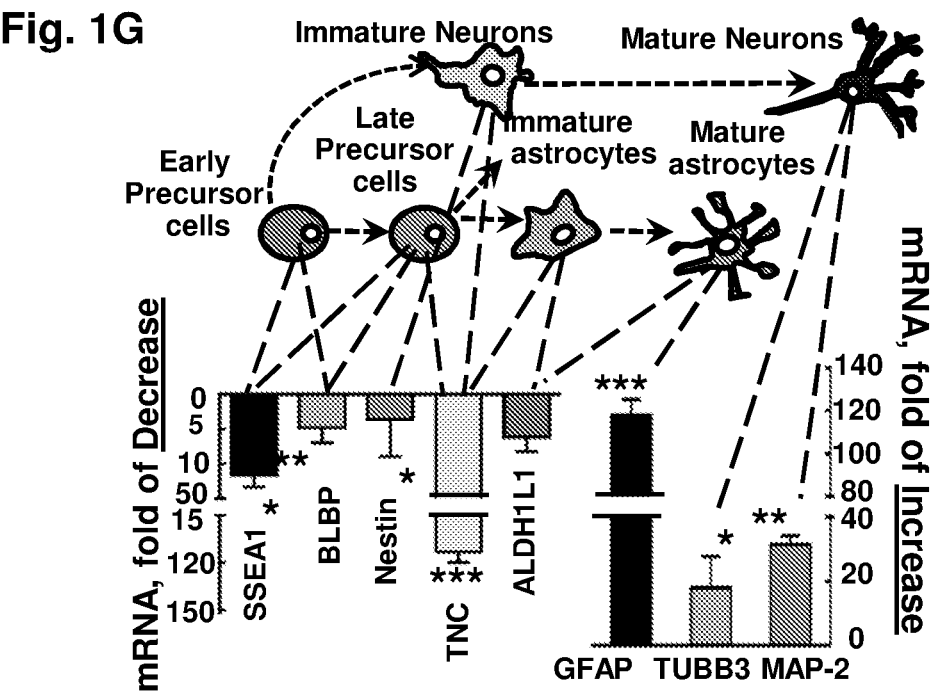

H&E-stained si-Scr-TT sections revealed cells with large nuclei (FIG. 1D), similar to those seen in GBM patients (FIG. 1B). In contrast, si-hVDAC1-TTs showed astrocyte-like cell morphology with long and marked processes (FIG. 1C), resembling normal brain tissue (FIG. 1A), with increased GFAP staining. Next immunostaining for the mature neuron markers, such as microtubule-associated protein 2 (MAP-2) and tubulin beta-III (TUBB3) (FIG. 1E, H and FIG. 2 A-C) was performed. Both were highly expressed in the si-hVDAC1-TTs. Increased GFAP and TUBB3 expression in the si-hVDAC1-TTs was also demonstrated by Western blotting (WB) (FIG. 1F). Similar results were obtained by qRT-PCR (FIG. 1G). These results indicate that si-hVDAC1 treatment induced morphological changes in tumor cells to resemble normal brain cells, and altered expression of neuronal markers, suggesting differentiation of tumor cells into astrocytes and neuron-like cells. To verify possible cell differentiation stages (Wiese S et al., 2012. Frontiers in pharmacology 3, 120) of si-hVDAC1-TTs, markers of cell differentiation stages were screened using qRT-PCR. Reductions (4-120-fold) in the levels of markers for early and late precursor cells, of immature astrocytes and neurons, and of the neuronal precursor and progenitor marker nestin, brain lipid binding protein (BLBP), stage-specific embryonic antigen 1 (SSEA1/CD15), tenascin C (TNC), and aldehyde dehydrogenase 1 L1 (ALDH1L1) was observed. At the same time, increase (15-120-fold) in the levels of markers associated with mature astrocytes and neurons (GFAP, TUBB3 and MAP2) were found (FIG. 1G).

Figure 1H:
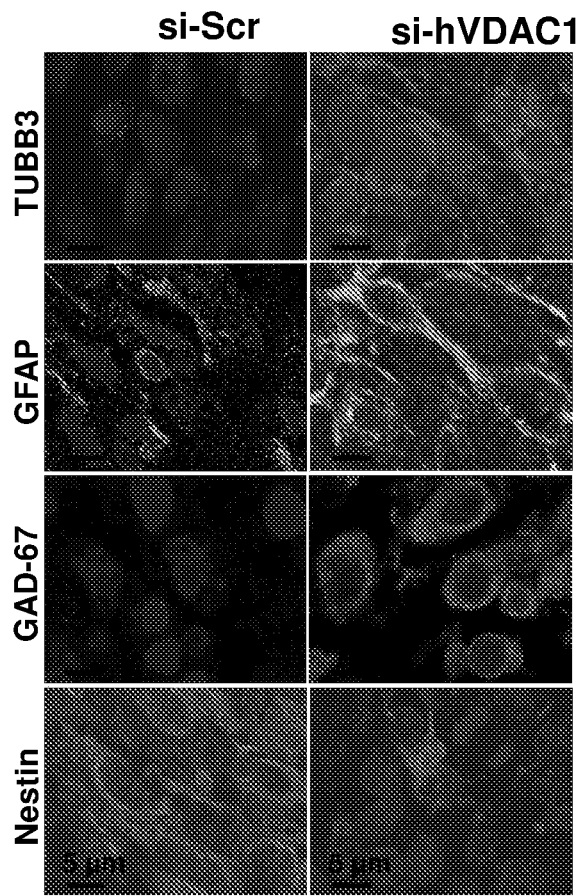
Figure 1I:
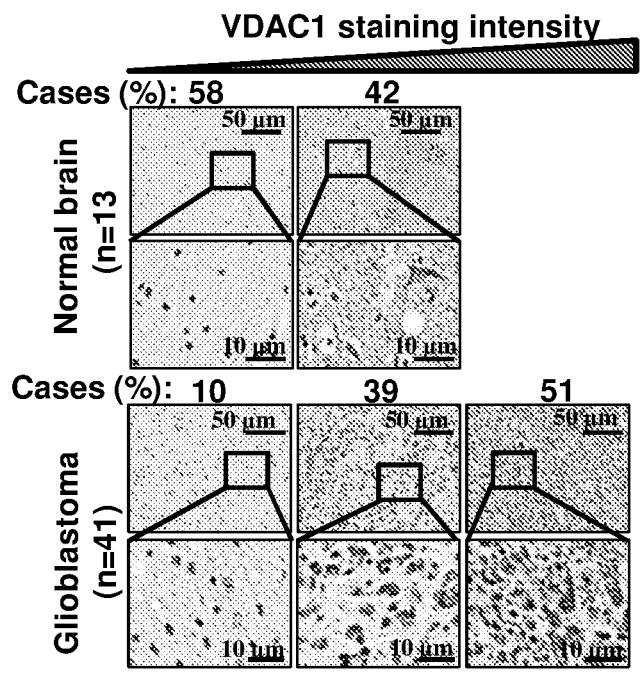

These findings were further supported by tumor section immunofluorescent staining. Nestin staining was highly decreased, while TUBB3, GFAP, and glutamate decarboxylase 1 (GAD1/GAD67), involved in GABA synthesis, were strongly stained (FIG. 1H). Similar results were obtained with U-118 cells (FIG. 2). The results indicate that GBM expressed precursor cells are capable of differentiation into neuronal lineages and that si-hVDAC1 tumor treatment led cells to differentiate towards mature astrocytes and neuron-like cells.

Example 2: VDAC1 Depletion Alters Transcription Factor (TF) Expression Profiles

To better understand the molecular mechanism underlying cell signaling and gene expression altered by treating the tumor with si-hVDAC1, shown to be leading to cell differentiation, changes in the expression levels of transcription factors (TFs) in the nuclear fraction were screened for. Cancer stem cell TF activation profiling plate array was used (FIG. 3A). si-hVDAC1-TTs expressed increased levels of tumor suppressor TFs, such as p53, Forkhead box O3 (FoxO3), PR domain-containing 14 (PRDM14) and signal transducer and activator of transcription 3 (STAT3). Expression levels of the major TFs p53, HIF-1α and c-Myc, known to regulate metabolism, cell growth, proliferation and differentiation (Yeung S J et al. 2008. Cellular and molecular life sciences: CMLS 65, 3981-3999) were significantly affected by si-hVDAC1 treatment. p53 levels were elevated in si-hVDAC1-TTs, while the expression levels of HIF-1α and c-Myc were reduced, as revealed by TF activation profiling assay, qRT-PCR, and immunoblotting (FIG. 3A-D). The level of AP-2, involved in tumorigenesis and possibly acting as a tumor suppressor, was decreased in si-hVDAC-TTs (FIG. 3A).

Expression levels of the canonical major TFs p53, HIF-1α (hypoxia-inducible factor 1 alpha) and c-Myc, known to regulate metabolism, cell growth, proliferation and differentiation (Yeung S J et al., 2008. Cellular and molecular life sciences: CMLS 65, 3981-3999), were also significantly affected by si-hVDAC1 treatment. p53 levels were elevated in si-hVDAC1-TTs, while the expression levels of HIF-1α and c-Myc were reduced, as revealed by TF activation profiling assay, qRT-PCR, and WB (FIG. 3A-D).

The results (FIGS. 1, 3) thus present a complex set of effects of VDAC1 depletion on a network of key regulators of cell metabolism, leading to a reprogramming of cancer cells towards differentiation.

Example 3: Tumor Treatment with Si-hVDAC1 Eliminates Glioblastoma Stem Cells (GSCs)

Figure 3H:
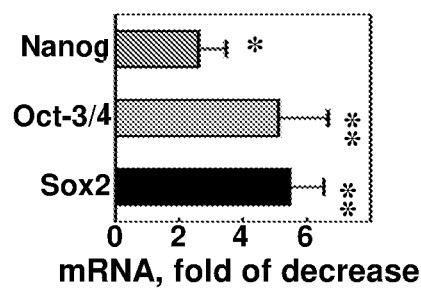
FIG. 3H: qRT-PCR analysis of Sox2, Oct3/4 and Nanog mRNA. Results=mean±SEM (n=3-5 tumors), p: *≤0.05; **≤0.001.
Figure 3I:
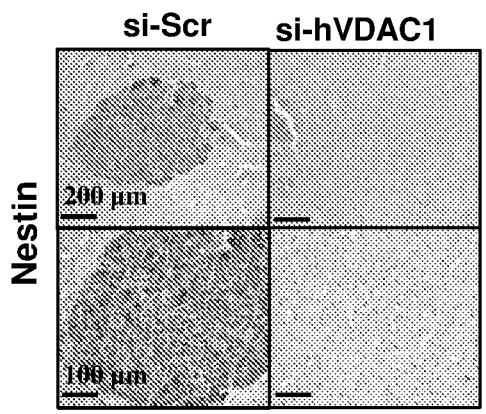
FIG. 3I: Orthotopic mouse model, representative Nestin-stained sections from brains engrafted with si-Scr- or si-VDAC1-treated U-87MG cells, 22 days after cell grafting.
Figure 4A:
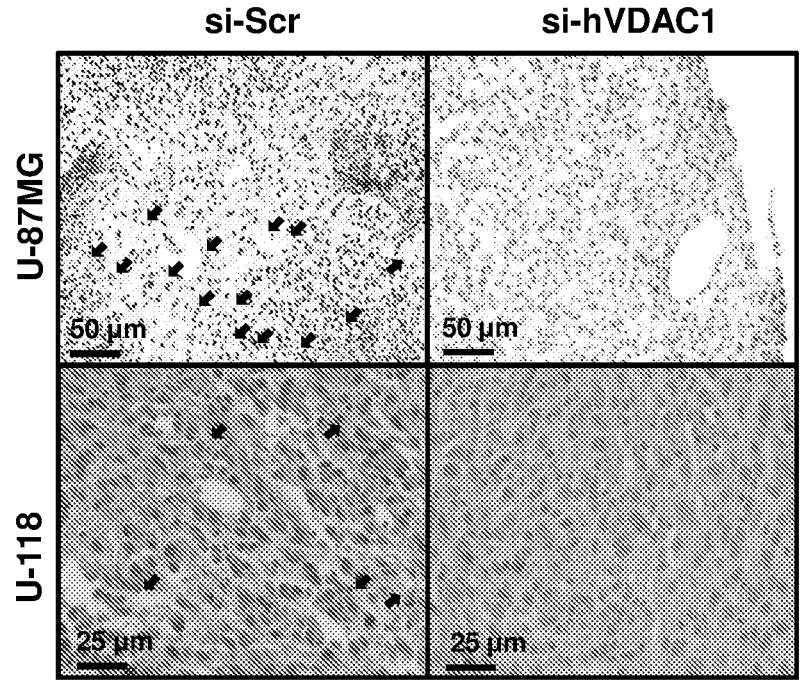
FIG. 4A: H&E staining of si-Scr- and si-hVDAC1-treated U-87MG and U-118 tumors, showing representative sections. Arrows point to muscle, indicting of tumor invasion.
Figure 4B:
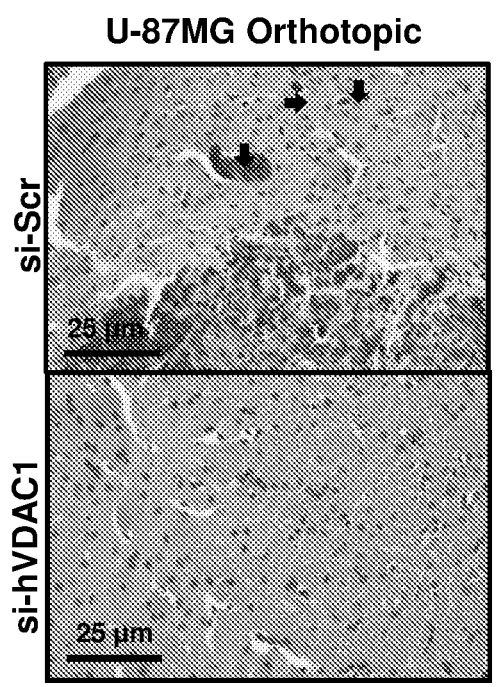
FIG. 4B: Representative IHC staining for Nestin of sections from brains engrafted with si-Scr- or si-VDAC1-treated U-87MG cells, 22 days after cells engraftation. Arrows point to tumor invasion in the brain.
Figure 4C:
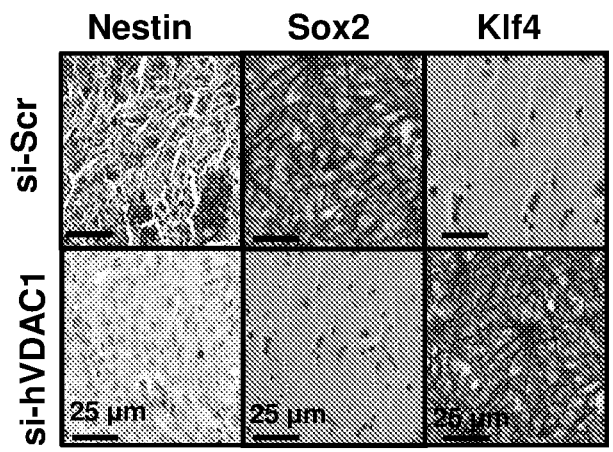
FIG. 4C: IHC of si-Scr- or si-hVDAC1-TT sections from U-118 tumors stained for stem cell markers, Nestin, Sox2 and Klf4.
Figure 4D:
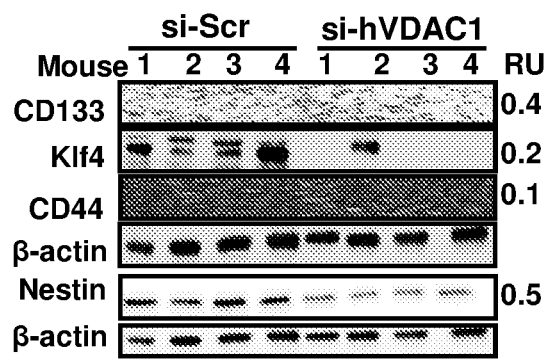
FIG. 4D: WB of CD133, Klf4, CD44 and Nestin levels in si-Scr- and si-hVDAC1-TTs sections from U118-derived tumors. RU=average relative levels.

The decrease in the levels of transcription factors (TFs) associated with stemness in the si-hVDAC1-TTs, such as Oct-3/4, AP1(Jun), Twist and Klf4 (FIG. 3A), and the increase in cell differentiation markers (FIG. 1) led to further analyses of the effects of VDAC1 depletion on the expression of GSCs-associated markers (FIG. 3E-H). Dynamic steadiness between self-renewing GSCs and differentiation is essential for GBM development (Bao et al., 2006) and invasion (FIG. 4A,B) (Singh et al., 2004). si-hVDAC1 treatment markedly decreased the expression of GSCs markers, such as CD133, Sox2, Klf4, Musashi, Nestin, NGFR, S100b and CD44, as evaluated by IHC and WB (FIG. 3E-G) and qRT-PCR, revealing decreases of several fold in Sox2, Oct3/4 and Nanog mRNA levels (FIG. 3H). Similar results were obtained with U-118 xenografts (FIG. 4C,D). The orthotopic tumors derived from si-Scr-treated U-87MG cells showed high levels of Nestin in patches (FIG. 3I), pointing to GSCs niches. No staining was obtained in brain injected with si-VDAC1 U-87MG-treated cells. Thus, si-VDAC1 tumor treatment resulted in apparent "disappearance" of GSCs (FIG. 3). Without wishing to be bound by any specific theory or mechanism of action, the reduction in the GSCs number is attributed to the promoted differentiation (FIG. 1). Arrest of cell proliferation caused by VDAC1 silencing may also contribute.

Figure 9A:
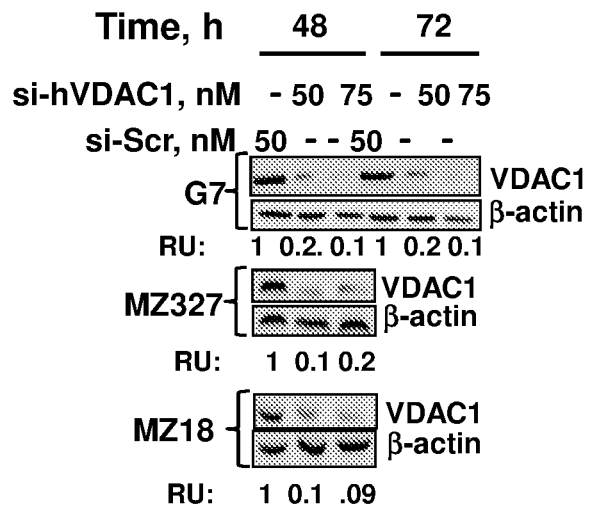
FIG. 9 shows the effect of si-hVDAC1 and si-Scr on neurosphere formation. G7, MZ-18 and MZ327 cells were treated with si-Scr or si-hVDAC1 and after 48 and 72 h, the cells were analyzed for VDAC1 levels (FIG. 9A) or cell growth using SRB (FIG. 9B), as described in the Examples section hereinbelow. Results are the mean±SEM (n=3); p:≤0.001; *≤0.0001.
FIG. 9C shows Neurosphere formation in si-Scr- or si-hVDAC1-treated U-87MG, G7, MZ-18 and MZ-327 cells in stem cell-specific medium.
Figure 9B:
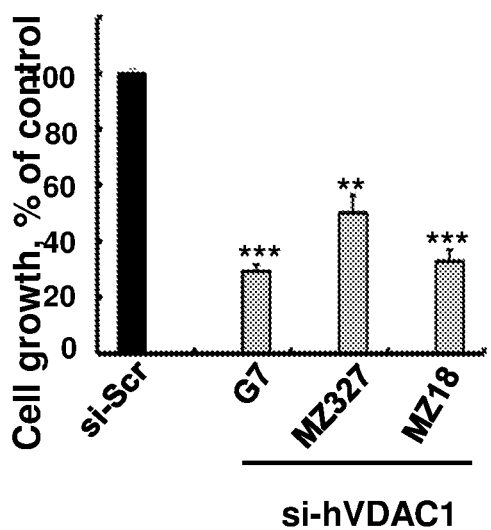
Figure 9C:
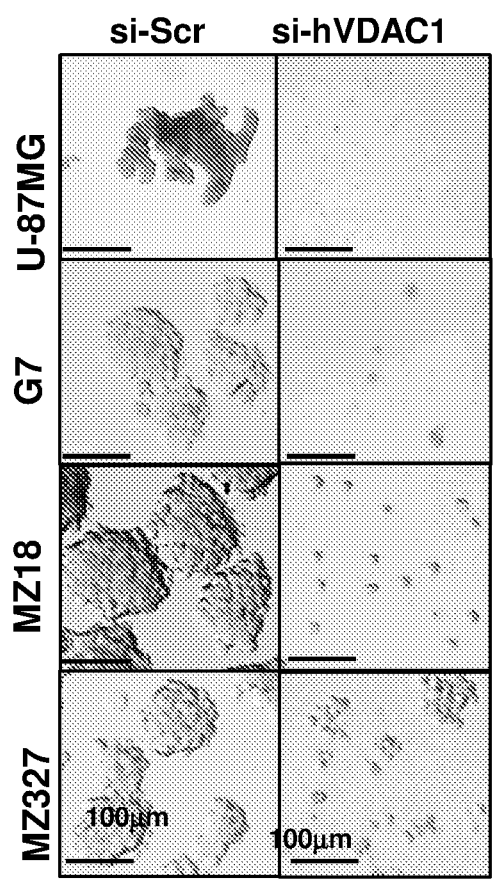

The effect of si-hVDAC1 treatment on stem cells was also demonstrated by analyzing neurosphere formation using neuro-stem cell medium. U-87MG, the glioma-derived G7 stem cell line and the human GBM patient-derived cell lines, MZ-18 and MZ-327 were treated with si-Scr or si-hVDAC1, showed decreased VDAC1 levels and inhibited cell growth (FIG. 9A-B). Neurospheres were formed in the si-Scr-treated but not in si-hVDAC1-treated cells (FIG. 9C). The reduced potential of neurosphere formation by reducing VDAC1 levels suggests a decrease in GSC levels upon metabolic reprogramming.

Example 4: Effect of hVDAC1 Silencing on Epithelial to Mesenchymal Transition (EMT)

Figure 3J:
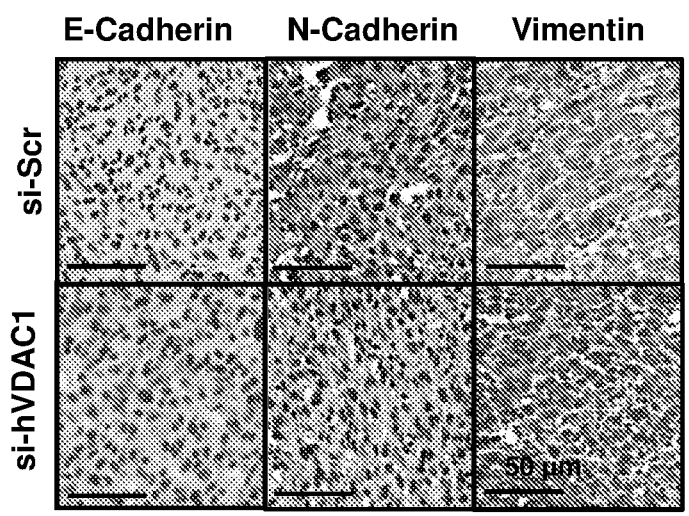
FIG. 3J: Typical IHC staining of sections from si-Scr- or si-hVDAC1-TTs for E-cadherin, N-cadherin and Vimentin.
Figure 3K:
FIG. 3K: WB of E-cadherin and vimentin in U-87MG si-Scr- and si-hVDAC1-TTs.
Figure 3L:
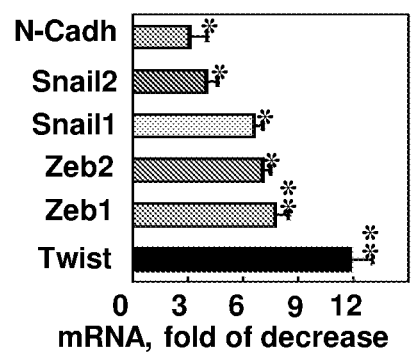
FIG. 3L: qRT-PCR analysis of Twist, Zeb1, Zeb2, Snail1, Snail2 and N-cadherin (N-Cadh) mRNA levels in si-Scr- and si-hVDAC1-TTs. Results are the mean±SEM (n=3-5, p: *≤0.05; **≤0.001). RU=average relative levels.

The tumor metastatic potential is attenuated by the epithelial to mesenchymal transition (EMT) (Math S A et al., 2008. Cell 133, 704-715). To follow EMT, si-Scr- and si-hVDAC1-TTs were analyzed for the expression of epithelial and mesenchymal cell markers (FIG. 3J-L). IHC staining of si-hVDAC1-TTs showed a decrease in the mesenchymal cells markers N-cadherin (type I cell-cell adhesion glycoproteins) and vimentin (intermediate filaments) and an increase in E-cadherin, an epithelial cell marker (Agiostratidou G et al., 2007. Journal of mammary gland biology and neoplasia 12, 127-133), as compared to their levels in si-Scr-TTs (FIG. 3J) Similar results were obtained for E-cadherin and vimentin by WB (FIG. 3K) and qRT-PCR showing the mesenchymal markers Twist, Zeb1, Zeb2, Snail1, Snail 2, and N-cadherin (Barriere G et al., 2014. Annals of translational medicine 2, 109) to be decreased 3-12-fold in si-VDAC1-TTs (FIG. 3L). These results show that EMT was reversed in si-hVDAC1-TTs and that this attenuated the invasive potential of GBM cells (FIG. 4A,B).

Figure 5A:
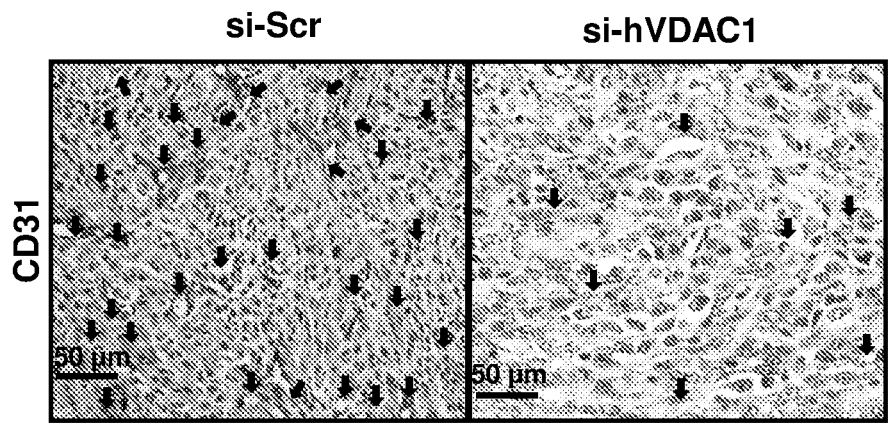
FIG. 5A: Representative IHC staining of endothelial cells associated with blood vessels in sections from si-Scr- and si-hVDAC1-TTs derived from U-87MG tumors, as revealed using anti-CD31 antibodies. Black arrows point to blood vesicles (bar=50 μm).
Figure 5B:
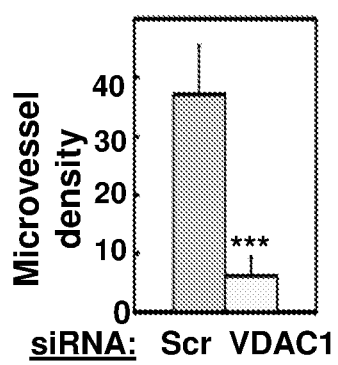
FIG. 5B: Quantitative analysis of microvessel density (MVD) per unit area expressed as means±SEM, p<0.001; si-Scr versus si-hVDAC1 (n=5 animals from each group).

Example 5: Effect of hVDAC1 Silencing on Angiogenesis, Tumor-Associated Macrophage and Extracellular Matrix A solid tumor requires blood supply to continue growing and thus promotes angiogenesis, with GBM being highly angiogenic and invasive (Bai et al., 2011, ibid). Immunostaining of endothelial cells from si-hVDAC1-TT for CD31 showed a major decrease in the number of blood vessels, with quantitation of microvessel density (MVD) revealing a near 80% decrease (FIG. 5A,B).

Figure 4E:
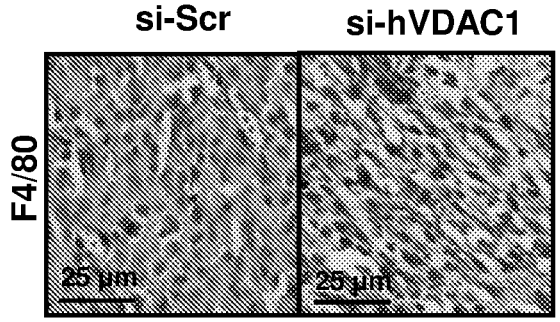
FIG. 4E: IHC staining of tumor sections derived from U-87MG tumors treated with si-Scr- or si-hVDAC1 using anti-F4/80, tumor associate macrophages marker.
Figure 5C:
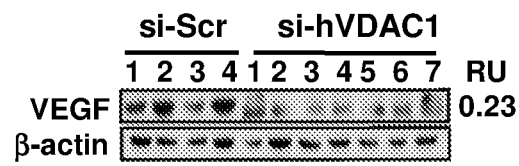
FIG. 5C, D: Immunoblotting (FIG. 5C) and IHC staining (FIG. 5D) of tumor sections derived from U-87MG tumors treated with si-Scr- or si-hVDAC1 using anti-VEGF antibodies.
Figure 5D:
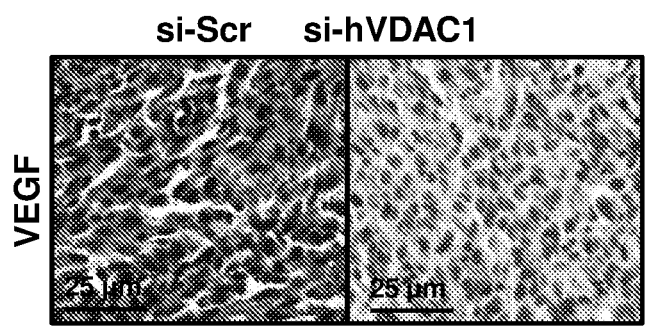
FIG. 5 demonstrates inhibition of angiogenesis in si-hVDAC1-TTs with altered expression of endothelial cell markers CD31.

In GBM, as in many other cancers, high levels of vascular endothelial growth factor (VEGF), activating highly expressed VEGF receptors in tumor endothelial vessels to stimulate angiogenesis, are expressed. VEGF level was dramatically decreased in si-hVDAC1-TTs (FIG. 5C, D). IHC analysis of si-hVDAC1-TTs also showed decreased levels of the tumor-associated macrophage specific marker, cell surface glycoprotein F4/80 (FIG. 4E). Similarly, DNA micro array analysis (Table 4) also showed that si-hVDAC1 treatment affected the expression of angiogenesis-, EMT- and invasion-related genes, reducing VEGF/A, TGFβ, Hif-1α, metalloproteinases, extracellular matrix and cell adhesion components, while increasing angiogenic and MMP inhibitors.

TABLE 4

Selected genes associated with tumor oncogenic properties differentially expressed in si-Scr and si-hVDAC1-treated tumors, as identified by DNA microarray analysis

| Invasive related genes | si-hVDAC1- vs. si-Scr-treated tumors Fold Change | p-value | Function |
|---|---|---|---|
| MMP transcription and function inhibitors | | | |
| ID4-inhibitor of DNA binding 4 | 6.10 | 4.4E−04 | Transcriptional negative regulator of basic helix-loop-helix TFs |
| TIMP1-metallopeptidase inhibitor 1 | −5.80 | 9.0E−05 | Inhibitor of several MMPs, including MMP-3, MMP7-13 and MMP16 |
| TIMP2-metallopeptidase inhibitor 2 | −4.00 | 3.4E−03 | Inhibitor of several MMPs, including MMP-1-3, 7-10, 13-16, 19 |
| TIMP3-metallopeptidase inhibitor 3 | −4.71 | 2.3E−03 | Inhibitor of several MMPs, including MMP-1-3, 7, 9, 13-15 |
| MMP proteins | | | |
| MMP2-matrix metallopeptidase 2 | −7.9 | 2.3E−03 | Metalloproteinase cleaving gelatin type I and collagen types IV, V, VII, X |
| MMP16-matrix metallopeptidase 16 | −2.3 | 7.9E−03 | Metalloproteinase cleaving collagen type III and fibronectin |
| ADAM9-Disintegrin and metallo-proteinase domain-containing protein 9 | −11.0 | 5.0E−04 | Membrane-anchored zinc protease implicated in cell-cell and cell-matrix interactions |
| ADAM12-Disintegrin and metallo-proteinase domain-containing protein 12 | −7.1 | 6.0E−04 | Membrane-anchored zinc protease involved in cell-cell and cell-matrix interactions |
| ECM and integrin genes | | | |
| LAMB1-laminin, beta 1 chain | −4.2 | 9.0E−03 | Component of the ECM |
| LAMC1-laminin, gamma 1 | −5.1 | 6.6E−04 | Component of the ECM |
| ITGA2-integrin, alpha 2 | −4.9 | 2.6E−04 | Mediates cell matrix and cell-cell interactions |
| ITGA3-integrin, alpha 3 (subunit of VLA-3) | −7.4 | 5.3E−04 | Mediates cell matrix and cell-cell interactions |
| ITGA5-integrin, alpha 5 (fibronectin receptor) | −4.2 | 4.7E−03 | Mediates cell matrix and cell-cell interactions |
| ITGB1BP1-integrin beta 1 binding protein 1 | −4.2 | 3.7E−04 | Mediates cell matrix and cell-cell interactions |

TABLE 4-continued

Selected genes associated with tumor oncogenic properties differentially expressed in si-Scr and si-hVDAC1-treated tumors, as identified by DNA microarray analysis

| | si-hVDAC1- vs. si-Scr-treated tumors | | |
|---|---|---|---|
| Invasive related genes | Fold Change | p-value | Function |
| ITGB3BP-integrin beta 3 binding protein | −6.6 | 1.2E−03 | Mediates cell matrix and cell-cell interactions |
| CD44-Hyaluronic acid receptor | −3.1 | 3.8E−04 | Receptor for hyaluronic acid |
| CD99-Transmembrane glycoprotein | −9.0 | 2.1E−04 | Inhibits cell-extracellular matrix adhesion |
| CD164-Sialomucin core protein 24 (endolyn) | −21.2 | 2.1E−04 | Cell adhesion molecule |
| Angiogenesis | | | |
| VEGFB-Vascular endothelial growth factor B | 4.5 | 3.4E−04 | Growth factor for endothelial cells of newly formed blood vessels |
| VEGFC-Vascular endothelial growth factor C | −2.1 | 6.3E−05 | Growth factor for lymphatic endothelial cells |
| NRP1-Neuropilin 1 | −4.7 | 1.8E−04 | Membrane co-receptor for both VEGF and Semaphorin, also functions in axon guidance, cell survival, migration, and invasion |
| TGFB1-Transforming growth factor, beta 1 | −3.1 | 2.3E−04 | Growth factor controlling proliferation, differentiation and more cell functions |
| TGFBR1-Transforming growth factor, beta receptor 1 | −2.2 | 1.1E−03 | Co-receptor for TGFBR2 activated by bound TGFβ |
| TGFBR2-Transforming growth factor, beta receptor 2 | −6.7 | 1.5E−04 | Constitutively active co-receptor TGFBR1 of bound TGFβ |
| CD109-tumor endothelial cells marker | −12.3 | 2.0E−04 | GPI-linked cell surface antigen |
| Angiogenic inhibitors | | | |
| HIF1AN-hypoxia inducible factor 1, alpha subunit inhibitor | −2.3 | 6.8E−04 | Preventing interaction of HIF-1 with transcriptional co-activators |
| SERPINF1-Serpin peptidase inhibitor, clade F | 2.3 | 9.2E−03 | Inhibitor of neovascularization and tumorigenesis and activator of neurotrophic functions |
| THBS1-Thrombospondin 1 | 10.4 | 3.2E−03 | Inhibitor of neovascularization and tumorigenesis |

Example 6: Modified Gene Expression Profile of Si-hVDAC1-TTs

Affymetrix DNA microarray analysis was used to identify patterns of gene expression in si-hVDAC1-versus si-Scr-TTs (FIG. 6). Such analysis revealed 4,493 genes the expression of which was significantly changed (≥2-fold change, false discovery rate <0.05), which were clustered to 1,998 down-regulated (cluster 1) and 2,495 up-regulated genes (cluster 2) in the si-hVDAC1-TTs (FIG. 6A). Functional analysis based on the Gene Ontology (GO) system revealed alterations in key functions and pathways related to cancer tumorigenicity (FIG. 6B). The down-regulated group (FIG. 6B) was highly enriched for genes related to cell cycle, such as the cell cycle mitotic phase and DNA repair, and to the mitochondrion, such as Kreb's cycle and oxidative phosphorylation (OXPHOS), in agreement with IHC and WB results (data not shown). The up-regulated group (FIG. 6B) was enriched for genes related to the regulation of transcription and the WNT pathway. Remarkably, 67 genes were associated with neuronal differentiation.

Figure 6A:
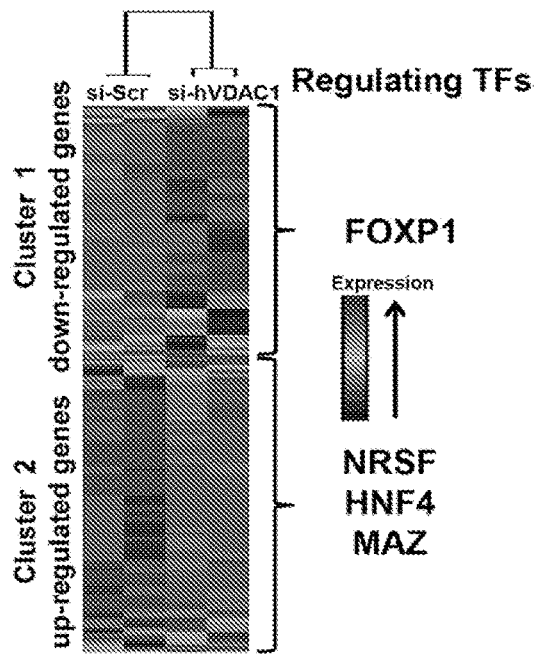
FIG. 6A: Clustering of the 4,493 differentially expressed genes: Down- (cluster 1, 1998 genes) and up-regulated (cluster 2, 2495 genes). Black to gray colors indicates expression level. Promoter analysis indicate binding sites enrichment for FOXP1 (367 genes, p=3.4×10$^{-20}$) in cluster 1, and NRSF (1,310 genes, p=1.3×10$^{-84}$), HNF4 (1,161 genes, p=5.8× 10$^{-38}$) and MAZ (678 genes, p=1.2×10$^{-22}$) in cluster 2.
Figure 6B:
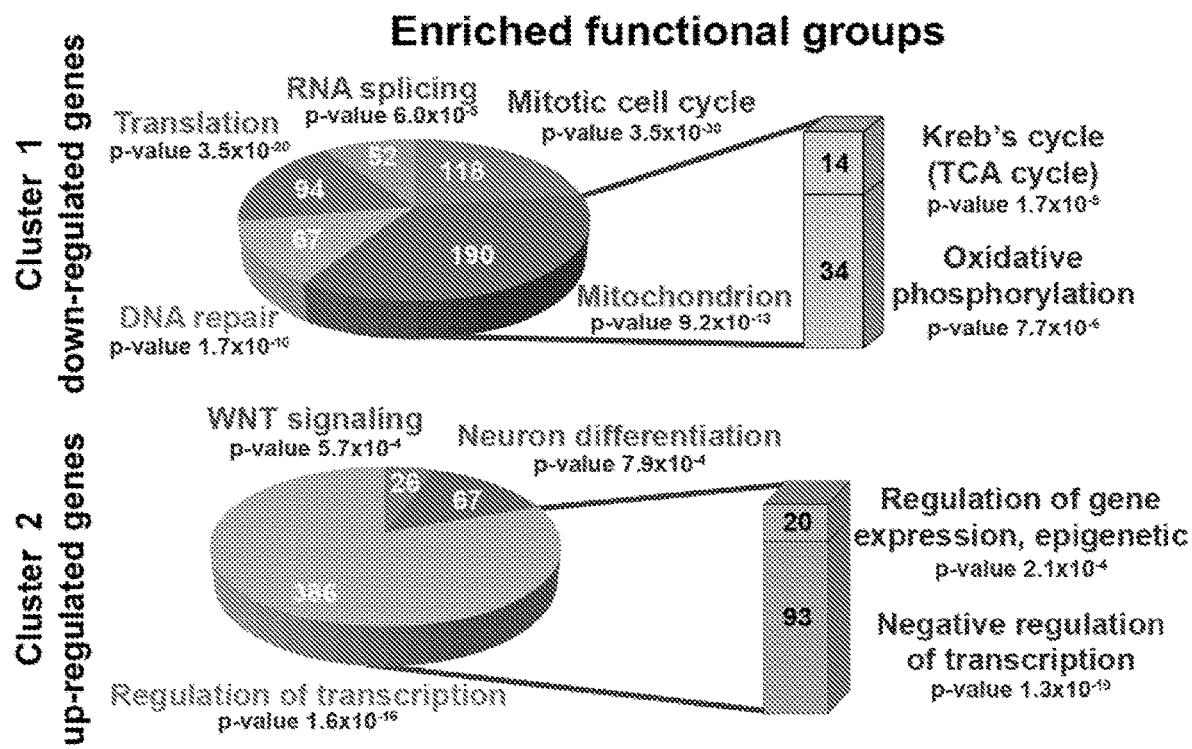
FIG. 6B: Functional analysis of cluster 1 and 2 based on the gene ontology (GO) system. The number of genes associated with the indicated function is presented.
Figure 6C:
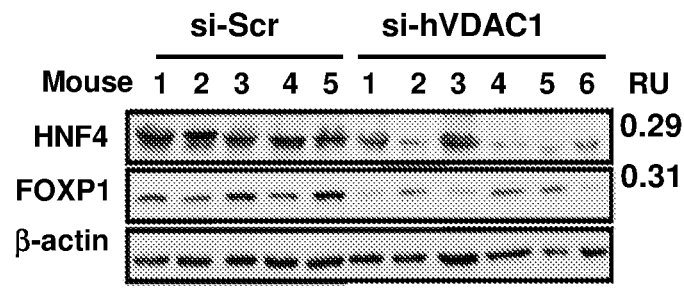
FIG. 6C: WB of HNF4 and FOXP1 in si-Scr- and si-hVDAC1-TTs. RU=Average relative level.
Figure 6D:
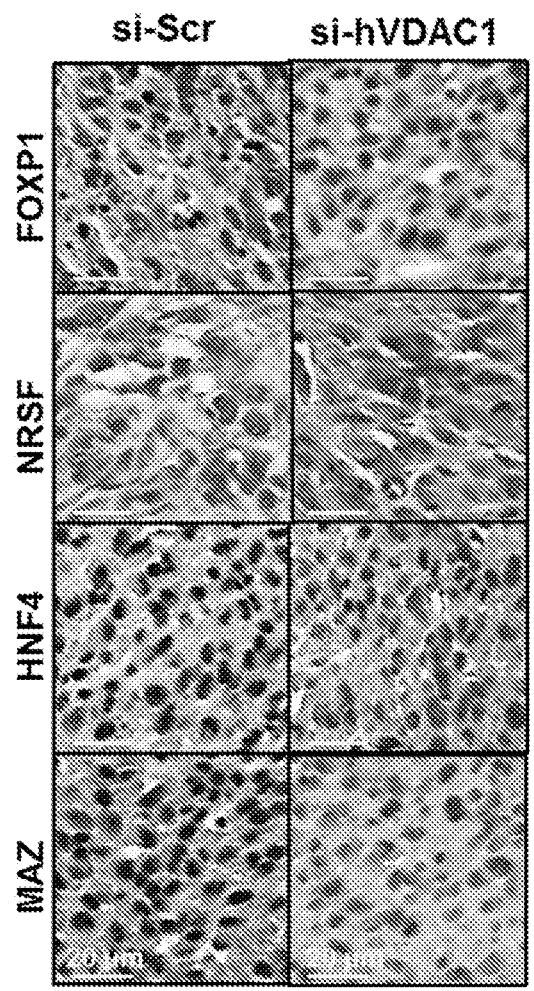
FIG. 6D: IHC staining of si-Scr- or si-hVDAC1-TTs using antibodies specific to the TFs identified in A: FOXP1, NRSF, HNF4 and MAZ.
Figure 6E:
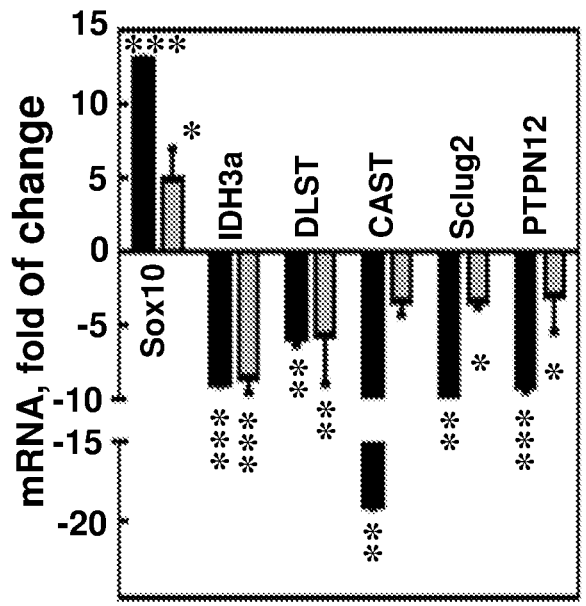
FIG. 6E: Levels of Sox10, DLST, CAST, Sclug2 and PTEN12 levels in si-Scr- and si-hVDAC1-TTs, as analyzed using qRT-PCR (Black bars) and DNA microarray (grey bars). Results are the mean±SEM (n=3-5, p: *≤0.05; **≤0.001).
Figure 7A:
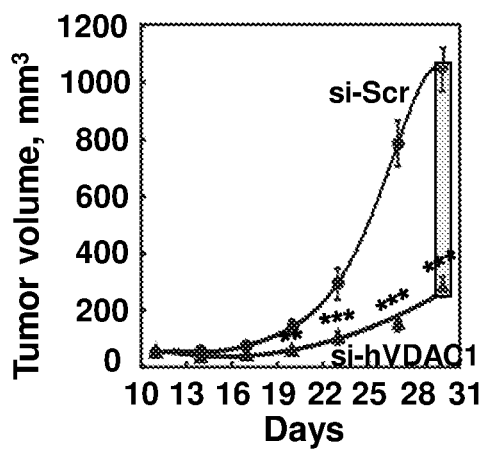
FIG. 7A: U-87MG cells were s.c. inoculated into athymic nude mice. On day 13, the mice were divided into 2 groups and xenografts were injected every three days with si-Scr (●, 8 mice) or si-hVDAC1 (▲, 16 mice) to a final concentration of 50-60 nM (*p≤0.0001).
Figure 7B:
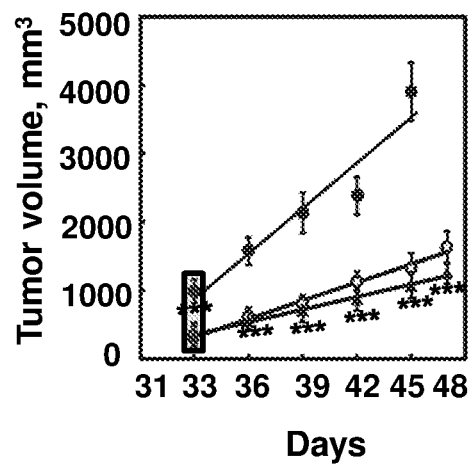
FIG. 7B: On day 33, the si-hVDAC1-treated mice were sub-divided into 2 groups (8 mice each). One group (▲) continued si-hVDAC1 treatment, the other switched to si-Scr (○) treatment. (●) indicates original si-Scr group.
Figure 7C:
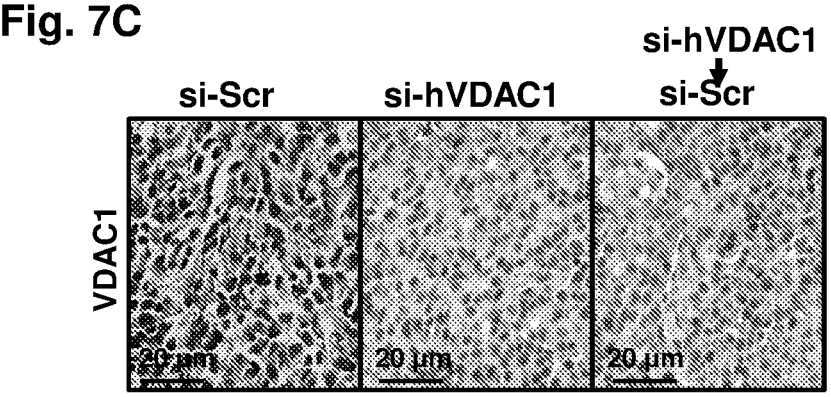
FIG. 7C: Representative sections from Scr- and si-hVDAC1-TTs IHC-stained for VDAC1.
Figure 7D:
FIG. 7D: WB of VDAC1 in si-Scr- and si-hVDAC1-TTs. RU=relative units.
Figure 7E:
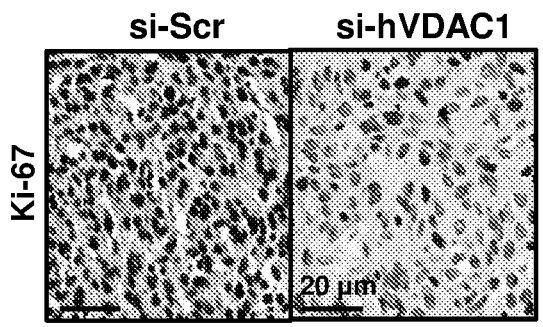
FIG. 7 demonstrates si-hVDAC1 inhibition of tumor growth in vivo.
FIG. 7G: qRT-PCR analysis of Ki-67 and PCNA mRNA levels isolated from si-Scr-(black bars) and si-hVDAC1 (gray bars)-TTs. Results=mean±SEM (n=3-5), p: ≤0.001; *≤0.0001).
FIG. 7J: Orthotopic GBM, MRI imaging of brains 33 days after engrafted with U-87MG cells treated with si-Scr or si-VDAC1.
FIG. 7K: Calculated tumor volume after 22 (black bars) and 33 days (grey bars). Results=mean±SEM (n=4-5), p: **≤0.00001.
FIG. 7L: Sections of paraffin-embedded U-87MG xenograft from si-Scr- or si-hVDAC1-TTs stained with PI or TUNEL showing no cell death.
Figure 7F:
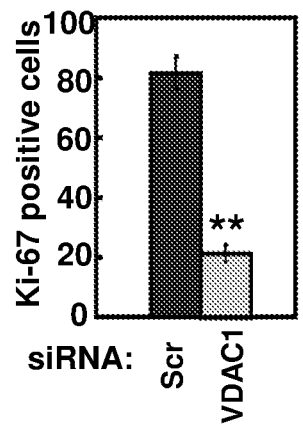
Figure 7G:
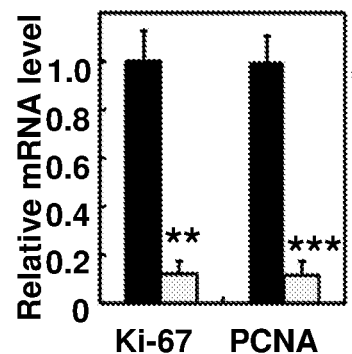
Figure 7H:
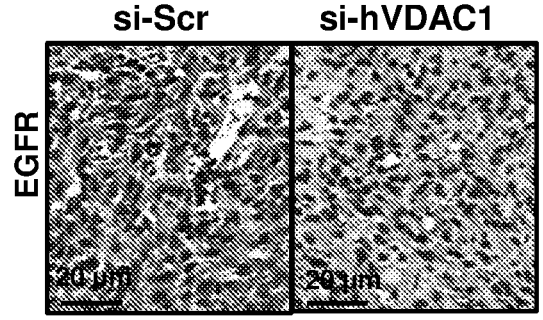
Figure 7I:
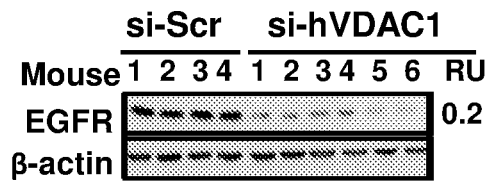

Promoter analysis of the differentially expressed genes in si-hVDAC1-TTs revealed enrichment of several TF-binding sites (BSs). The down-regulated group showed high enrichment in genes encoding proteins with BSs for FOXP1 (Forkhead box protein P1). FOXP1 may act either as a transcriptional activator or repressor and as an oncogene or tumor suppressor (Katoh M et al., 2013. Cancer letters 328, 198-206). The analysis presented herein suggests that FOXP1 acts as a transcriptional activator and as an oncogene, as its level was down-regulated (FIG. 6C,D). In the up-regulated group, TF-BSs for three main TFs were highly enriched (FIG. 6A,B). NRSF (neuron-restrictive silencer factor), a transcriptional repressor of neuronal genes in non-neuronal cells (Lunyak V V and Rosenfeld M G., 2005. Cell 121, 499-50), was down-regulated in si-hVDAC1-TTs (FIG. 6D), allowing the cells to differentiate to neurons. The same was true for HNF4 (hepatocyte nuclear factor 4), a central regulator of hepatocyte differentiation and function (Watt A J et al., 2003. Hepatology 37, 1249-1253), and MAZ (myc-associated zinc-finger), which regulates c-Myc and HRAS (Cogoi et al., 2010). Together, HNF4 and MAZ co-regulate neural stem-cell differentiation (Wang et al., 2013). Down-regulation of HNF4 and MAZ in si-hVDAC1-TTs (FIG. 6C, D) is in agreement with differentiation of GBM cells in these tumors (FIG. 1).

Table 5 presents selected genes from the down-regulated (cluster 1) and up-regulated (cluster 2) groups (see also FIG. 5), representing major functional groups, i.e. associated with cell cycle, DNA repair, metabolism (TCA cycle, oxidative phosphorylation), regulation of gene expression, Wnt signaling or neuronal differentiation. For each gene, the gene symbol and name, linear fold of change in expression and p-value are indicated. Negative numbers represent down-regulation.

TABLE 5

List of selected genes differentially expressed between si-Scr- and si-hVDAC1-treated tumors, as identified by DNA microarray analysis

| Gene | si-hVDAC1- vs. si-Scr-treated tumors Fold-Change | p-value | Function |
|---|---|---|---|
| Cluster 1, down-regulated genes | | | |
| Cellular metabolism and survival regulation | | | |
| EGFR-Epidermal growth factor receptor | −2.78 | 4.9E−03 | EGF receptor, activates the oncogenic Ras signaling cascade |
| MDM2-p53 binding protein homolog | −7.97 | 2.2E−03 | ligase, regulates p53 level via degradation |
| HIF1A-Hypoxia inducible factor 1, alpha subunit | −13.34 | 2.2E−03 | Transcription factor, master regulator of response to hypoxia |
| Cell cycle | | | |
| CCNB1-cyclin B1 | −4.61 | 1.9E−03 | Essential for the control of the cell cycle at G2/M (mitosis) |
| CCNG1-cyclin G1 | −19.46 | 2.8E−05 | Associated with G2/M phase arrest in response to DNA damage in the TP53 pathway |
| DNA repair | | | |
| ATM-serine/threonine kinase | −3.10 | 3.8E−03 | Activates checkpoint signaling upon double strand breaks |
| BRCA2-Breast cancer 2 | −4.20 | 8.9E−04 | Involved in double-strand break repair and/or homologous recombination |
| TP53BP1-Tumor protein p53 binding protein 1 | −3.10 | 1.3E−03 | Enhances TP53-mediated transcriptional activation. |
| TP53BP2-Tumor p53 binding protein 2 | −2.35 | 1.6E−03 | Regulates TP53 by enhancing its DNA binding |
| TCA cycle | | | |
| IDH3A-Isocitrate dehydrogenase 3 alpha subunit | −9.00 | 6.1E−04 | TCA cycle enzyme involved in energy production |
| SDHB-Succinate dehydrogenase complex, subunit B, | −4.86 | 4.5E−03 | Involved in energy production |
| Oxidative phosphorylation | | | |
| NDUFB6-NADH dehydrogenase (ubiquinone) 1 beta sub-complex, 6, | −4.69 | 3.0E−04 | Electron transport component, energy production |
| ATP5B-ATP synthase, beta subunit | −2.77 | 1.0E−03 | Uses mitochondrial $\Delta\Psi$ for ATP synthesis |
| COX6C-Cytochrome c oxidase, subunit VIc | −11.29 | 2.5E−03 | Electron transport component, energy production |
| Cluster 2, up-regulated genes | | | |
| Negative regulation of gene expression | | | |
| ID4-Inhibitor of DNA binding 4 | 6.10 | 4.4E−03 | Does not bind DNA directly, rather inhibits activity of other transcription factors |
| FOXP4-Forkhead box P4 | 5.20 | 9.2E−03 | Transcriptional repressor that represses lung-specific expression |
| Wnt signaling | | | |
| FZD1-Frizzled homolog 1 | 4.47 | 8.2E−03 | Receptor for Wnt proteins |
| WNT1-Wingless-type MMTV integration site family, member 1 | 6.19 | 4.8E−03 | Ligand for members of the frizzled family receptors |
| Neuron differentiation | | | |
| UNC5B-HOMOLOG B, NETRIN RECEPTOR | 2.88 | 1.4E−03 | A netrin-1 receptor, thought to mediate the netrin-1 chemorepulsive effect |
| CDK5R1-cyclin-dependent kinase 5, regulatory subunit 1 (p35) | 6.11 | 3.5E−04 | Involved in proper development of the central nervous system |
| MANF-Mesencephalic astrocyte-derived neurotrophic factor | 4.48 | 9.2E−04 | Involved in ER stress-induced death and cell proliferation |

Example 7: VDAC1 Depletion Reverses Reprogrammed Cancer Cell Metabolism

Figures 8A, 8B:
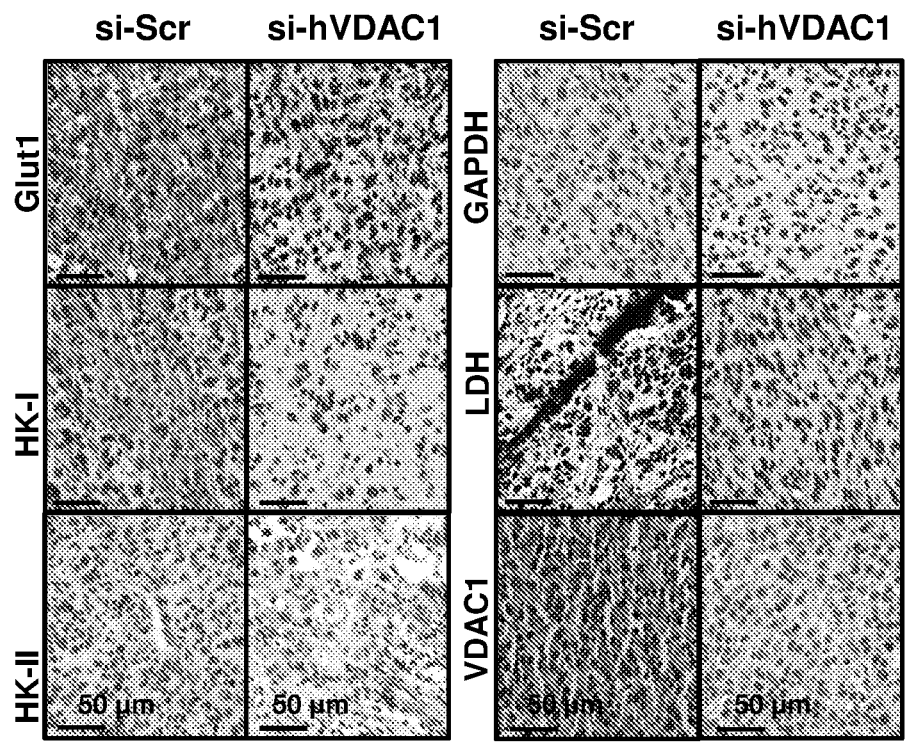
FIG. 8A-C shows IHC staining of si-Scr- or si-hVDAC1-TT sections using specific antibodies against Glut1, HK-I and HK-II.
Figure 8C:
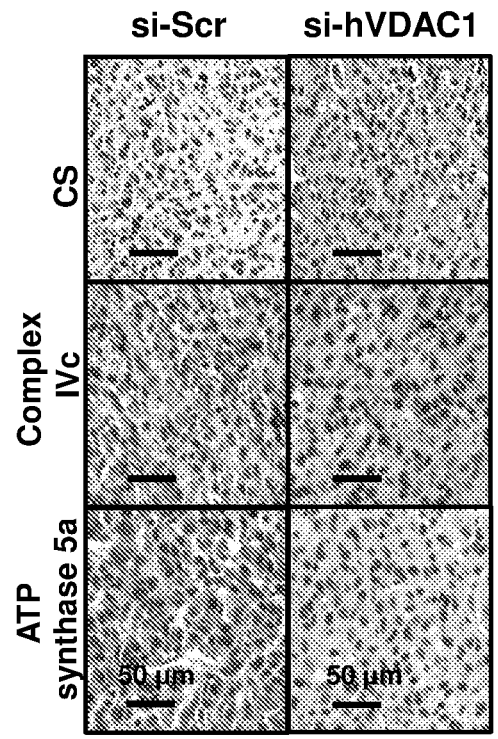
Figure 8D:
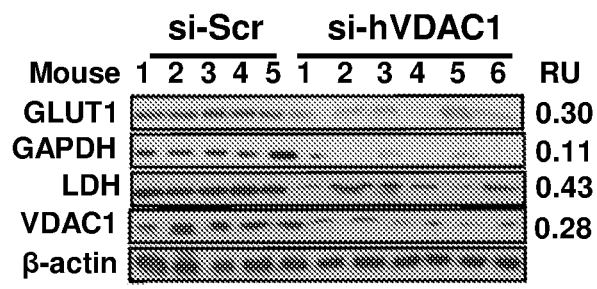
FIG. 8D, E shows Western blot (WB) of selected proteins. RU=relative unit.
Figure 8E:
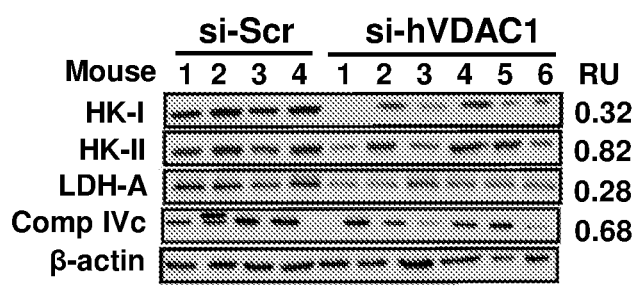
FIG. 8 demonstrates reversal of the U-87MG tumor cell reprogrammed metabolism by si-hVDAC1 treatment.
FIG. 8F shows the decrease in mRNA levels of metabolic enzymes in si-hVDAC1-TTs relative to those in si-Scr-TTs are presented. Results=mean±SEM (n=3-5 tumors), p: *≤0.05;**≤0.001.
FIG. 8G shows representative IHC sections from brains engrafted with si-Scr- or si-VDAC1-treated U-87MG cells, 22 days after cell grafting, stained for Glut 1 and VDAC1.
Figure 8F:
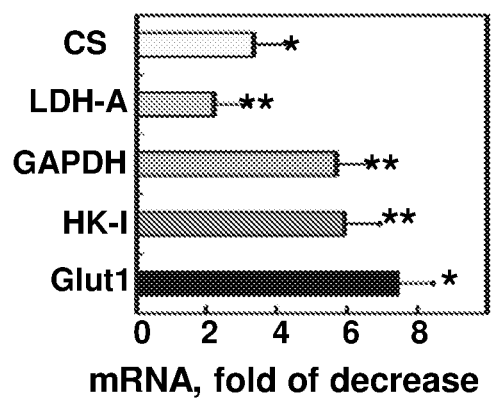
Figure 8G:
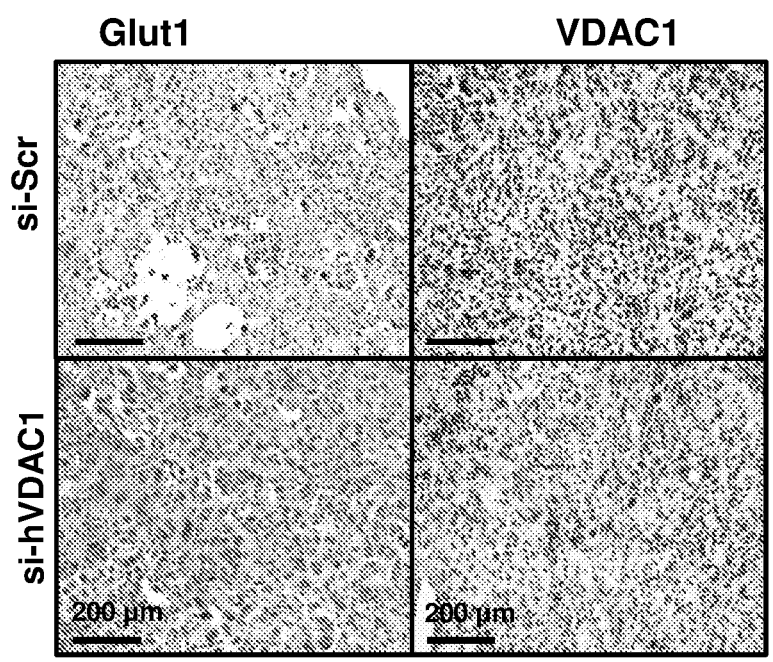

The metabolic alterations that occur during malignant transformation involve a spectrum of functional aberrations and mutations which contribute to elevated glycolysis and increased expression levels of glucose transporters (Glut) and glycolytic enzymes (Koppenol W H et al., 2011. Nature reviews Cancer 11, 325-337) (FIG. 8). si-hVDAC1-TTs showed dramatic decreases of Glut-1, hexokinase (HK-I), glyceraldehyde dehydrogenase (GAPDH) and lactate dehydrogenase (LDH) levels, as compared to si-Scr-TTs (FIG. 8A,B,D,E). Expression levels of the Kreb's cycle enzyme, citrate synthase (CS), the mitochondrial electron transport complex IVc, and ATP synthase 5a were also highly reduced in si-hVDAC1-TTs (FIG. 8C,E), consistent with alterations in oxidative phosphorylation (OXPHOS) Similar results were obtained by qRT-PCR (FIG. 8F). The decreased expression of Kreb's cycle and OXPHOS enzymes is in agreement with the concept that cancer cells use a combination of glycolysis and mitochondria to produce energy, reflecting prevalent normoxic or hypoxic condition. Glioma cells also show similar metabolic flexibility. Similar results were obtained with U-118 xenografts (data not shown). In the orthotopic model, tumors derived from si-Scr-treated U-87MG cells expressed high levels of Glut1, VDAC1 and LDH but not CS or ATP synthase. Neither tumors nor modified expression of these proteins were seen in brain inoculated with si-hVDAC1-treated cells (FIG. 8G). Together, these findings thus point to a reversal of the metabolic reprogramming of cancer cells upon VDAC1.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for inducing the transition of a cancer stem cell and/or quasi differentiated cancer cell to a differentiated cell, the method comprising administrating to, or expressing in the cancer stem cell or quasi differentiated cancer cell an effective amount of a voltage dependent anion channel 1 (VDAC1)-silencing oligonucleotide, comprising the nucleic acid sequence set forth in SEQ ID NO:3 and a complementary sequence thereto.

2. The method of claim 1, wherein the cancer stem cell and/or quasi differentiated cancer cell form part of a tumor of a subject.

3. The method of claim 1, wherein the cancer stem cell and/or quasi differentiated cancer cell is within a cell or tissue culture.

* * * * *

SEQUENCE LISTING

```
<160> NUMBER OF SEQ ID NOS: 94

<210> SEQ ID NO 1
<211> LENGTH: 283
<212> TYPE: PRT
<213> ORGANISM: Homo sapiens

<400> SEQUENCE: 1

Met Ala Val Pro Pro Thr Tyr Ala Asp Leu Gly Lys Ser Ala Arg Asp
1               5                   10                  15

Val Phe Thr Lys Gly Tyr Gly Phe Gly Leu Ile Lys Leu Asp Leu Lys
            20                  25                  30

Thr Lys Ser Glu Asn Gly Leu Glu Phe Thr Ser Ser Gly Ser Ala Asn
        35                  40                  45

Thr Glu Thr Thr Lys Val Thr Gly Ser Leu Glu Thr Lys Tyr Arg Trp
    50                  55                  60

Thr Glu Tyr Gly Leu Thr Phe Thr Glu Lys Trp Asn Thr Asp Asn Thr
65                  70                  75                  80

Leu Gly Thr Glu Ile Thr Val Glu Asp Gln Leu Ala Arg Gly Leu Lys
                85                  90                  95

Leu Thr Phe Asp Ser Ser Phe Ser Pro Asn Thr Gly Lys Lys Asn Ala
            100                 105                 110

Lys Ile Lys Thr Gly Tyr Lys Arg Glu His Ile Asn Leu Gly Cys Asp
        115                 120                 125

Met Asp Phe Asp Ile Ala Gly Pro Ser Ile Arg Gly Ala Leu Val Leu
    130                 135                 140

Gly Tyr Glu Gly Trp Leu Ala Gly Tyr Gln Met Asn Phe Glu Thr Ala
145                 150                 155                 160

Lys Ser Arg Val Thr Gln Ser Asn Phe Ala Val Gly Tyr Lys Thr Asp
                165                 170                 175

Glu Phe Gln Leu His Thr Asn Val Asn Asp Gly Thr Glu Phe Gly Gly
            180                 185                 190

Ser Ile Tyr Gln Lys Val Asn Lys Lys Leu Glu Thr Ala Val Asn Leu
        195                 200                 205
```

```
Ala Trp Thr Ala Gly Asn Ser Asn Thr Arg Phe Gly Ile Ala Ala Lys
    210                 215                 220

Tyr Gln Ile Asp Pro Asp Ala Cys Phe Ser Ala Lys Val Asn Asn Ser
225                 230                 235                 240

Ser Leu Ile Gly Leu Gly Tyr Thr Gln Thr Leu Lys Pro Gly Ile Lys
                245                 250                 255

Leu Thr Leu Ser Ala Leu Leu Asp Gly Lys Asn Val Asn Ala Gly Gly
            260                 265                 270

His Lys Leu Gly Leu Gly Leu Glu Phe Gln Ala
        275                 280
```

```
<210> SEQ ID NO 2
<211> LENGTH: 852
<212> TYPE: DNA
<213> ORGANISM: Homo sapiens

<400> SEQUENCE: 2
atggctgtgc cacccacgta tgccgatctt ggcaaatctg ccaggatgt cttcaccaag      60 ggctatggat ttggcttaat aaagcttgat ttgaaaacaa atctgagaa tggattggaa     120 tttacaagct caggctcagc caacactgag accaccaaag tgacgggcag tctggaaacc    180
aagtacagat ggactgagta cggcctgacg tttacagaga atggaatac cgacaataca     240 ctaggcaccg agattactgt ggaagatcag cttgcacgtg gactgaagct gaccttcgat    300
tcatccttct cacctaacac tgggaaaaaa atgctaaaa tcaagacagg gtacaagcgg     360
gagcacatta acctgggctg cgacatggat ttcgacattg ctgggccttc catccggggt    420
gctctggtgc taggttacga gggctggctg gccggctacc agatgaattt tgagactgca    480
aaatcccgag tgacccagag caactttgca gttggctaca agactgatga attccagctt    540
cacactaatg tgaatgacgg gacagagttt ggcggctcca tttaccagaa agtgaacaag    600
aagttggaga ccgctgtcaa tcttgcctgg acagcaggaa acagtaacac gcgcttcgga    660
atagcagcca agtatcagat tgaccctgac gcctgcttct cggctaaagt gaacaactcc    720
agcctgatag gtttaggata cactcagact ctaaagccag gtattaaact gacactgtca    780
gctcttctgg atggcaagaa cgtcaatgct ggtggccaca gcttggtctc taggactggaa   840 tttcaagcat aa                                                        852
```

```
<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
acacuaggca ccgagauua                                                  19
```

```
<210> SEQ ID NO 4
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 4
gggcuaugga uuuggcuua                                                  19
```

```
<210> SEQ ID NO 5
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 5
gcuuggucua ggacuggaa                                                  19

<210> SEQ ID NO 6
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 6
aagcugaccu ucgauucau                                                  19

<210> SEQ ID NO 7
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 7
gaaugacggg acagaguuu                                                  19

<210> SEQ ID NO 8
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 8
ucggaauagc agccaagua                                                  19

<210> SEQ ID NO 9
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 9
cucuucugga uggcaagaa                                                  19

<210> SEQ ID NO 10
<211> LENGTH: 20
<212> TYPE: RNA
<213> ORGANISM: Artificial Sequence
<220> FEATURE:
<223> OTHER INFORMATION: Synthetic oligonucleotide

<400> SEQUENCE: 10
gaauagcagc caaguaucag                                                 20

<210> SEQ ID NO 11
<211> LENGTH: 19
<212> TYPE: RNA
<213> ORGANISM: Artificial Sequence
<220> FEATURE:
<223> OTHER INFORMATION: Synthetic oligonucleotide
```

```
<400> SEQUENCE: 11
uaagccaaau ccauagccc                                              19

<210> SEQ ID NO 12
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 12
uuccaguccu agaccaagc                                              19

<210> SEQ ID NO 13
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 13
ugauacuugg cugcuauuc                                              19

<210> SEQ ID NO 14
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: 2'-O-methyl modification
<220> FEATURE:
<221> NAME/KEY: misc_feature
<222> LOCATION: (8)..(8)
<223> OTHER INFORMATION: 2'-O-methyl modification
<220> FEATURE:
<221> NAME/KEY: misc_feature
<222> LOCATION: (13)..(13)
<223> OTHER INFORMATION: 2'-O-methyl modification
<220> FEATURE:
<221> NAME/KEY: misc_feature
<222> LOCATION: (17)..(17)
<223> OTHER INFORMATION: 2'-O-methyl modification

<400> SEQUENCE: 14
acacuaggca ccgagauua                                              19

<210> SEQ ID NO 15
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl modification
<220> FEATURE:
<221> NAME/KEY: misc_feature
<222> LOCATION: (16)..(16)
<223> OTHER INFORMATION: 2'-O-methyl modification

<400> SEQUENCE: 15
uaaucucggu gccuagugu                                              19
```

```
<210> SEQ ID NO 16
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 16
acactaggca ccgagatta                                              19

<210> SEQ ID NO 17
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 17
gggctatgga tttggctta                                              19

<210> SEQ ID NO 18
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 18
gcttggtcta ggactggaa                                              19

<210> SEQ ID NO 19
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 19
aagctgacct tcgattcat                                              19

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
gaatgacggg acagagttt                                              19

<210> SEQ ID NO 21
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 21
tcggaatagc agccaagta                                              19

<210> SEQ ID NO 22
<211> LENGTH: 19
<212> TYPE: DNA
<213> ORGANISM: Artificial Sequence
<220> FEATURE:
<223> OTHER INFORMATION: Synthetic oligonucleotide
```

-continued

<400> SEQUENCE: 22
ctcttctgga tggcaagaa					19

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gaatagcagc caagtatcag					20

<210> SEQ ID NO 24
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (8)..(8)
<223> OTHER INFORMATION: 2'-O-methyl-modification
<220> FEATURE:
<221> NAME/KEY: misc_feature
<222> LOCATION: (13)..(13)
<223> OTHER INFORMATION: 2'-O-methyl-modification
<220> FEATURE:
<221> NAME/KEY: misc_feature
<222> LOCATION: (17)..(17)
<223> OTHER INFORMATION: 2'-O-methyl-modification

<400> SEQUENCE: 24
gcaaacaucc cagagguau					19

<210> SEQ ID NO 25
<211> LENGTH: 19
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: 2'-O-methyl-modification
<220> FEATURE:
<221> NAME/KEY: misc_feature
<222> LOCATION: (11)..(11)
<223> OTHER INFORMATION: 2'-O-methyl-modification

<400> SEQUENCE: 25
auaccucugg gauguuugc					19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
actcttccag ccttccttcc					20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
tgttggcgta caggtctttg                                          20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ccaaagtcct ggaggttgaa                                          20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
taactccagg ccatcacaca                                          20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
agtttccagc tgggagaaga g                                        21

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ctttgccatc ccatttctgt a                                        21

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ccagaaccta tgctggtgga                                          20

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33 ggcttttgg cttggttgac t                                         21

```
<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
aggaacaggt atcttggctc t                                              21

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ggggtgtaga ttggtgggaa                                                20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gtagtggaaa accagcagcc                                                20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
cctcctcgtc gcagtagaaa                                                20

<210> SEQ ID NO 38
<211> LENGTH: 22
<212> TYPE: DNA
<213> ORGANISM: Artificial Sequence
<220> FEATURE:
<223> OTHER INFORMATION: Primer

<400> SEQUENCE: 38
tgcaaggatg acttggttac ag                                             22

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
cttctgcaac tgtgtctcca ac                                             22

<210> SEQ ID NO 40
<211> LENGTH: 21
<212> TYPE: DNA
<213> ORGANISM: Artificial Sequence
<220> FEATURE:
<223> OTHER INFORMATION: Primer
```

<400> SEQUENCE: 40
aagctccagg atgaaaccaa c                                      21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
agcgactcaa tcttcctctc c                                      21

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
tggaaggact catgaccaca                                        20

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
atgatgttct ggagagcccc                                        20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
ggccatcttt tctgttgggg                                        20

<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
tcagcattga attccgccg                                         19

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ctgaccctgc actcaatcaa                                        20

```
<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
tccatcggaa ggactaggtg                                               20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
gtctcagtcc agcacgtttg                                               20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gaaacgccgg gaatactgtg                                               20

<210> SEQ ID NO 50
<211> LENGTH: 20
<212> TYPE: DNA
<213> ORGANISM: Artificial Sequence
<220> FEATURE:
<223> OTHER INFORMATION: Primer

<400> SEQUENCE: 50
ccacatggga cttttttgacc                                              20

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51
ttactcggcg acagatttcc                                               20

<210> SEQ ID NO 52
<211> LENGTH: 19
<212> TYPE: DNA
<213> ORGANISM: Artificial Sequence
<220> FEATURE:
<223> OTHER INFORMATION: Primer

<400> SEQUENCE: 52
ctttgggtgc gacttgacg                                                19

<210> SEQ ID NO 53
<211> LENGTH: 18
<212> TYPE: DNA
<213> ORGANISM: Artificial Sequence
<220> FEATURE:
<223> OTHER INFORMATION: Primer
```

<400> SEQUENCE: 53
gtcgaccccg ctcctttt                                                 18

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gcaggtggtt gagagtgctt                                               20

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
gcacccgcct aagattcttc                                               20

<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
tccaaaatcg gatcaacaga c                                             21

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
agagccacat ttggatgtca c                                             21

<210> SEQ ID NO 58
<211> LENGTH: 23
<212> TYPE: DNA
<213> ORGANISM: Artificial Sequence
<220> FEATURE:
<223> OTHER INFORMATION: Primer

<400> SEQUENCE: 58
tgggatttac aggcgtgagc cac                                           23

<210> SEQ ID NO 59
<211> LENGTH: 24
<212> TYPE: DNA
<213> ORGANISM: Artificial Sequence
<220> FEATURE:
<223> OTHER INFORMATION: Primer

<400> SEQUENCE: 59
aagcaaagcc tcccaatccc aaac                                          24

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
agggatcaaa gcctggaaca                                          20

<210> SEQ ID NO 61
<211> LENGTH: 20
<212> TYPE: DNA
<213> ORGANISM: Artificial Sequence
<220> FEATURE:
<223> OTHER INFORMATION: Primer

<400> SEQUENCE: 61
ttggagcctg agacacgatt                                          20

<210> SEQ ID NO 62
<211> LENGTH: 21
<212> TYPE: DNA
<213> ORGANISM: Artificial Sequence
<220> FEATURE:
<223> OTHER INFORMATION: Primer

<400> SEQUENCE: 62
gaaacagcca tagagggcaa a                                        21

<210> SEQ ID NO 63
<211> LENGTH: 23
<212> TYPE: DNA
<213> ORGANISM: Artificial Sequence
<220> FEATURE:
<223> OTHER INFORMATION: Primer

<400> SEQUENCE: 63
tggttttcca gagtcttcag tga                                      23

<210> SEQ ID NO 64
<211> LENGTH: 22
<212> TYPE: DNA
<213> ORGANISM: Artificial Sequence
<220> FEATURE:
<223> OTHER INFORMATION: Primer

<400> SEQUENCE: 64
gggctctccc atgcattcaa ac                                       22

<210> SEQ ID NO 65
<211> LENGTH: 22
<212> TYPE: DNA
<213> ORGANISM: Artificial Sequence
<220> FEATURE:
<223> OTHER INFORMATION: Primer

<400> SEQUENCE: 65
caccttccct ccaaccagtt gc                                       22

<210> SEQ ID NO 66
<211> LENGTH: 20
<212> TYPE: DNA
<213> ORGANISM: Artificial Sequence
<220> FEATURE:
<223> OTHER INFORMATION: Primer

```
<400> SEQUENCE: 66
gccgagatct cagccatatt                                               20

<210> SEQ ID NO 67
<211> LENGTH: 20
<212> TYPE: DNA
<213> ORGANISM: Artificial Sequence
<220> FEATURE:
<223> OTHER INFORMATION: Primer

<400> SEQUENCE: 67
atgtacttag aggtacaaat                                               20

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tgacagagga acgggggtat                                               20

<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
cggctgtgat caaatggcag                                               20

<210> SEQ ID NO 70
<211> LENGTH: 20
<212> TYPE: DNA
<213> ORGANISM: Artificial Sequence
<220> FEATURE:
<223> OTHER INFORMATION: Primer

<400> SEQUENCE: 70
agtggttctt ctgcgctact                                               20

<210> SEQ ID NO 71
<211> LENGTH: 21
<212> TYPE: DNA
<213> ORGANISM: Artificial Sequence
<220> FEATURE:
<223> OTHER INFORMATION: Primer

<400> SEQUENCE: 71
ctgctggaag gtaaactctg g                                             21

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
acatacagtg attatttccc cgt                                           23
```

```
<210> SEQ ID NO 73
<211> LENGTH: 20
<212> TYPE: DNA
<213> ORGANISM: Artificial Sequence
<220> FEATURE:
<223> OTHER INFORMATION: Primer

<400> SEQUENCE: 73
cgccccaaag atgaggagta                                               20

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
aggagaggtc cgaggaggtg                                               20

<210> SEQ ID NO 75
<211> LENGTH: 20
<212> TYPE: DNA
<213> ORGANISM: Artificial Sequence
<220> FEATURE:
<223> OTHER INFORMATION: Primer

<400> SEQUENCE: 75
ctcagctcca cctccgatag                                               20

<210> SEQ ID NO 76
<211> LENGTH: 21
<212> TYPE: DNA
<213> ORGANISM: Artificial Sequence
<220> FEATURE:
<223> OTHER INFORMATION: Primer

<400> SEQUENCE: 76
ccatgcaggt tgacaccgtt g                                             21

<210> SEQ ID NO 77
<211> LENGTH: 21
<212> TYPE: DNA
<213> ORGANISM: Artificial Sequence
<220> FEATURE:
<223> OTHER INFORMATION: Primer

<400> SEQUENCE: 77
tcggcagact gattcaaata a                                             21

<210> SEQ ID NO 78
<211> LENGTH: 21
<212> TYPE: DNA
<213> ORGANISM: Artificial Sequence
<220> FEATURE:
<223> OTHER INFORMATION: Primer

<400> SEQUENCE: 78
tgaaatagct tagcggcaag a                                             21

<210> SEQ ID NO 79
<211> LENGTH: 21
<212> TYPE: DNA
<213> ORGANISM: Artificial Sequence
<220> FEATURE:
<223> OTHER INFORMATION: Primer
```

<400> SEQUENCE: 79
gtgaatcggg aacagttgtg t                                          21

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
aagaggtggc tgcttcaaac                                            20

<210> SEQ ID NO 81
<211> LENGTH: 20
<212> TYPE: DNA
<213> ORGANISM: Artificial Sequence
<220> FEATURE:
<223> OTHER INFORMATION: Primer

<400> SEQUENCE: 81
agcctagatt ttcggccatc                                            20

<210> SEQ ID NO 82
<211> LENGTH: 20
<212> TYPE: DNA
<213> ORGANISM: Artificial Sequence
<220> FEATURE:
<223> OTHER INFORMATION: Primer

<400> SEQUENCE: 82
atgaatcagt ggatggcaca                                            20

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ccattgagtg cctggatctt                                            20

<210> SEQ ID NO 84
<211> LENGTH: 20
<212> TYPE: DNA
<213> ORGANISM: Artificial Sequence
<220> FEATURE:
<223> OTHER INFORMATION: Primer

<400> SEQUENCE: 84
ctcaggggcc tttggacatc                                            20

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
caggcagtcg cagttttcac                                            20

```
<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
tcttacgagg agctgcagac                                                   20

<210> SEQ ID NO 87
<211> LENGTH: 20
<212> TYPE: DNA
<213> ORGANISM: Artificial Sequence
<220> FEATURE:
<223> OTHER INFORMATION: Primer

<400> SEQUENCE: 87
tatccagctc cagagtctct                                                   20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
ttcctgaggc acctgaagag                                                   20

<210> SEQ ID NO 89
<211> LENGTH: 23
<212> TYPE: DNA
<213> ORGANISM: Artificial Sequence
<220> FEATURE:
<223> OTHER INFORMATION: Primer

<400> SEQUENCE: 89
ggtgttccat tttcatcatg acc                                               23

<210> SEQ ID NO 90
<211> LENGTH: 20
<212> TYPE: DNA
<213> ORGANISM: Artificial Sequence
<220> FEATURE:
<223> OTHER INFORMATION: Primer

<400> SEQUENCE: 90
tagtgtgccc aaccatgagt                                                   20

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
ttgcattctt cactggacca                                                   20

<210> SEQ ID NO 92
<211> LENGTH: 20
<212> TYPE: DNA
<213> ORGANISM: Artificial Sequence
<220> FEATURE:
<223> OTHER INFORMATION: Primer
```

```
<400> SEQUENCE: 92
aggttggctc tgactgtacc                                                    20

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
aaagctgttc cgtcccagta                                                    20

<210> SEQ ID NO 94
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 94
uaaucucggu gccuagugu                                                     19
```